(12) United States Patent
Walker et al.

(10) Patent No.: US 12,065,468 B2
(45) Date of Patent: Aug. 20, 2024

(54) HEME-BINDING SMALL PEPTIDE

(71) Applicant: Massachusetts Institute of Technology, Cambridge, MA (US)

(72) Inventors: Graham C. Walker, Cambridge, MA (US); Siva Sankari Iyer Mani Sankaran, Quincy, MA (US); Vigneshbabu Musuri Periasamy, Quincy, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 32 days.

(21) Appl. No.: 18/045,914

(22) Filed: Oct. 12, 2022

(65) Prior Publication Data

US 2023/0111409 A1  Apr. 13, 2023

Related U.S. Application Data

(60) Provisional application No. 63/369,812, filed on Jul. 29, 2022, provisional application No. 63/255,089, filed on Oct. 13, 2021.

(51) Int. Cl.
*C07K 14/21* (2006.01)

(52) U.S. Cl.
CPC .................. *C07K 14/21* (2013.01)

(58) Field of Classification Search
CPC .................................... C07K 14/21
See application file for complete search history.

(56) References Cited

U.S. PATENT DOCUMENTS

2012/0157374 A1   6/2012   Kondorosi-Kuzsel
2021/0024655 A1   1/2021   Altae-Tran et al.

FOREIGN PATENT DOCUMENTS

WO   WO-2010146067 A1 *  12/2010   ........... A61K 38/168

OTHER PUBLICATIONS

Sankari et al. 2022 (A haem-sequestering plant promotes iron uptake in symbiotic bacteria; Nat. Microbiol. 7(9):1453-1465). (Year: 2022).*
Lee, J. S. & Kim-Shapiro, D. B. Stored blood: How old is too old? J. Clin. Invest. 127, 100-102 (2017).
Lehrer, R. I. & Ganz, T. Endogenous vertebrate antibiotics. Defensins, protegrins, and other cysteine-rich antimicrobial peptides. Ann. N. Y. Acad. Sci. 797, 228-239 (1996).
Leigh, J. A., Signer, E. R. & Walker, G. C. Exopolysaccharide-deficient mutants of Rhizobium meliloti that form ineffective nodules. Proc. Natl. Acad. Sci. U. S. A. 82, 6231-6235 (1985).
Letoffe, S., Delepelaire, P. & Wandersman, C. The housekeeping dipeptide permease is the *Escherichia coli* heme transporter and functions with two optional peptide binding proteins. Proc. Natl. Acad. Sci. U. S. A. 103, 12891-12896 (2006).
Li, T., Bonkovsky, H. L. & Guo, J. T. Structural analysis of heme proteins: Implications for design and prediction. BMC Struct. Biol. 11, 1-13 (2011).
Lima, R. M., Kylarová, S., Mergaert, P. & Kondorosi, É. Unexplored Arsenals of Legume Peptides With Potential for Their Applications in Medicine and Agriculture. Front. Microbiol. 11, (2020).
Marlow, V. L. et al. Essential role for the BacA protein in the uptake of a truncated eukaryotic peptide in Sinorhizobium meliloti. J. Bacteriol. 191, 1519-1527 (2009).
Michener, J. K., Nielsen, J. & Smolke, C. D. Identification and treatment of heme depletion attributed to overexpression of a lineage of evolved P450 monooxygenases. Proc. Natl. Acad. Sci. U. S. A. 109, 19504-19509 (2012).
Mikulass, K. R. et al. Antimicrobial nodule-specific cysteine-rich peptides disturb the integrity of bacterial outer and inner membranes and cause loss of membrane potential. Ann. Clin. Microbiol. Antimicrob. 15, 43 (2016).
Mitra, A., Ko, Y. H., Cingolani, G. & Niederweis, M. Heme and hemoglobin utilization by *Mycobacterium tuberculosis*. Nat. Commun. 10, 1-14 (2019).
Miyamoto, et al., "D-amino acid metabolism in bacteria." Journal of Biochemistry, 170(1): 5-13 (Mar. 2021).
Montiel, J. et al. Morphotype of bacteroids in different legumes correlates with the number and type of symbiotic NCR peptides. doi: 10.1073/pnas.1704217114.
Morton, D. J., Seale, T. W., Vanwagoner, T. M., Whitby, P. W. & Stull, T. L. The dppBCDF gene cluster of Haemophilus influenzae: Role in heme utilization. BMC Res. Notes 2, 166 (2009).
Natera, S. H. A., Guerreiro, N. & Djordjevic, M. A. Proteome analysis of differentially displayed proteins as a tool for the investigation of symbiosis. Mol. Plant-Microbe Interact. 13, 995-1009 (2000).
O'Brian, M. R. Perception and Homeostatic Control of Iron in the Rhizobia and Related Bacteria. Annu. Rev. Microbiol. 69, 229-245 (2015).
Ofori-Acquah, S. F. et al. Hemopexin deficiency promotes acute kidney injury in sickle cell disease. Blood 135, 1044-1048 (2020).
Pellicer Martinez, M. T. et al. Sensing iron availability via the fragile [4Fe—4S] cluster of the bacterial transcriptional repressor RirA †. (2017) doi:10.1039/c7sc02801f.
Penterman, J. et al. Host plant peptides elicit a transcriptional response to control the Sinorhizobium meliloti cell cycle during symbiosis. Proc. Natl. Acad. Sci. U. S. A. 111, 3561-3566 (2014).
Perner, J., Gasser, R. B., Oliveira, P. L. & Kopacek, P. Heme Biology in Metazoan Parasites—'The Bright Side of Heme'. Trends Parasitol. 35, 213-225 (2019).
Poje, G. & Redfield, R. J. General methods for culturing Haemophilus influenzae. Methods Mol. Med. 71, 51-56 (2003).

(Continued)

*Primary Examiner* — Mary Maille Lyons
(74) *Attorney, Agent, or Firm* — MCDONNELL BOEHNEN HULBERT & BERGHOFF LLP

(57) ABSTRACT

The disclosure provides heme binding peptides and their use for treating disorders that can benefit from sequestering free heme.

14 Claims, 21 Drawing Sheets

Specification includes a Sequence Listing.

(56) References Cited

OTHER PUBLICATIONS

Qi, Z., Hamza, I. & O'Brian, M. R. Heme is an effector molecule for iron-dependent degradation of the bacterial iron response regulator (Irr) protein. Proc. Natl. Acad. Sci. U. S. A. 96, 13056-13061 (1999).
Ribeiro, C. W. et al. Regulation of Differentiation of Nitrogen-Fixing Bacteria by Microsymbiont Targeting of Plant Thioredoxin s1. Curr. Biol. 27, 250-256 (2017).
Richard, K. L., Kelley, B. R. & Johnson, J. G. Heme uptake and utilization by gram-negative bacterial pathogens. Front. Cell. Infect. Microbiol. 9, 81 (2019).
Robertsen, B. K., Åman, P., Darvill, A. G., McNeil, M. & Albersheim, P. Host-Symbiont Interactions. Plant Physiol. 67, 389-400 (1981).
Roux, B. et al. An integrated analysis of plant and bacterial gene expression in symbiotic root nodules using laser-capture microdissection coupled to RNA sequencing. Plant J. 77, 817-837 (2014).
Sankari, S. & O'Brian, M. R. The Bradyrhizobium japonicum ferrous iron transporter FeoAB is required for ferric iron utilization in free living aerobic cells and for symbiosis. J. Biol. Chem. 291, 15653-15662 (2016).
Sassa, S. Sequential induction of heme pathway enzymes during erythroid differentiation of mouse friend leukemia virus-infected cells. J. Exp. Med. 143, 305-315 (1976).
Schafer, A. et al. Small mobilizable multi-purpose cloning vectors derived from the *Escherichia coli* plasmids pK18 and pK19: selection of defined deletions in the chromosome of Corynebacterium glutamicum. Gene 145, 69-73 (1994).
Seal, M., Ghosh, C., Basu, O. & Dey, S. G. Cytochrome c peroxidase activity of heme bound amyloid β peptides. J. Biol. Inorg. Chem. 21, 683-690 (2016).
Seibert, M., Lien, S., Weaver, P. F. & Janzen, A. F. Photobiological Production of Hydrogen and Electricity. 273-229 (1981) doi:10.1016/b978-0-08-025388-6.50039-8.
Seixas, E. et al. Heme oxygenase-1 affords protection against noncerebral forms of severe malaria. Proc. Natl. Acad. Sci. U. S. A. 106, 15837-15842 (2009).
Sevier, C. S. & Kaiser, C. A. Formation and transfer of disulphide bonds in living cells. Nat. Rev. Mol. Cell Biol. 3, 836-847 (2002).
Shabab, M. et al. Disulfide cross-linking influences symbiotic activities of nodule peptide NCR247. Proc. Natl. Acad. Sci. U. S. A. 113, 10157-10162 (2016).
Shah, N. B. & Duncan, T. M. Bio-layer interferometry for measuring kinetics of protein-protein interactions and allosteric ligand effects. J. Vis. Exp. 84, 51383 (2014).
Shimizu, T. Binding of cysteine thiolate to the Fe(III) heme complex is critical for the function of heme sensor proteins. J. Inorg. Biochem. 108, 171-177 (2012).
Singleton, C. et al. Heme-responsive DNA binding by the global iron regulator Irr from rhizobium leguminosarum. J. Biol. Chem. 285, 16023-16031 (2010).
Smith, A. & McCulloh, R. J. Mechanisms of heme toxicity in haemolysis and protection by the heme-binding protein, haemopexin. ISBT Sci. Ser. 12, 119-133 (2017).
Srivastava, S. et al. Cysteine-rich antimicrobial peptides from plants: The future of antimicrobial therapy. Phytotherapy Research vol. 35 256-277 (2021).
Takeda, S., Kamiya, N. & Nagamune, T. A novel protein-based heme sensor consisting of green fluorescent protein and apocytochrome b562. Anal. Biochem. 317, 116-119 (2003).
Terry, R. E., Soerensen, K. U., Von Jolley, D. & Brown, J. C. The role of active Bradyrhizobium japonicum in iron stress response of soybeans. Plant Soil 130, 225-230 (1991).
Tucker, A. T. et al. Discovery of Next-Generation Antimicrobials through Bacterial Self-Screening of Surface-Displayed Peptide Libraries. Cell 172, 618-628.e13 (2018).
Van De Velde, W. et al. Plant peptides govern terminal differentiation of bacteria in symbiosis. Science (80-.). 327, 1122-1126 (2010).
Vinchi, F. et al. Hemopexin therapy improves cardiovascular function by preventing heme-induced endothelial toxicity in mouse models of hemolytic diseases. Circulation 127, 1317-1329 (2013).
Wagener, B. M. et al. Role of heme in lung bacterial infection after trauma hemorrhage and stored red blood cell transfusion: A preclinical experimental study. PLoS Med. 15, (2018).
Wang, T. et al. Heme Sequestration as an Effective Strategy for the Suppression of Tumor Growth and Progression. Mol. Cancer Ther. 20, 2506-2518 (2021).
Yang, J. et al. Bradyrhizobium japonicum senses iron through the status of heme to regulate iron homeostasis and metabolism. Mol. Microbiol. 60, 427-437 (2006).
Zhang, H. et al. Insights into irr and rira gene regulation on the virulence of brucella melitensis m5-90. Can. J. Microbiol. 66, 351-358 (2020).
Shane Thomas (Authorized Officer), International Search Report and Written Opinion for PCT/US2022/77948, mailed Mar. 8, 2023.
Aldag, C. et al. Probing the role of the proximal heme ligand in cytochrome P450cam by recombinant incorporation of selenocysteine. Proc. Natl. Acad. Sci. U. S. A. 106, 5481-5486 (2009).
Arnold, M. F. F. et al. Genome-Wide Sensitivity Analysis of the Microsymbiont Sinorhizobium meliloti to Symbiotically Important, Defensin-Like Host Peptides. (2017).
Atamna, H. & Boyle, K. Amyloid-β peptide binds with heme to form a peroxidase: Relationship to the cytopathologies of Alzheimer's disease. Proc. Natl. Acad. Sci. U. S. A. 103, 3381-3386 (2006).
Babu, V. M. P., Sankari, S., Budnick, J. A., Caswell, C. C. & Walker, G. C. Sinorhizobium meliloti YbeY is a zinc-dependent single-strand specific endoribonuclease that plays an important role in 16S ribosomal RNA processing. Nucleic Acids Res. 48, 332-348 (2020).
Barr, I. & Guo, F. Pyridine Hemochromagen Assay for Determining the Concentration of Heme in Purified Protein Solutions. Bio-Protocol 5, (2015).
Barr, I. et al. DiGeorge Critical Region 8 (DGCR8) is a double-cysteine-ligated heme protein. J. Biol. Chem. 286, 16716-16725 (2011).
Barr, I. et al. Ferric, not ferrous, heme activates RNA-binding protein DGCR8 for primary microRNA processing. Proc. Natl. Acad. Sci. U. S. A. 109, 1919-1924 (2012).
Benyamina, S. M. et al. Two Sinorhizobium meliloti glutaredoxins regulate iron metabolism and symbiotic bacteroid differentiation. Environ. Microbiol. 15, 795-810 (2013).
Bergmann, A. et al. Toxoplasma gondii requires its plant-like heme biosynthesis pathway for infection. PLoS Pathog. 16, e1008499 (2020).
Brear, E. M., Day, D. A. & Smith, P. M. C. Iron: An essential micronutrient for the legume-rhizobium symbiosis. Front. Plant Sci. 4, (2013).
Brewitz, H. H. et al. Heme interacts with histidine- and tyrosine-based protein motifs and inhibits enzymatic activity of chloramphenicol acetyltransferase from *Escherichia coli*. Biochim. Biophys. Acta—Gen. Subj. 1860, 1343-1353 (2016).
Cermak, T. et al. A Multipurpose Toolkit to Enable Advanced Genome Engineering in Plants. Plant Cell 29, 1196-1217 (2017).
Chao, T. C., Buhrmester, J., Hansmeier, N., Pühler, A. & Weidner, S. Role of the regulatory gene rirA in the transcriptional response of Sinorhizobium meliloti to iron limitation. Appl. Environ. Microbiol. 71, 5969-5982 (2005).
Chiabrando, D., Fiorito, V., Petrillo, S. & Tolosano, E. Unraveling the role of heme in neurodegeneration. Frontiers in Neuroscience vol. 12 (2018).
Costa, D., Amarelle, V., Valverde, C., O'Brian, M. R. & Fabiano, E. The Irr and RirA proteins participate in a complex regulatory circuit and act in concert to modulate bacterioferritin expression in Ensifer meliloti 1021. Appl. Environ. Microbiol. 83, 895-912 (2017).
Delgado, M. J., Bedmar, E. J. & Downie, J. A. Genes involved in the formation and assembly of rhizobial cytochromes and their role in symbiotic nitrogen fixation. Adv. Microb. Physiol. 40, 191-231 (1998).
Downie, J. A. & Kondorosi, E. Why Should Nodule Cysteine-Rich (NCR) Peptides Be Absent From Nodules of Some Groups of Legumes but Essential for Symbiotic N-Fixation in Others? Front. Agron. 3, 42 (2021).
Einsle, O. et al. Nitrogenase MoFe-protein at 1.16 Å resolution: A central ligand in the FeMo-cofactor. Science (80-.). 297, 1696-1700 (2002).

(56) References Cited

OTHER PUBLICATIONS

Farkas, A. et al. Medicago truncatula symbiotic peptide NCR247 contributes to bacteroid differentiation through multiple mechanisms. Proc. Natl. Acad. Sci. U. S. A. 111, 5183-5188 (2014).

Ferguson, A. P. et al. Importance of unusually modified lipid A in Sinorhizobium stress resistance and legume symbiosis. Mol. Microbiol. 56, 68-80 (2005).

Ferguson, G. P., Roop, R. M. & Walker, G. C. Deficiency of a Sinorhizobium meliloti bacA mutant in alfalfa symbiosis correlates with alteration of the cell envelope. J. Bacteriol. 184, 5625-5632 (2002).

Fiorito, V., Chiabrando, D., Petrillo, S., Bertino, F. & Tolosano, E. The Multifaceted Role of Heme in Cancer. Front. Oncol. 9, 1540 (2020).

Ghosal, A. et al. C21orf57 is a human homologue of bacterial YbeY proteins. Biochem. Biophys. Res. Commun. 484, 612-617 (2017).

Ghosh, C., Seal, M., Mukherjee, S. & Ghosh Dey, S. Alzheimer's Disease: A Heme-Aβ Perspective. Accounts of Chemical Research vol. 48 2556-2564 (2015).

Gibson, K. E., Kobayashi, H. & Walker, G. C. Molecular determinants of a symbiotic chronic infection. Annu. Rev. Genet. 42, 413-441 (2008).

Girvan, H. M. et al. Analysis of Heme Iron Coordination in DGCR8: The Heme-Binding Component of the Microprocessor Complex. Biochemistry 55, 5073-5083 (2016).

González-Guerrero, M., Matthiadis, A., Sáez, Á. & Long, T. A. Fixating on metals: New insights into the role of metals in nodulation and symbiotic nitrogen fixation. Front. Plant Sci. 5, 45 (2014).

Gouveia, Z. et al. Characterization of plasma labile heme in hemolytic conditions. FEBS J. 284, 3278-3301 (2017).

Graw, J. A. et al. Haptoglobin or hemopexin therapy prevents acute adverse effects of resuscitation after prolonged storage of red cells. Circulation 134, 945-960 (2016).

Guefrachi, I. et al. Bradyrhizobium BclA Is a Peptide Transporter Required for Bacterial Differentiation in Symbiosis with Aeschynomene Legumes. 28, (2015).

Guo, Y., Wallace, S. S. & Bandaru, V. A novel bicistronic vector for overexpressing Mycobacterium tuberculosis proteins in Escherichia coli. Protein Expr. Purif. 65, 230-237 (2009).

Halai, R. & Craik, D. J. Conotoxins: Natural product drug leads. Natural Product Reports vol. 26 526-536 (2009).

Hamza, I., Chauhan, S., Hassett, R. & O'Brian, M. R. The bacterial irr protein is required for coordination of heme biosynthesis with iron availability. J. Biol. Chem. 273, 21669-21674 (1998).

Haney, C. H. & Long, S. R. Plant flotillins are required for infection by nitrogen-fixing bacteria. Proc. Natl. Acad. Sci. U. S. A. 107, 478-483 (2010).

Hibbing, M. E. & Fuqua, C. Antiparallel and interlinked control of cellular iron levels by the Irr and RirA regulators of Agrobacterium tumefaciens. J. Bacteriol. 193, 3461-3472 (2011).

Horvath, B. et al. Loss of the nodule-specific cysteine rich peptide, NCR169, abolishes symbiotic nitrogen fixation in the Medicago truncatula dnf7 mutant. doi: 10.1073/pnas.1500777112.

Hrkal, Z., Vodrážka, Z. & Kalousek, I. Transfer of Heme from Ferrihemoglobin and Ferrihemoglobin Isolated Chains to Hemopexin. Eur. J. Biochem. 43, 73-78 (1974).

Immenschuh, S., Vijayan, V., Janciauskiene, S. & Gueler, F. Heme as a target for therapeutic interventions. Front. Pharmacol. 8, 146 (2017).

Ishida, M., Dohmae, N., Shiro, Y. & Isogai, Y. Synthesis of biotinylated heme and its application to panning heme-binding proteins. Anal. Biochem. 321, 138-141 (2003).

Juhasz, T. et al. Interplay between membrane active host defense peptides and heme modulates their assemblies and in vitro activity. Sci. Reports | 11, 18328 (123AD).

Kamal, J. K. A. & Behere, D. V. Binding of heme to human serum albumin: Steady-state fluorescence, circular dichroism and optical difference spectroscopic studies. Indian J. Biochem. Biophys. 42, 7-12 (2005).

Kim, M. et al. An antimicrobial peptide essential for bacterial survival in the nitrogen-fixing symbiosis. Proc. Natl. Acad. Sci. U. S. A. 112, 15238-15243 (2015).

Kishimoto, Y., Kondo, K. & Momiyama, Y. The Protective Role of Heme Oxygenase-1 in Atherosclerotic Diseases. Int. J. Mol. Sci. 20, (2019).

Koreny, L., Obornik, M. & Lukes, J. Make It, Take It, or Leave It: Heme Metabolism of Parasites. PLoS Pathog. 9, (2013).

Kuhl, T. et al. Analysis of Fe(III) heme binding to cysteine-containing heme-regulatory motifs in proteins. ACS Chem. Biol. 8, 1785-1793 (2013).

Kupke, T., Klare, J. P. & Brügger, B. Heme binding of transmembrane signaling proteins undergoing regulated intramembrane proteolysis. Commun. Biol. 3, 1-16 (2020).

Larsen, R. et al. A central role for free heme in the pathogenesis of severe sepsis. Sci. Transl. Med. 2, 51ra71-51ra71 (2010).

Larsen, R., Gouveia, Z., Soares, M. P. & Gozzelino, R. Heme cytotoxicity and the pathogenesis of immune-mediated inflammatory diseases. Front. Pharmacol. May 3, 77 (2012).

Layer, R. T. & McIntosh, J. M. Conotoxins: Therapeutic potential and application. Marine Drugs vol. 4 119-142 (2006).

\* cited by examiner

FeuP-FeuQ

Exo-ChvI

A

B

Anti-GFP Western Blot

SEQUENCE LISTING

```
Sequence total quantity: 14
SEQ ID NO: 1            moltype = AA   length = 24
FEATURE                 Location/Qualifiers
source                  1..24
                        mol_type = protein
                        organism = synthetic construct
SEQUENCE: 1
RNGCIVDPRC PYQQCRRPLY CRRR                                              24

SEQ ID NO: 2            moltype = AA   length = 21
FEATURE                 Location/Qualifiers
source                  1..21
                        mol_type = protein
                        organism = synthetic construct
SEQUENCE: 2
RNGCIVDPRC PYQQCRRPLY C                                                 21

SEQ ID NO: 3            moltype = AA   length = 24
FEATURE                 Location/Qualifiers
source                  1..24
                        mol_type = protein
                        organism = synthetic construct
MOD_RES                 22..24
                        note = X is any amino acid except R
SEQUENCE: 3
RNGCIVDPRC PYQQCRRPLY CXXX                                              24

SEQ ID NO: 4            moltype = AA   length = 24
FEATURE                 Location/Qualifiers
source                  1..24
                        mol_type = protein
                        organism = synthetic construct
SEQUENCE: 4
RNGCIVDPRC PYQQCRRPLY CAAA                                              24

SEQ ID NO: 5            moltype = AA   length = 24
FEATURE                 Location/Qualifiers
source                  1..24
                        mol_type = protein
                        organism = synthetic construct
SEQUENCE: 5
RNGCIVDARC PYQKCSYPLY CRRR                                              24

SEQ ID NO: 6            moltype = AA   length = 21
FEATURE                 Location/Qualifiers
source                  1..21
                        mol_type = protein
                        organism = synthetic construct
SEQUENCE: 6
RNGCIVDARC PYQKCSYPLY C                                                 21

SEQ ID NO: 7            moltype = AA   length = 24
FEATURE                 Location/Qualifiers
source                  1..24
                        mol_type = protein
                        organism = synthetic construct
MOD_RES                 22..24
                        note = X is any amino acid except R
SEQUENCE: 7
RNGCIVDARC PYQKCSYPLY CXXX                                              24

SEQ ID NO: 8            moltype = AA   length = 24
FEATURE                 Location/Qualifiers
source                  1..24
                        mol_type = protein
                        organism = synthetic construct
SEQUENCE: 8
RNGCIVDARC PYQKCSYPLY CAAA                                              24

SEQ ID NO: 9            moltype = AA   length = 20
FEATURE                 Location/Qualifiers
source                  1..20
                        mol_type = protein
                        organism = synthetic construct
SEQUENCE: 9
RPNGCLLNPR CPYATDRCRA                                                   20

SEQ ID NO: 10           moltype = AA   length = 24
```

```
FEATURE              Location/Qualifiers
source               1..24
                     mol_type = protein
                     organism = synthetic construct
SEQUENCE: 10
DRPTGCLLNP RCPYATEYCR QVEP                                              24

SEQ ID NO: 11        moltype = AA  length = 6
FEATURE              Location/Qualifiers
source               1..6
                     mol_type = protein
                     organism = synthetic construct
SEQUENCE: 11
ALFLVV                                                                   6

SEQ ID NO: 12        moltype = AA  length = 6
FEATURE              Location/Qualifiers
source               1..6
                     mol_type = protein
                     organism = synthetic construct
SEQUENCE: 12
ALFMVV                                                                   6

SEQ ID NO: 13        moltype = AA  length = 16
FEATURE              Location/Qualifiers
source               1..16
                     mol_type = protein
                     organism = synthetic construct
SEQUENCE: 13
GCLLNPRCPY ATEYCR                                                       16

SEQ ID NO: 14        moltype = AA  length = 16
FEATURE              Location/Qualifiers
source               1..16
                     mol_type = protein
                     organism = synthetic construct
SEQUENCE: 14
GCLLNPRCPY ATEYCR                                                       16
```

HEME-BINDING SMALL PEPTIDE

CROSS REFERENCE

This application claims priority to U.S. Provisional Application Ser. No. 63/255,089 filed Oct. 13, 2021 and 63/369,812 filed Jul. 29, 2022, each incorporated by reference herein in their entirety.

FEDERAL FUNDING STATEMENT

This invention was made with Government support under Grant No. R01 GM031030 awarded by the National Institutes of Health. The Government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Oct. 6, 2022 having the file name "22-1474-US.xml" and is 14 kb in size.

BACKGROUND

Heme is a complex of iron and the tetrapyrrole protoporphyrin IX that carries out essential functions in aerobic organisms. As the prosthetic group of hemoglobin and myoglobin, heme plays a crucial role in the reversible oxygen binding and transport needed for respiration as well as other roles in respiration as a component of cytochromes. When complexed to other proteins, heme plays roles in chemical catalysis (particularly catalases and peroxidases that reduce oxidative stress and in certain enzymes that carry out important oxidative reactions), diatomic gas detection, and other functions. In addition, in humans and mammals it is important for even more functions such as microRNA processing and circadian rhythms. Heme can also serve as a source of iron for various bacterial pathogens and some pathogenic eukaryotic organisms.

SUMMARY

In one aspect, the disclosure provides peptides comprising or consisting of the amino acid sequence selected from the group consisting of SEQ ID NO:1-10, wherein 1 or more amino acid residues are D amino acids. In some embodiments, 2, 3, 4, 5, 6, 7, 8, 9, 10, 11, 12, 13, 14, 15, 16, 17, 18, 19, 20, 21, 22, 23, or all amino acid residues are D amino acids. In another aspect, the disclosure provides polypeptides, comprising a first peptide comprising the amino acid sequence selected from the group consisting of SEQ ID NO:1-10 linked to a functional domain. In another embodiment, the disclosure provides compositions, comprising a peptide comprising the amino acid sequence selected from the group consisting of SEQ ID NO:1-10, fixed to a support. In another embodiment, the disclosure provides formulations comprising the peptide, polypeptide, or composition of any embodiment of the disclosure; and an anti-oxidant. In a further embodiment, the disclosure provides pharmaceutical compositions, comprising the peptide, polypeptide, composition, or formulation of any embodiment of the disclosure; and a pharmaceutically acceptable carrier.

In one embodiment, the disclosure provides methods of sequestering heme from an environment and rendering the heme biologically inaccessible, the method comprising contacting said environment with an NCR247 peptide, derivatives, variants, homologs, or enantiomers thereof. In another embodiment, the disclosure provides methods of inhibiting pathogen growth in a subject by sequestering heme in the subject and rendering the heme biologically inaccessible, the method comprising administering to said subject an NCR247 peptide, derivatives, variants, homologs, or enantiomers thereof. In a further embodiment, the disclosure provides methods of reducing toxicity of free heme arising from a disease, disorder, or condition arising due to free heme in a subject, the method comprising administering to the subject an NCR247 peptide, derivatives, variants, homologs, or enantiomers thereof. In one embodiment, the disclosure provides methods of treating a disease, disorder or condition in a subject by sequestering heme in the subject and rendering the heme biologically inaccessible, the method comprising administering to said subject an NCR247 peptide, derivatives, variants, homologs, or enantiomers thereof.

In one embodiment, the disclosure provides methods for treating or limiting development of a subject having a disorder, comprising administering to the subject an amount effective to treat the disorder of an NCR247 peptide, derivative, variant, homolog, or enantiomer thereof, wherein the disorder is selected from the group consisting of a bacterial infection, a fungal infection, a kinetoplastid infection, an apicomplexan infection, a parasitic worm infection, sepsis, toxoplasmosis, Chagas disease, and Leischmaniasis, malaria, cancer, Alzheimer's Disease, atherosclerosis, an inherited hemolytic disorder, ischemia reperfusion injury, sickle cell disease, β-thalassemia, tuberculosis, sleeping sickness, leishmaniasis, lymphatic filariasis, onchocerciasis, schistosomiasis, and periodontal disease.

In another embodiment, the disclosure provides methods to remove free heme from the stored blood, comprising contacting the stored blood with an NCR247 peptide, derivative, variant, homolog, or enantiomer thereof. In one embodiment, the disclosure provides methods for treating a subject in need of a blood transfusion, comprising prior to administering the blood transfusion, contacting the blood to be administered with an NCR247 peptide, derivative, variant, homolog, or enantiomer thereof. In a further embodiment, the disclosure provides medical devices comprising an NCR247 peptide, derivative, variant, homolog, or enantiomer thereof, coated on a surface of the medical device.

P=0.0035, *P=0.0002 and ****P<0.0001 vs untreated sample; two-way analysis of variance (ANOVA) with multiple comparisons.

Figure 2:
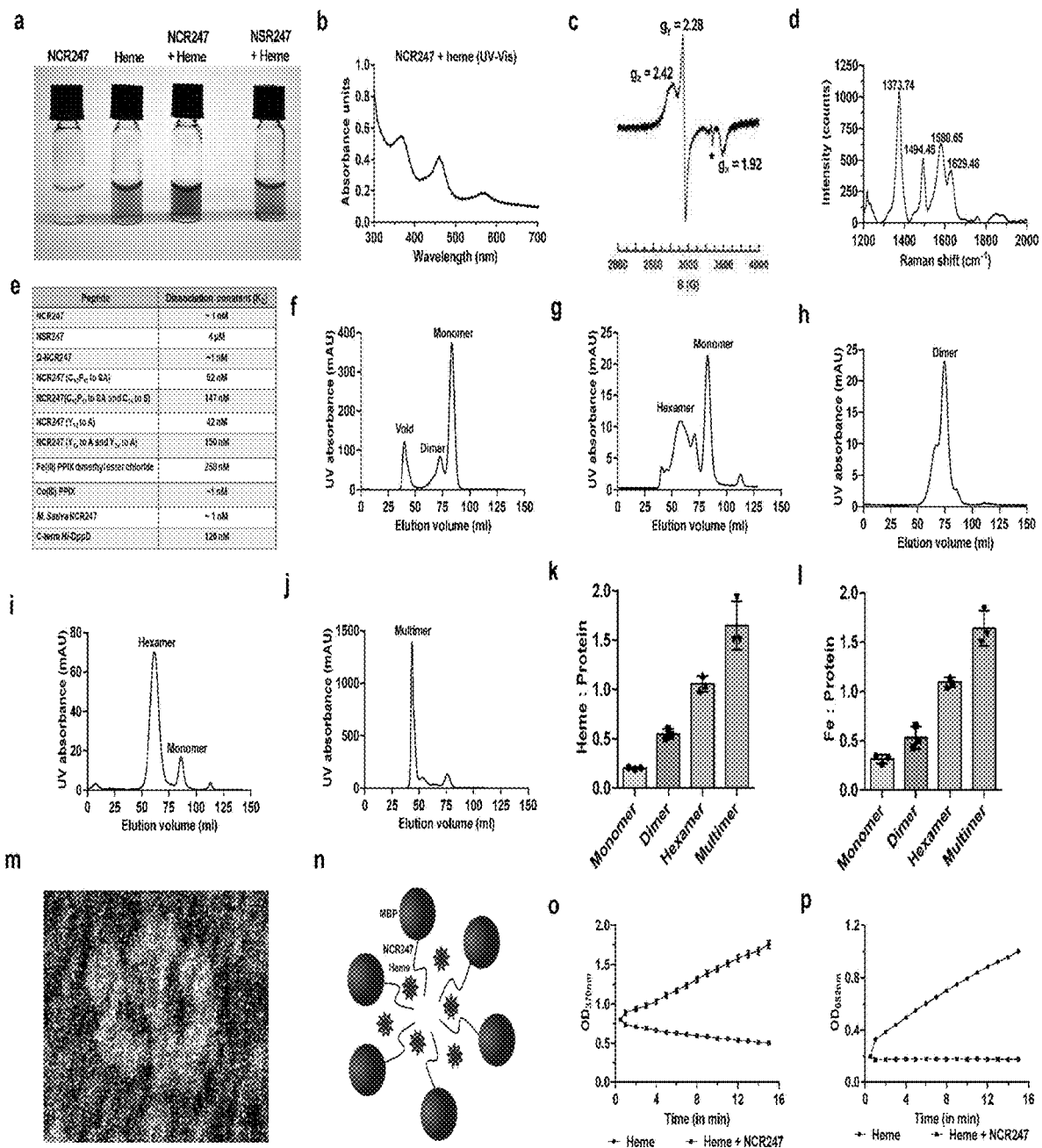

FIG. 2. NCR247 binds and sequester heme. a, Chemically synthesized NCR247 shows reddish-brown color upon heme binding. NSR247 with heme shows no color change. b, UV-Vis spectrum of heme bound NCR247 with split-Soret peaks at 366 nm, ~450 nm, and 560 nm. c, EPR spectrum of NCR247-heme complex showing rhombic signal with g values indicating a low spin ferric heme. *shows an imperfection in the cavity. d, Resonance-Raman spectrum of NCR247-heme complex with prominent v peaks indicative of a $Fe^{3+}$, six-coordinate, low spin (6cLS) b-type heme. e, Dissociation constant ($K_D$) of NCR247 and variants to heme as determined from Biolayer interferometry using biotinylated heme as ligand. For Fe(III) PPIX dimethyl ester Cl and Co(III) PPIX, biotinylated NCR247 was used as ligand. f and g, Size-Exclusion chromatograms of native MBP-NCR247 from *E. coli* grown without ALA (predominant monomer) (f), and with ALA (mixed multimers) (g). h-j, Size-Exclusion chromatograms after addition of half molar equivalent (predominant dimer) (h), equimolar (predominant hexamer) (i), and excess (predominant multimer) (j) heme to the purified monomer fraction of MBP-NCR247. k and l, Heme content (Heme assay kit) (k), and iron content (ICP-MS analysis) (l) of fractions isolated from size exclusion chromatography. m, Representative negative staining image of the hexamer fraction of MBP-NCR247. n, Current model for heme sequestration by NCR247. o and p, Peroxidase activity of heme and NCR247-heme complex on a chromogenic substrate TMB, measured by absorption at 370 nm (o) and 652 nm (p). In a-j, representative data from three independent experiments is shown. In k, l, o and p, data are presented as mean of three replicates ±s.d.

Figure 3:
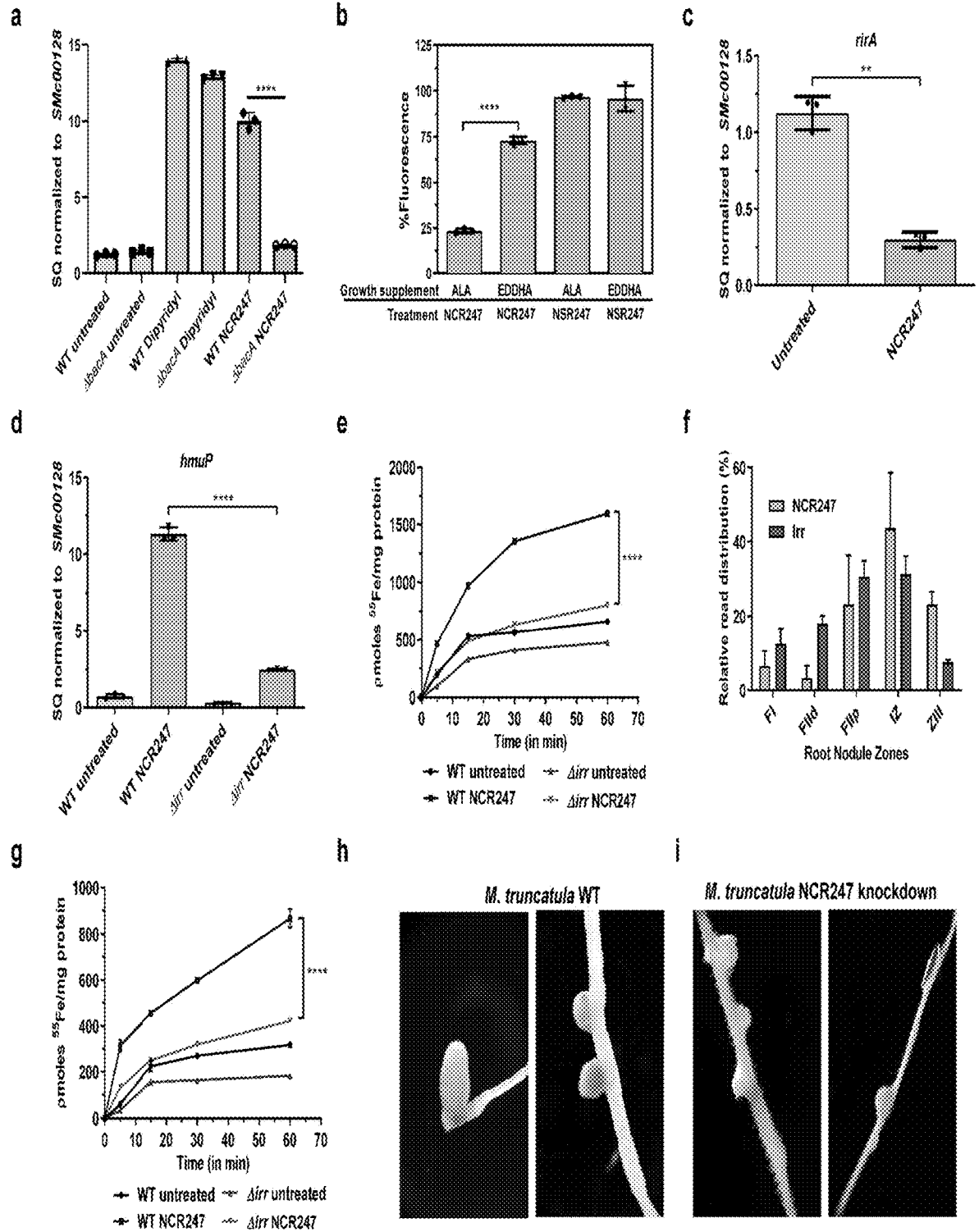

FIG. 3. NCR247 binds intracellular heme and drives iron uptake by modulating Irr mediated iron regulation. a, Diminished expression of gene involved in iron uptake (hmuP) in NCR247 treated ΔibacA compared to NCR247 treated wildtype and iron chelator (dipyridyl) treated wildtype and ΔibacA strain as measured by qRT-PCR analysis. b, Increased quenching of fluorescence of N-FITC labeled NCR247 by cellular extracts from *S. meliloti* grown with ALA when compared to *S. meliloti* grown with EDDHA. N-FITC labeled NSR247 is used as a control. c, Decrease in expression of rirA upon treatment with NCR247 as measured by qRT-PCR analysis d, Decrease in expression of hmuP in NCR247 treated Δirr when compared to NCR247 treated wildtype *S. meliloti*. In a, c and d, 2 μM NCR247 was treated for 30 mins and the data are expressed as starting quantities (SQ) of respective mRNAs normalized to the control gene SMc00128 and are presented as average of three technical replicates ±s.d. e, Decreased uptake of $^{55}$Fe in NCR247 treated Δirr when compared to NCR247 treated Wildtype *S. meliloti*. f, Relative expression levels of NCR247 and irr along the symbiotic process represented by distinct nodule sections. NCR247 and irr are expressed at higher levels in the interzone (IZ) where bacteroids are differentiating and preparing for nitrogen fixation. FI-meristematic zone, FIId (distal), FIIp (proximal fraction) of Zone II-infection and differentiation zone, ZIII-nitrogen fixation zone. Data is obtained from Symbimics website curated from previous publication and represents a mean of three technical replicates[80]. The individual data points are not available. g, Decreased uptake of $^{55}$Fe in NCR247 treated bacteroids from nodules of inoculated with Δirr when compared to NCR247 treated bacteroids from wildtype *S. meliloti* inoculated plants. h and i, Representative image of 12-day nodules of Wildtype (h) and NCR247 knockdown (1) of *M. truncatula* (A17) inoculated with wildtype S. melitoi (Rm1021). In b, e and g, data are presented as mean of three biological replicates ±s.d. In b, **P<0.0001 EDDHA vs ALA treated sample; c, P=0.001 NCR247 Vs Untreated sample; a, d, e and g, ****P<0.0001 NCR247 treated WT vs ΔbacA/Δirr samples; two-way analysis of variance (ANOVA) with multiple comparisons. In h-i, representative image from 8 roots with each genotype is shown.

Figure 4:
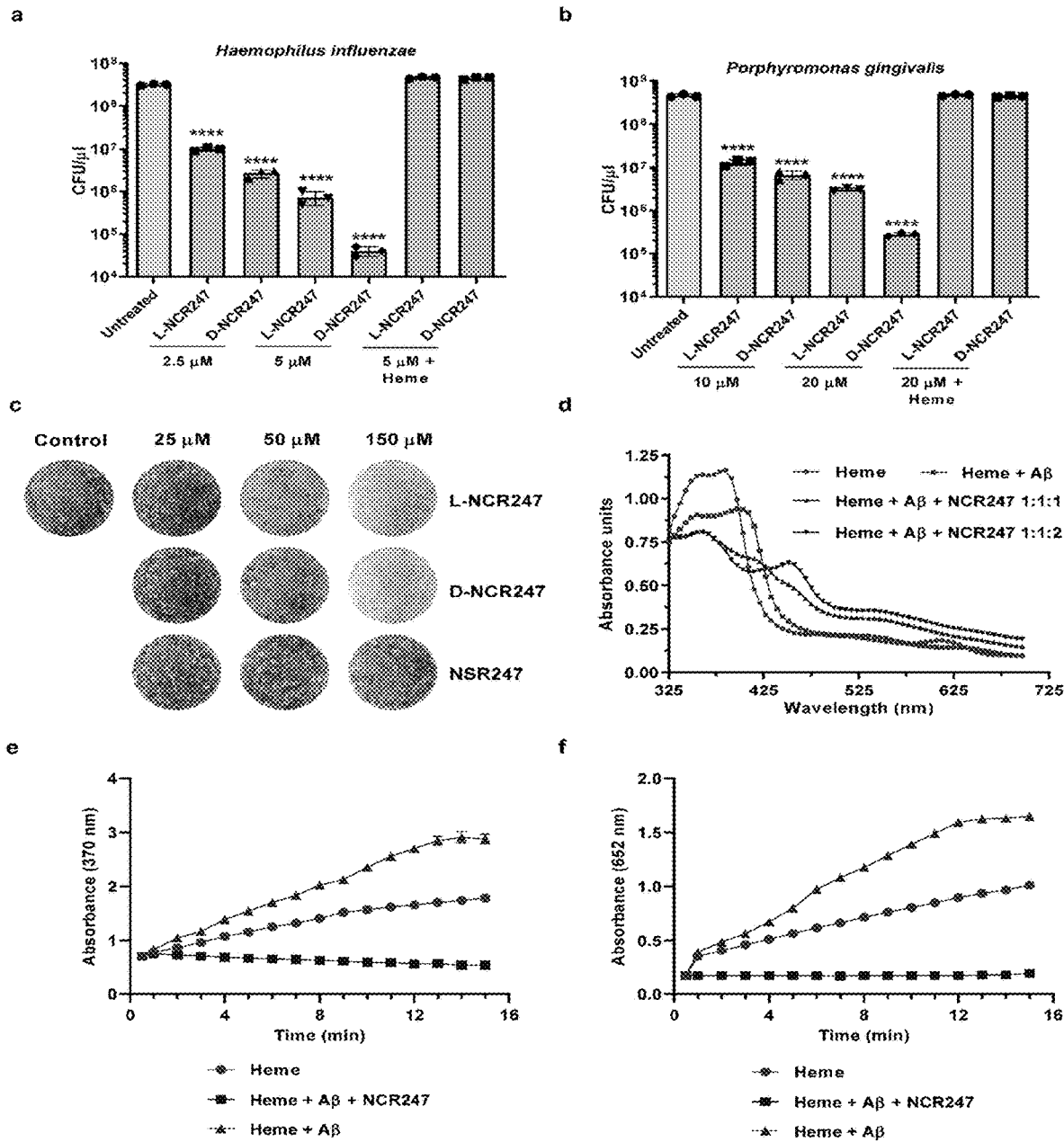

FIG. 4. Potential therapeutic applications of NCR247-heme binding. a and b, Reduction of viable cell number of *Haemophilus influenzae* (a) and *Porphyromonas gingivalis* (b) upon treatment with increasing concentrations of L and D-NCR247. c, Images of crystal-violet stained fibroblast monolayers with plaques formed by the parasite *Toxoplasma gondii* pre-treated with L-NCR247, D-NCR247, or L-NSR247. d, UV-Vis spectrum of Amyloid Beta(Aβ) peptide-heme complex (1:1), Aβ:heme complex with equimolar NCR247(1:1:1) (* indicates an intermediary peak formed at 420 nm) and Aβ-heme complex with excess NCR247 (1:1: 2),  represents the appearance of typical NCR247-heme complex peaks at 366 nm and 450 nm. e and f, Peroxidase activity of Heme, Aβ-heme complex and NCR247+Aβ-heme complex on a chromogenic substrate TMB as measured by absorption at 370 nm (e) and 652 nm (f). c and d, Representative image from two independent replicates. In a, b and e, data are presented as mean of three independent replicates ±s.d. In a and b **P<0.0001 vs untreated sample; two-way analysis of variance (ANOVA) with multiple comparisons.

Figure 5:
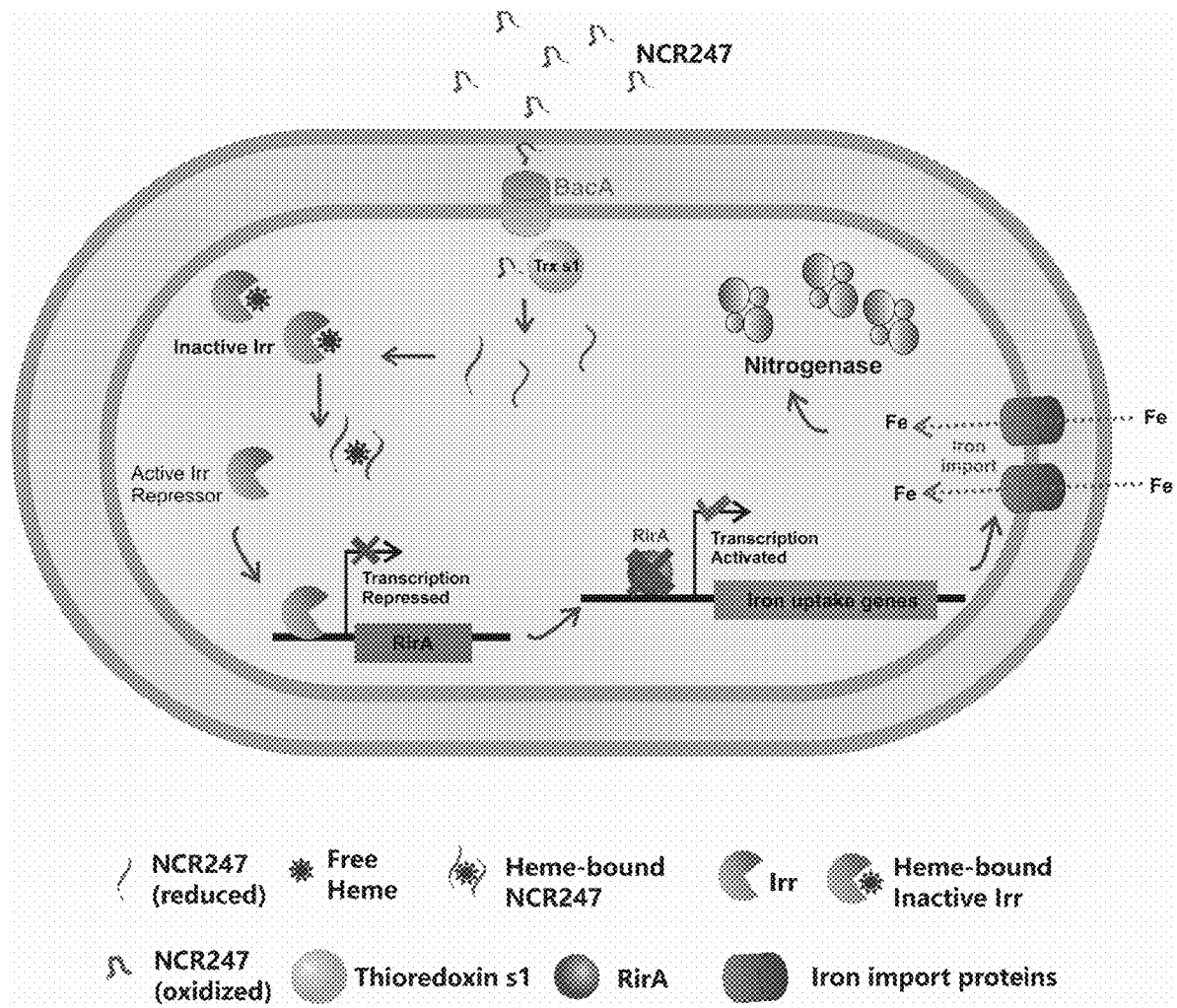

FIG. 5. NCR247 sequesters heme and overrides bacterial iron regulation to aid in symbiosis. Model for the proposed role of NCR247 in iron regulation of bacteria and symbiosis. NCR247 secreted by the *Medicago* plant enters the cytoplasm of *S. meliloti* through the inner membrane protein BacA. NCR247 could be then reduced by plant produced Thioredoxin sl. Reduced NCR247 sequesters heme tightly. This leads to unavailability of heme and stabilization of heme regulated transcriptional repressor Irr even under iron sufficient conditions. Active Irr represses rirA. RirA is a transcriptional repressor of iron uptake genes. This leads to an increase in transcription of iron uptake genes and ultimately results in an increase in iron import into the cell. The need for iron in nodule increases during nitrogen fixation and nitrogenase (the key nitrogen fixing enzyme) requires numerous iron atoms structurally and functionally. Thus, NCR247 mediated boost in iron import could improve nitrogen fixation to ultimately benefit the plant.

Figure 6:
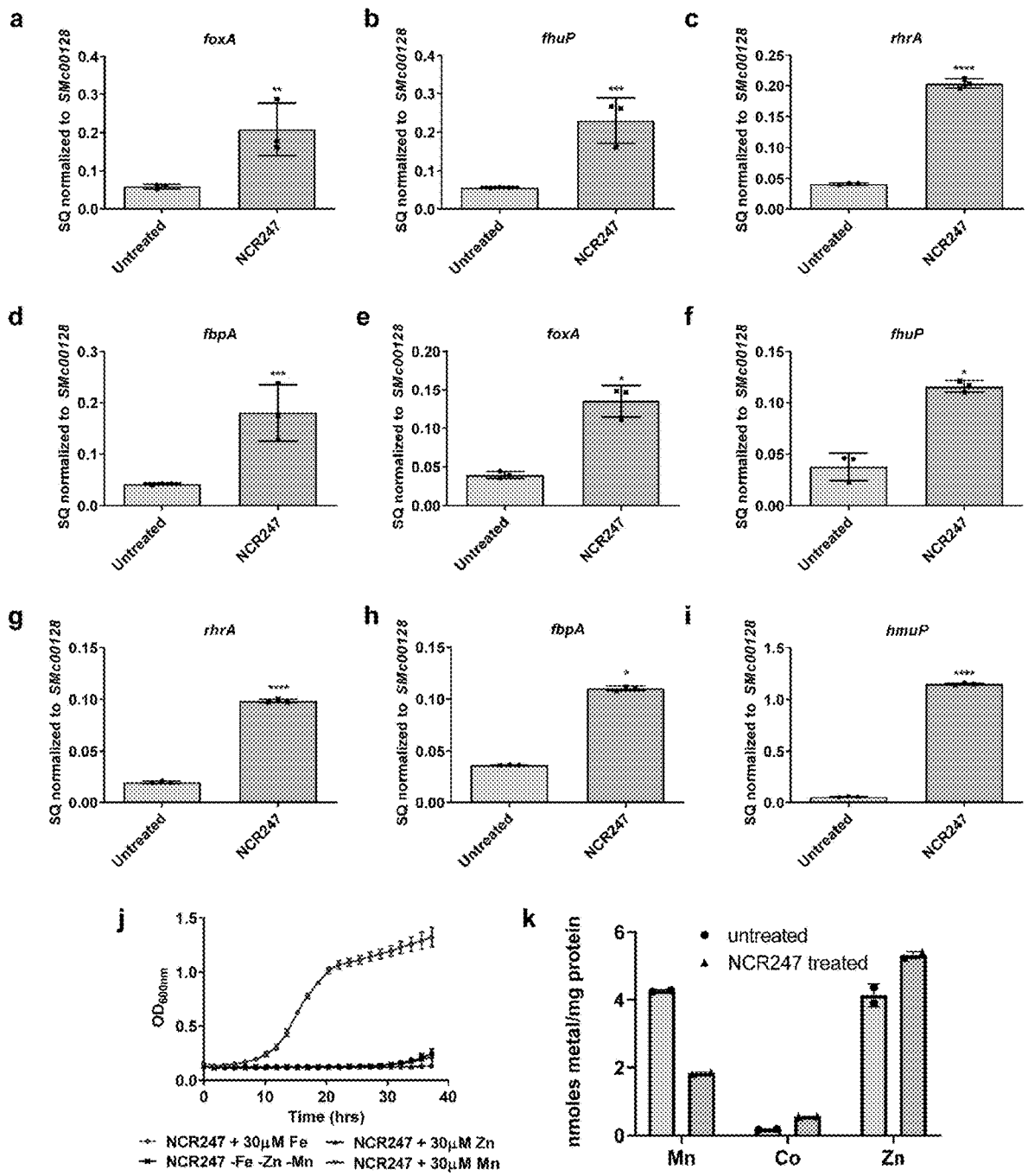

FIG. 6. NCR247 treatment induces an increase in expression of iron uptake genes. a-d, qRT PCR analysis shows an increase in expression of genes involved in iron uptake (foxA (a), fhuP (b), rhrA (c), and fbpA (d)) upon treatment with 2 μM NCR247 for 30 mins. Cells were grown in iron sufficient medium (5 μM) e-i, qRT PCR analysis show increase in transcript levels of genes involved in iron uptake (hmup (e), foxA (f), fhup (g), rhrA (h) and fbpA (i)) when grown in iron-replete medium (30 μM) upon NCR247 treatment for 30 mins. In a-i, the data are expressed as starting quantities (SQ) of respective mRNAs normalized to the control gene SMc00128 and are presented as average of three technical replicates ±s.d. j, Growth pattern of 2 μM NCR247 treated cells when grown in minimal medium lacking Fe, Mn, and Zn or medium supplemented with 30 μM of either $FeSO_4$, $MnCl_2$ or $ZnSO_4$. Data are presented as mean of three biological replicates ±s.d. k, Absence of increase in Mn, Co and Zn content of 2 μM NCR247 treated *S. meliloti* when compared to untreated cells as measured by ICPMS analysis. In a-j, * P<0.01, P<0.01, *P<0.001 and ****P<0.0001 vs untreated sample; two-way analysis of variance (ANOVA) with multiple comparisons.

Figure 7:
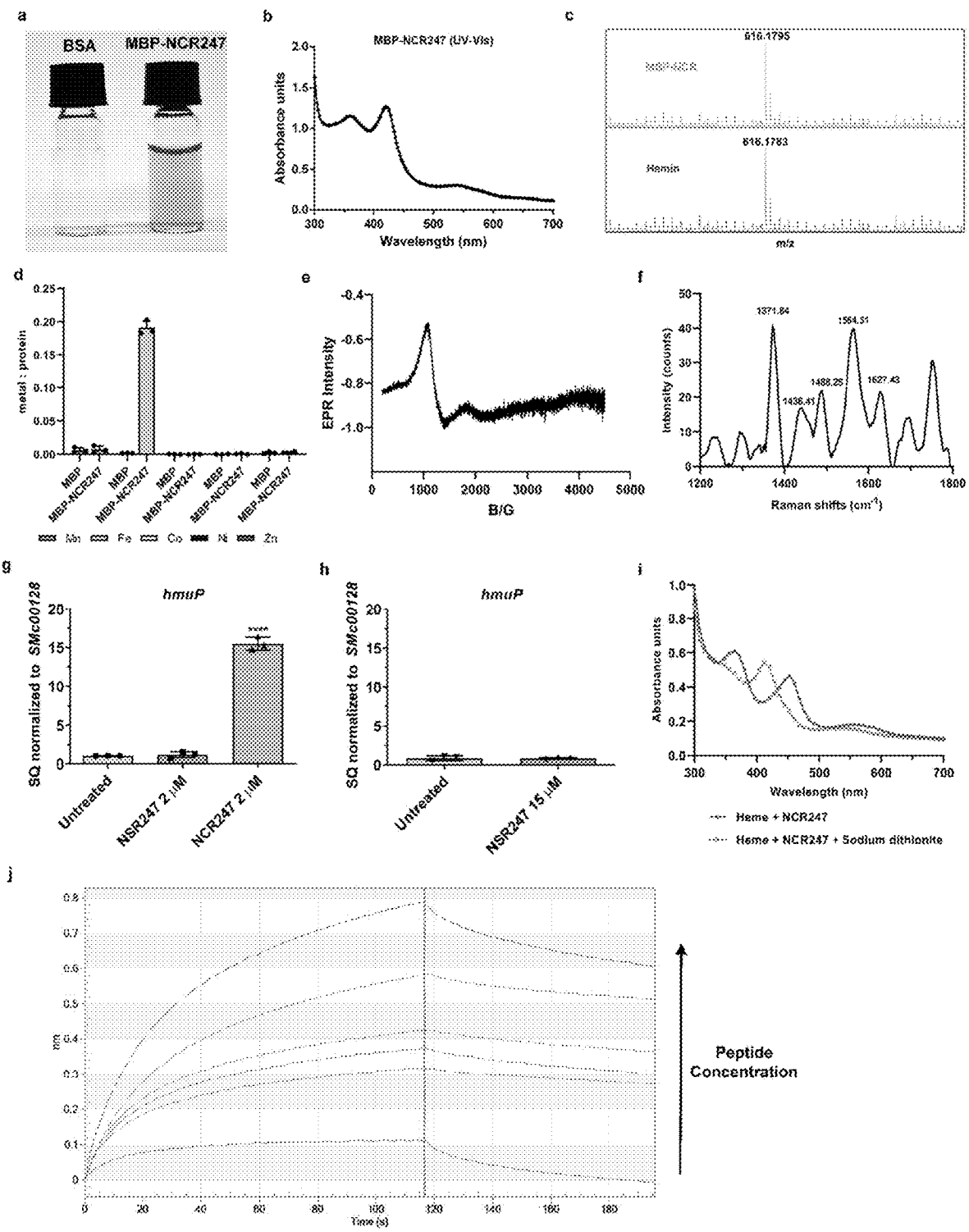

FIG. 7. NCR247 binds heme and NSR247 lacks heme binding ability. a, Purified MBP-NCR247 is a reddish colored protein. b, UV-Vis spectra of MBP-NCR247 showing peaks at 362 nm, 418 nm, and 540 nm with a slight shoulder at 580 nm. c, LC-MS spectrum from MBP-NCR247 (top) when compared to heme standard (Bottom). d, Metal content of purified MBP and MBP-NCR247 (measured using ICPMS analysis) showing the presence of iron and absence of any other metal. Data are presented as mean of three biological replicates ±s.d. e, EPR spectrum of NSR247 with heme (g values=5.56) indicating a high spin ferric heme (spectrum similar to free heme). f, Resonance-Raman spectrum of NSR247 with heme shows prominent v peaks indicative of a $Fe^{3+}$, five-coordinate, high spin (5cHS) b-type heme. g and h, Lack of change in expression of iron uptake gene (hmuP) upon treatment with 2 μM(g) or 15 (h) NSR247. Data are expressed as starting quantities (SQ) of respective mRNAs normalized to the control gene SMc00128 and are presented as average of three technical replicates ±s.d. i, UV-Vis spectra of NCR247-Ferrous heme complex, after reduction by excess Sodium dithionite in an anaerobic chamber, indicating peaks at 420 nm and 550 nm. j, Representative raw image of association and dissociation steps in an Octet bio-layer interferometry experiment (detailed in methods). Biotinylated heme was used as ligand and NCR247 was used as analyte. In a, b, c, e, f, and i, representative data from three independent experiments is shown.

Figure 8:
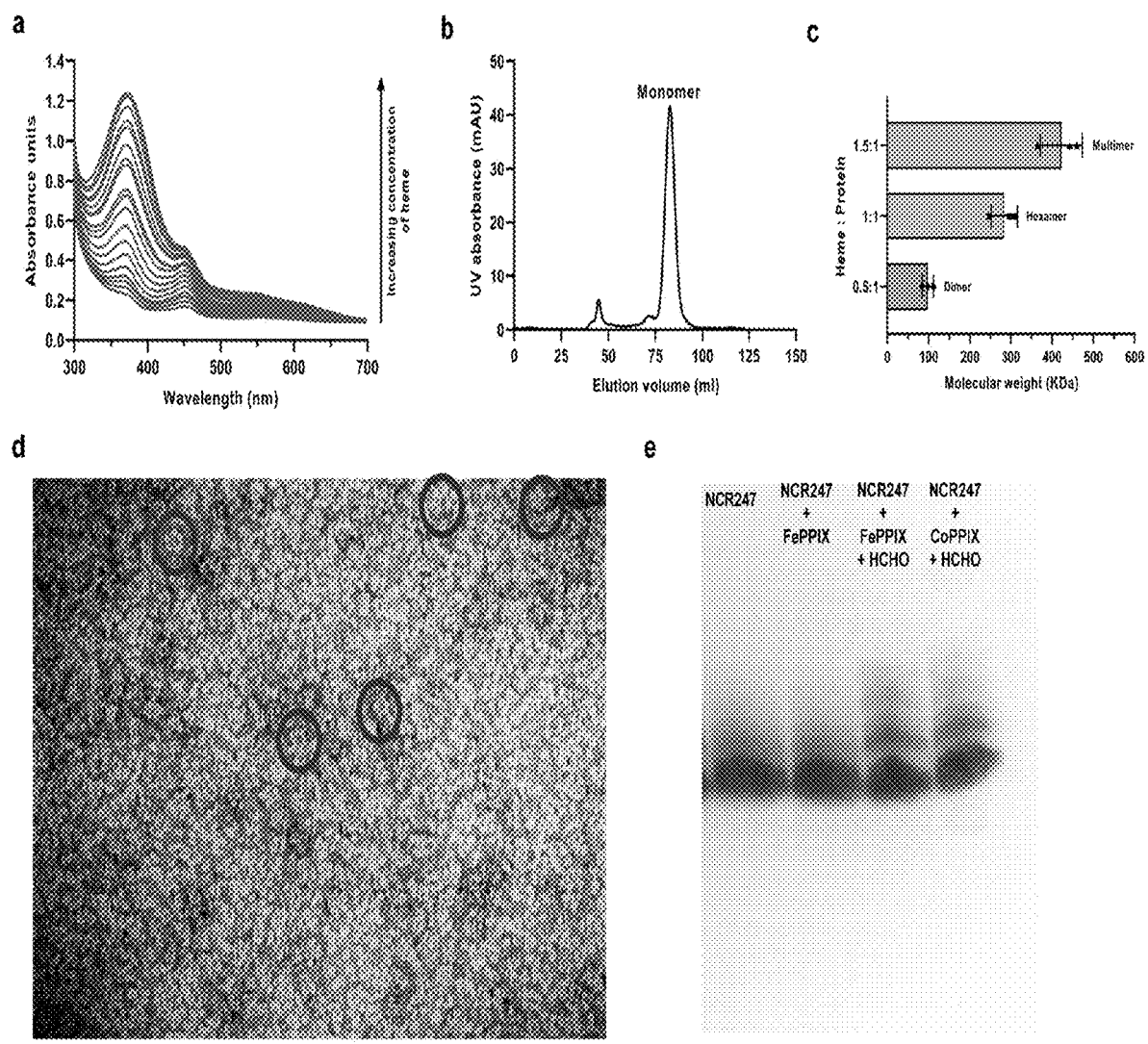

FIG. 8. Heme induced multimerization of NCR247. a, UV-Vis spectrum of NCR247-heme complex upon addition of increasing concentrations of heme (0.2 to 20 molar equivalents). Peak at 366 nm visibly increases in height even after peaks at 450 nm and 580 nm are saturated. b, Size-exclusion chromatogram of native MBP-NSR247 from E. coli grown with ALA (predominant monomer) c, Mass photometry analysis indicating the average molecular weight of the species that existed after addition of half molar equivalent, equimolar, and excess heme to the monomer fraction of purified MBP-NCR247. Data are presented as mean of three independent replicates ±s.d. d, Whole view of the grid used for negative staining made from the hexameric fraction of purified MBP-NCR247 showing multiple daisy like species. e, Tris tricine SDS gel showing multimerization of NCR247 peptide upon addition of heme (FePPIX) and CoPPIX and crosslinking with formaldehyde. In a and b, representative data from three independent experiments is shown.

Figure 9:
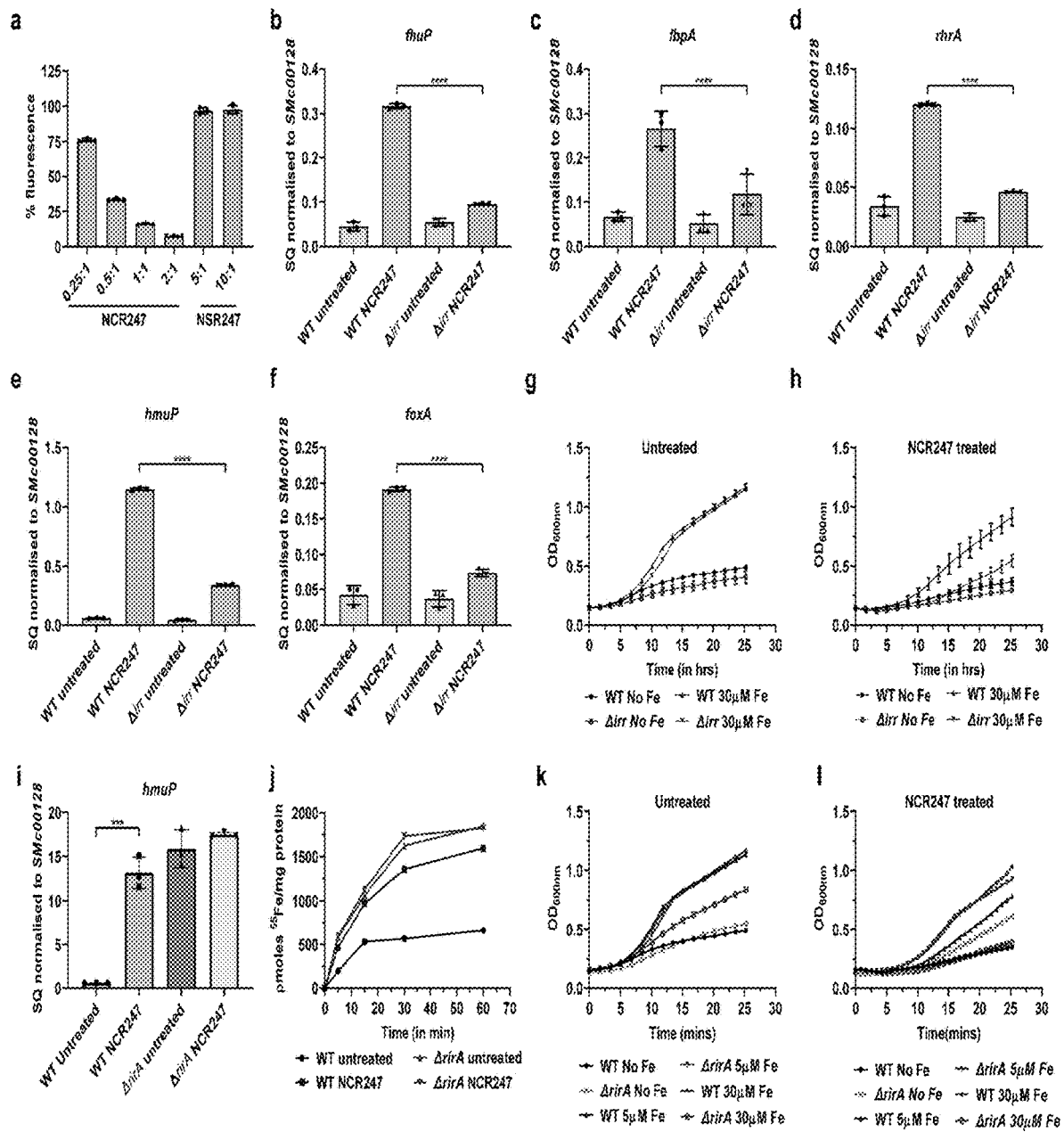

FIG. 9. NCR247 drives iron uptake by controlling Irr mediated iron regulation. a, Fluorescence of FITC-NCR247 quenched by increasing concentrations of heme. Fluorescence of FITC-NSR247 remains unquenched even after addition of excess heme. b-f, Decrease in expression of genes involved in iron uptake (fhuP (b), fbpA (c), rhrA (d), hmuP (e), foxA (f)) in a 2 μM NCR247 treated Δirr when compared to NCR247 treated wild type S. meliloti, when grown in iron-replete medium (30 NCR247 was treated for 30 mins g and h, Growth pattern of untreated (g) and NCR247 treated (h) wildtype and Δirr cells in iron-depleted (—Fe) and iron-replete media (30 μM). i, Derepressed expression of hmup in an untreated ΔrirA when compared to wildtype S. meliloti as measured by qRT-PCR analysis. j, Increased uptake of $^{55}$Fe in untreated ΔrirA when compared to untreated and NCR247 treated wildtype S. meliloti. k and l, Growth pattern of untreated (k) and NCR247 treated (l) wildtype and ΔrirA cells in iron-depleted (—Fe), iron sufficient (5 μM) and iron-replete media (30 In a, g, h, j, k and l data are presented as mean of three independent replicates ±s.d. In b-f and i, The data are expressed as starting quantities (SQ) of respective mRNAs normalized to the control gene SMc00128 and are presented as average of three technical replicates ±s.d. In b-f, **P<0.0001 NCR247 treated WT vs Δirr—samples; In i, *P<0.0001 WT untreated vs WT NCR247 treated; two-way analysis of variance (ANOVA) with multiple comparisons.

Figure 10:
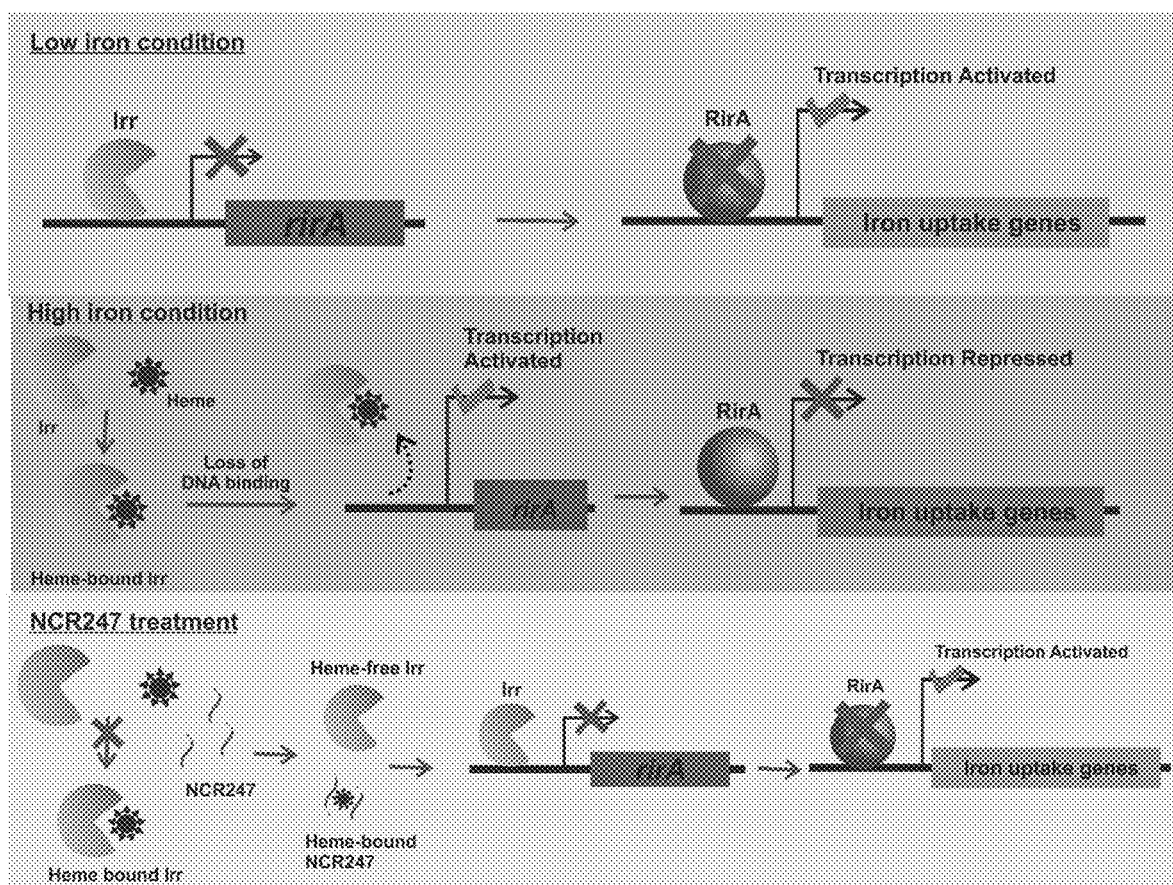

FIG. 10. Model of regulation of iron metabolism by Irr and RirA in S. meliloti and proposed mechanism of action of NCR247. In S. meliloti regulation of iron status is controlled by two anti-parallel regulators Irr and RirA. Both Irr and RirA bind to DNA elements upstream of genes and repress gene expression. However, Irr senses iron status through heme[80] (Irr loses DNA binding ability upon heme binding[22]) and RirA through Fe—S cluster formation (functional Fe—S cluster binding on RirA is needed for RirA to bind DNA[23]). During low intracellular iron concentrations, due to low intracellular heme availability, Irr remains stable and represses genes involved in iron storage, iron export, and also rirA[19]. Hence, in this condition, the expression of rirA is lowered and the availability of Fe—S cluster is scarce. This lack of RirA leads to an increase in expression of iron uptake genes. At high iron concentration, heme is available to bind Irr and this leads to the inability of Irr to bind DNA for repression. This leads to an increase in transcription of rirA and repression by RirA leads to a decrease in expression of iron uptake genes to prevent further iron uptake. When NCR247 is present during these conditions, it sequesters heme and hence heme is not available to inactivate Irr mediated repression. This leads to unusual availability of active Irr and repression of rirA. This leads to activation of iron uptake genes. Thus, NCR247 treatment leads to an iron starvation response and increase in import of iron even during iron sufficient and replete conditions.

Figure 11:
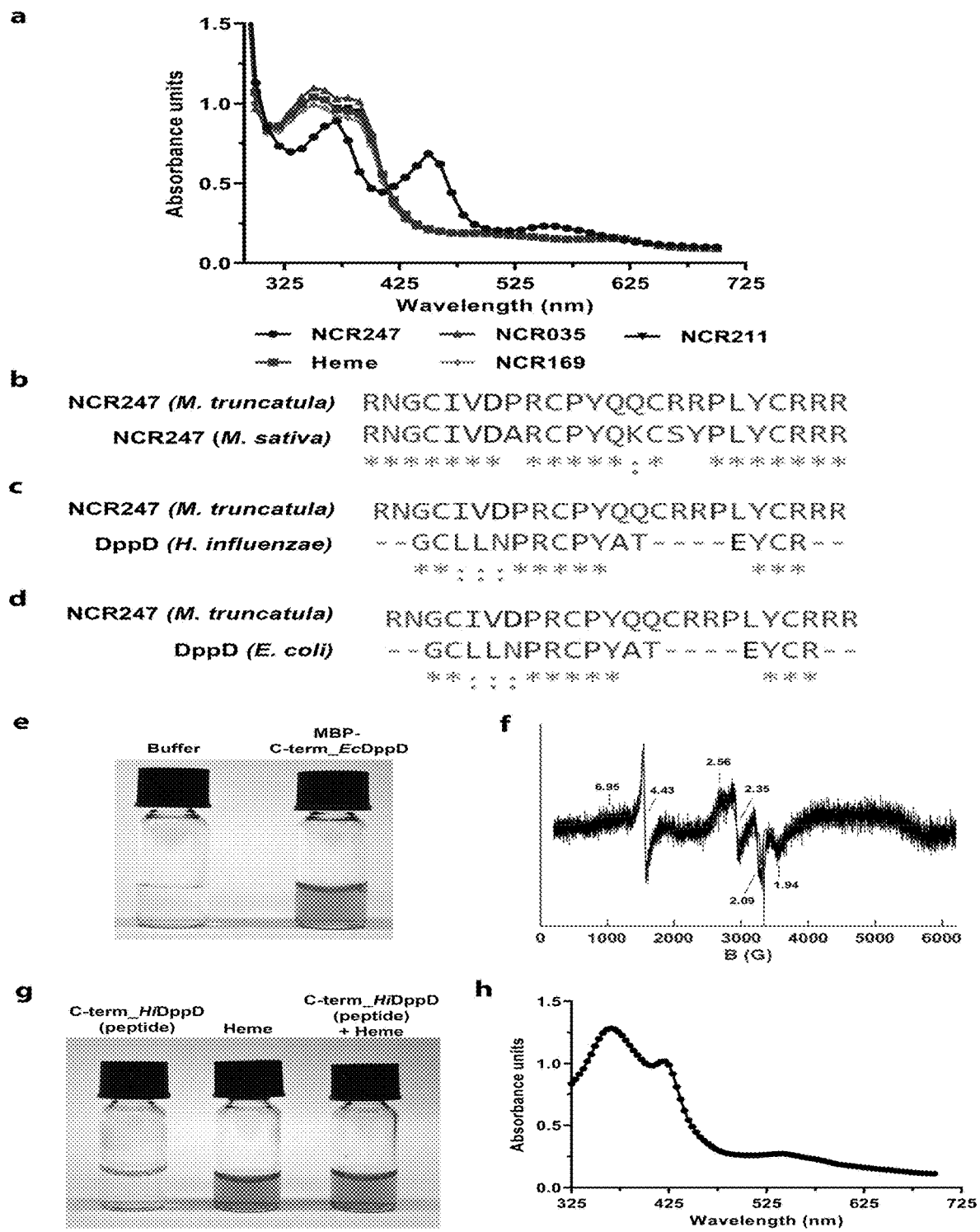

FIG. 11. Sequences similar to NCR247. Sequences similar to NCR247. a, UV-Vis spectrum of NCR peptides (NCR169, NCR035, NCR211, and NCR247) with heme indicating that only NCR247 shows a spectrum characteristic of heme binding proteins. b, Sequence alignment of NCR247 from the plants M. sativa and M. truncatula (top SEQ ID NO: 1, and bottom SEQ ID NO: 5). c and d, Sequence alignment of NCR247 from M. truncatula and C-terminal region of DppD (protein involved in heme transport) of Hemophilus influenzae top SEQ ID NO: 1, and bottom SEQ ID NO: 13) (c) and E. coli (d) top SEQ ID NO: 1, and bottom SEQ ID NO: 14). In b, c, and d, alignments were performed using CLUSTAL Omega. NCR247 from Meidcago sativa and C-terminal end of DppD were significantly similar sequences with a e-value less than 5 obtained in a BLAST search. e and f, Sequence similar to NCR247 from C-terminal end of DppD of E. coli, tagged to MBP purifies as a reddish colored protein (e) and shows EPR spectrum (mixture of high and low spin heme) similar to other heme binding proteins[81] g and h, Chemically synthesized peptide with sequence similar to NCR247 from C-terminal end of DppD of H. influenzae shows reddish color upon binding heme (g) and exhibits a UV-Vis spectrum (366 nm, 427 nm, and 540 nm) characteristic of heme binding proteins (h). In a and e-h representative data from three independent experiments is shown.

Figure 12:
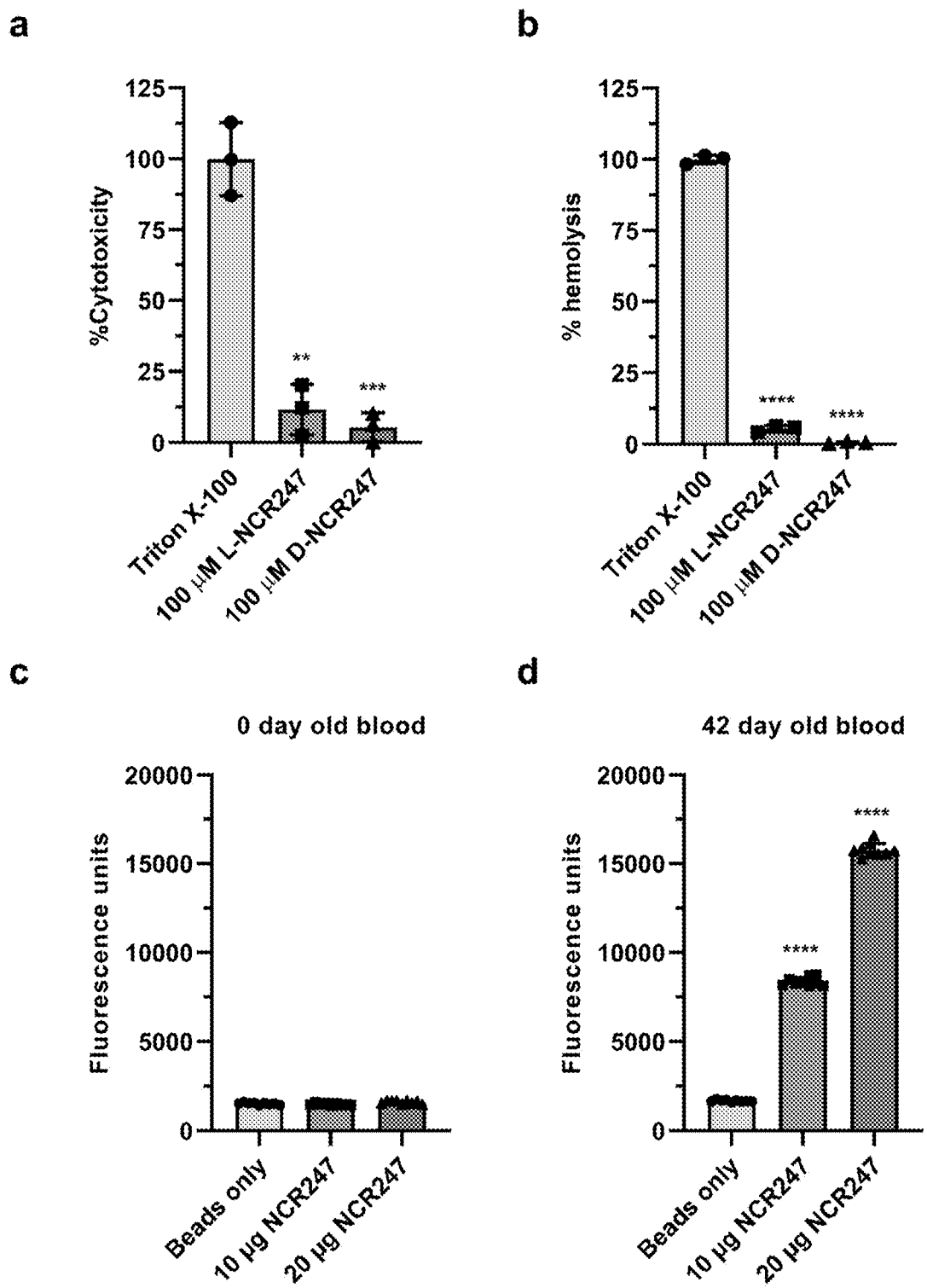

FIG. 12. NCR247 suitability for potential therapeutic applications. a, Standard cytotoxicity assay (Methods) on HEK293 cell line indicates negligible hemolysis by L and D-NCR247. b, Standard hemolysis assay (Methods) on hRBC indicates negligible hemolysis by L and D-NCR247. In a and b, Triton X-100 was used as a positive lysis control and data was normalized to PBS blank. Data are presented as mean of three independent replicates ±s.d. c and d, Pull down of heme by biotinylated NCR247 from 0-day old (c) and 42-day old plasma (d). Oxalic acid assay was used to measure the total heme content of the pull-down. Data are presented as mean of three independent replicates (with three technical replicates for each) ±s.d. In a, b, P<0.01, *P<0.001 vs TritonX-100 treated sample and in d, and ****P<0.0001 vs beads only; two-way analysis of variance (ANOVA) with multiple comparisons.

Figure 13:
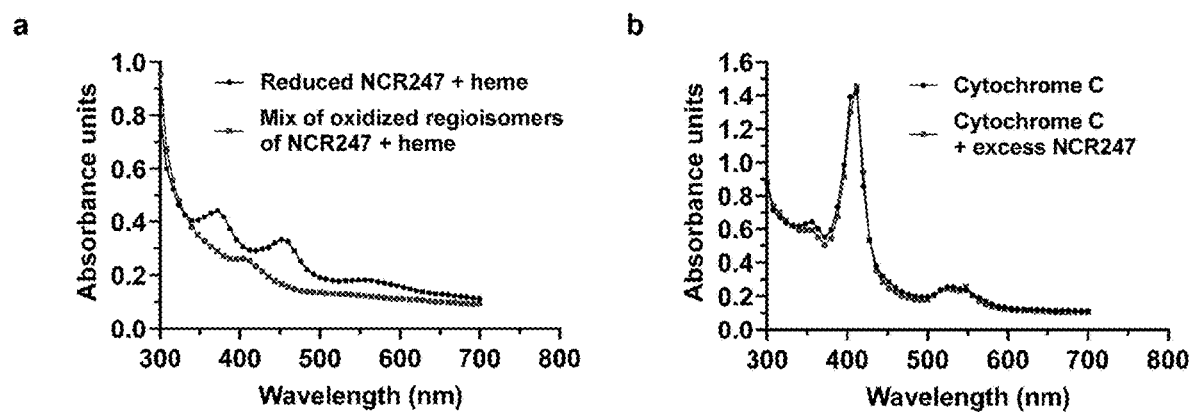

FIG. 13. Possibilities of NCR247 sequestering heme from hemoproteins in planta. a, UV-Vis spectrum showing poor interaction of oxidized regioisomers of NCR247 and a presence of minor Soret band with heme when compared to reduced NCR247. b, UV-Vis spectrum showing inability of NCR247 to sequester heme from Cytochrome c. The absorption spectrum of Cytochrome c remains unaltered even after addition of excess NCR247.

Figure 14:
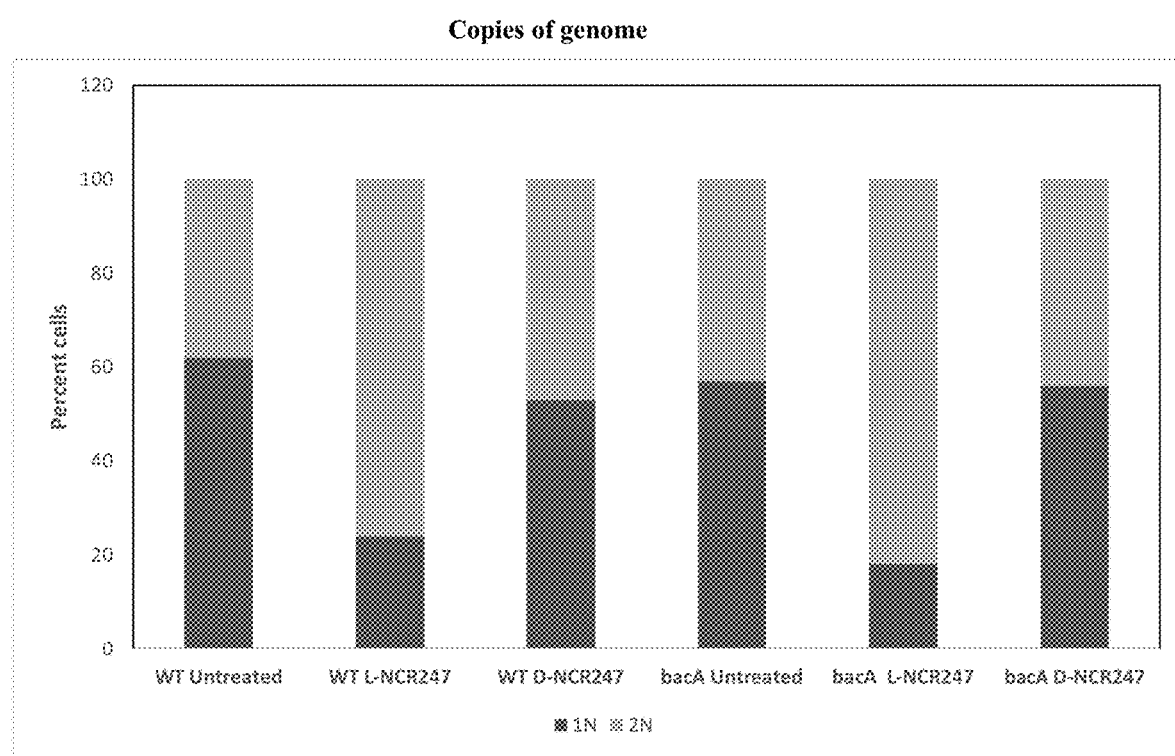

FIG. 14. Data showing D-NCR247 does not inhibit cell division like L-NCR247. Cell cycle progression analysis using flow cytometry on synchronized cultures of Wild type S. meliloti and bacA mutant of S. meliloti treated with L or D-NCR247 when compared to untreated cells. Dark grey represents percentage of cells with 1 copy of genome and light grey represents percentage of cells with 2 copies of genomes. L-NCR247 treated cells has more percentage of cells having 2 copies of genome indicating lack of cell division. Data are presented as average of three biological replicates.

Figure 15:
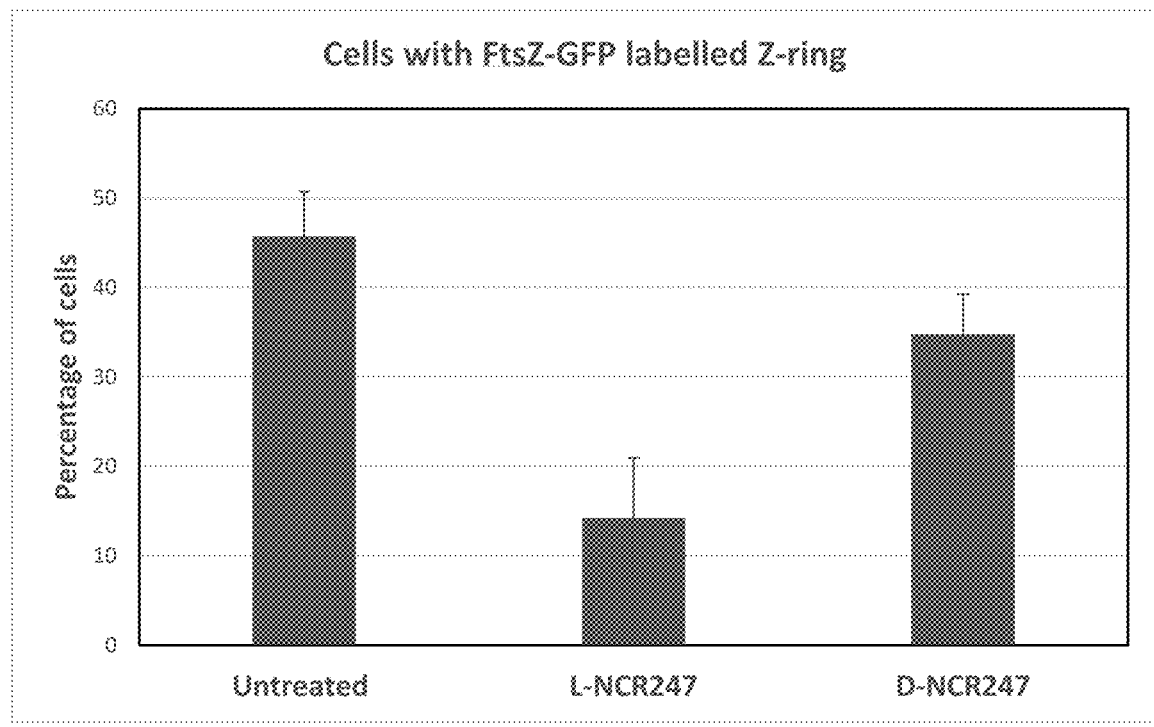

FIG. 15. Data showing D-NCR247 does not inhibit formation of Z-ring like L-NCR247. Visualization of Z-ring formation during cell division by FtsZ-GFP labeled cells using fluorescent microscopy. Data indicates percentage of cells displaying fully formed Z-rings when synchronized and treated with upon treatment with 2 µM of L or D-NCR247 for 200 mins. Percentage of cells forming Z-ring is greatly reduced when treated with L-NCR247. Data are presented as average of three biological replicates ±s.d.

Figure 16:
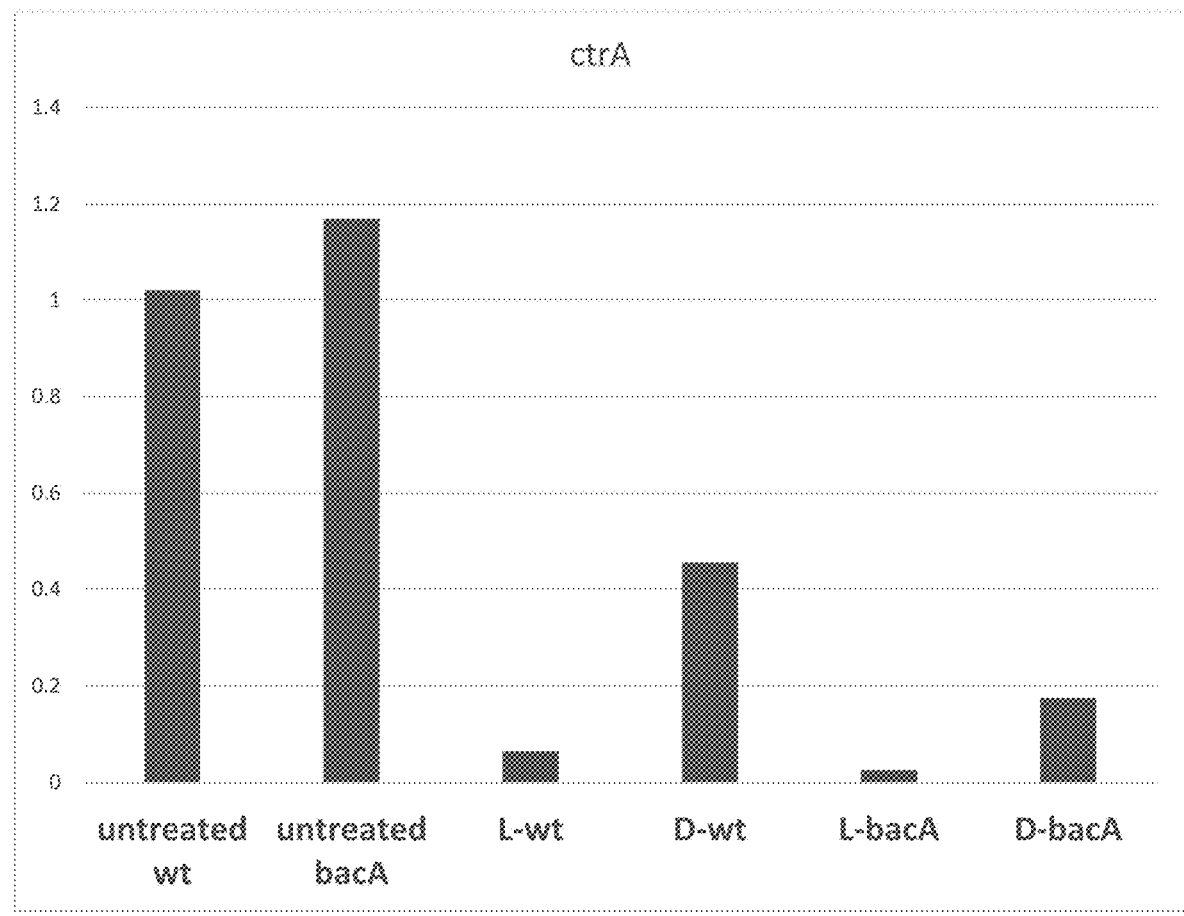
Figure 17A:
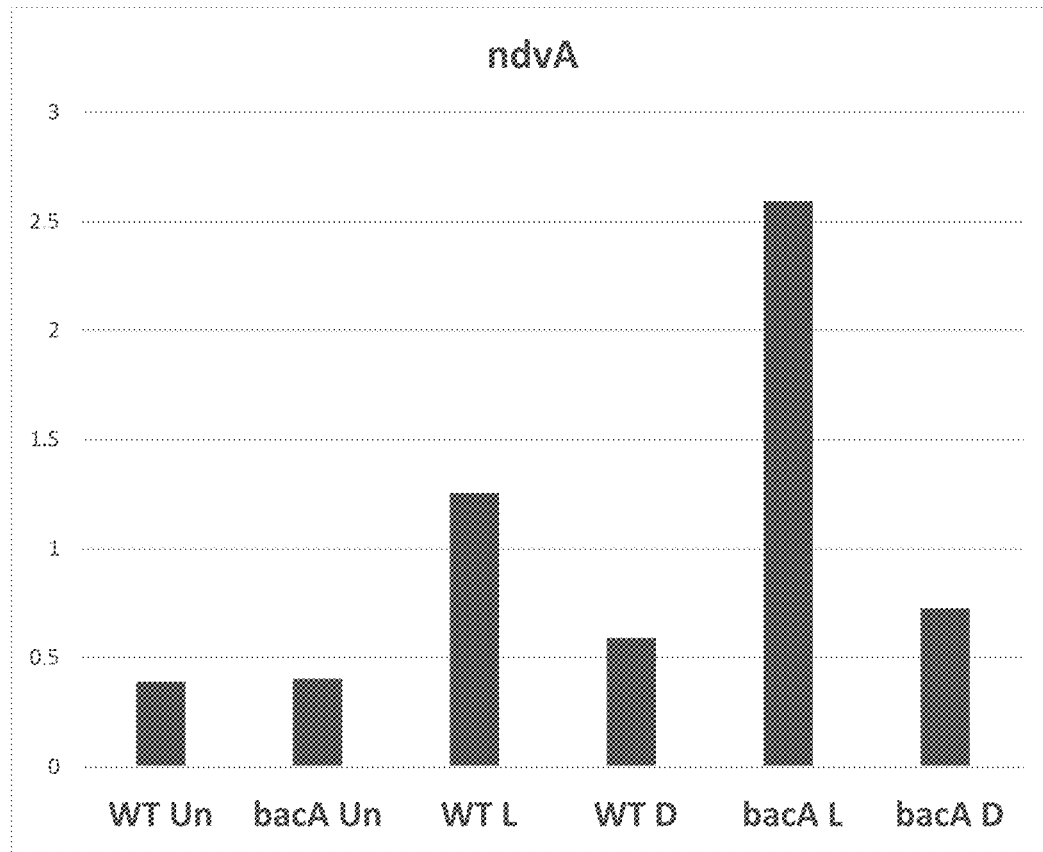
Figure 17B:
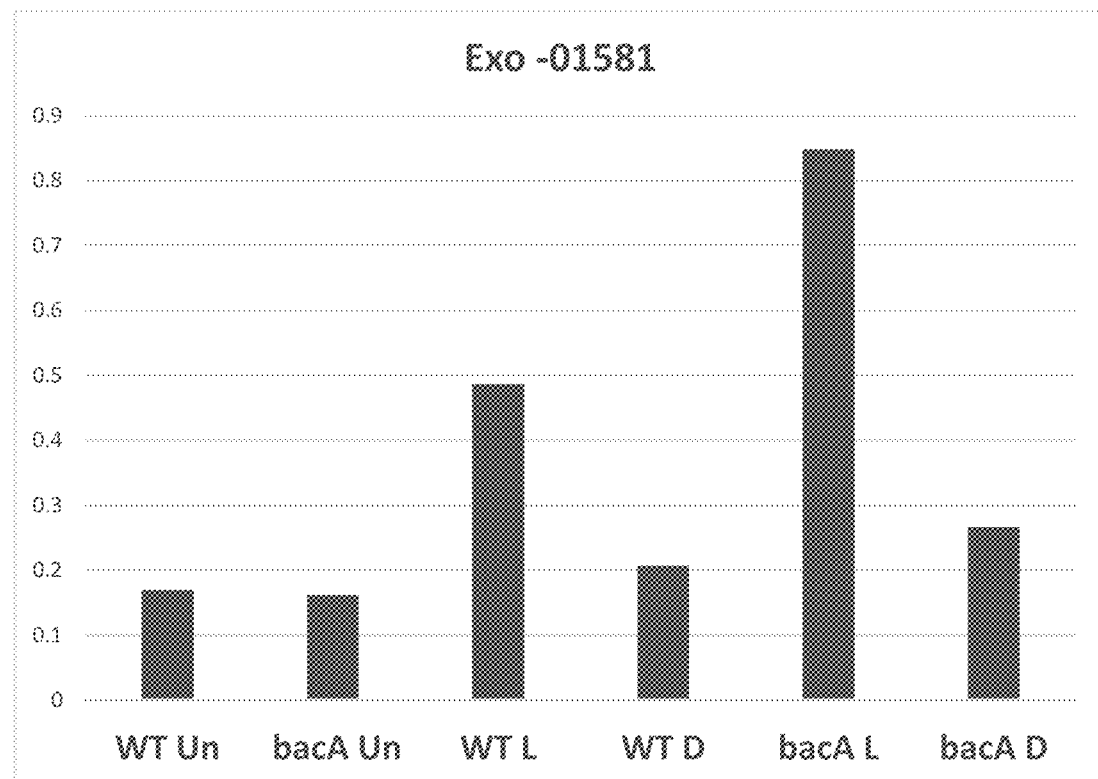

FIG. 16. Data showing D-NCR247 does not decrease the expression of CtrA like L-NCR247. qRT PCR analysis shows a decrease in expression of ctrA, which is the regulator of cell division upon treatment with 2 µM L-NCR247 for 30 mins. The decrease is less pronounced when treated with 2 µM D-NCR247. The data are expressed as starting quantities (SQ) of respective mRNAs normalized to the control gene SMc00128 and are presented as average of three technical replicates FIG. 17. Data showing D-NCR247 does not induce signal transduction through FeuP (A) and ExoS (B) like L-NCR247. qRT PCR analysis shows an increase in expression of ndvA ((A) a FeuP regulated gene), and SMc 01581 ((B) a ExoS regulated gene) which is the upon treatment with 2 µM L-NCR247 for 30 mins. The increase is less pronounced when treated with 2 µM D-NCR247. The data are expressed as starting quantities (SQ) of respective mRNAs normalized to the control gene SMc00128 and are presented as average of three technical replicates FIG. 18. NCR247 binds heme and this heme sequestration leads to an iron starvation response in S. meliloti and this happens in the cytoplasm since a bacA mutant is defective in inducing iron import genes. In vitro D-NCR247 is capable of binding heme equally well. A) qRT PCR analysis shows an increase in expression of hmuP (an heme import gene), upon treatment with 2 µM L-NCR247 for 30 mins. The increase is more pronounced when treated with 2 µM D-NCR247. The data are expressed as starting quantities (SQ) of respective mRNAs normalized to the control gene SMc00128 and are presented as average of three technical replicates. B) Increase in Fe content of 2 µM L-NCR247 treated S. meliloti when compared to untreated cells as measured by ICPMS analysis. 2 µM D-NCR247 shows a further increase in iron content. Data are presented as average of three technical replicates FIG. 19. Interaction of NCR247 with ribosomal machinery leads to modification in translational capability. (A) In-vitro translation assay to measure GFP production with increasing concentrations of L or D-NCR247. Fluorescence units decreased when treated with L-NCR247 indicating the reduction in production of GFP. (B) Western blot to measure the amount of GFP produced using Anti-GFP antibody. Indeed there was inhibition of production of GFP by L-NCR247 and but this effect was less pronounced in D-NCR247 treatment.

DETAILED DESCRIPTION

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX). As used herein, the singular forms "a", "an" and "the" include plural referents unless the context clearly dictates otherwise. As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), valine (Val; V), and norleucine (Nle, B). All embodiments of any aspect of the invention can be used in combination, unless the context clearly dictates otherwise.

In a first aspect, the disclosure provides peptides comprising or consisting of the amino acid sequence selected from the group consisting of SEQ ID NO:1-10, wherein 1 or more amino acid residues are D amino acids.

RNGCIVDPRCPYQQCRRPLYCRRR (SEQ ID NO:1) (also referred to herein as "NCR247"), RNGCIVDPRCPYQQCRRPLYC (SEQ ID NO:2) (NCR247 with the C-terminal 3 amino acids deleted), RNGCIVDPRCPYQQCRRPLYCXXX (SEQ ID NO:3), wherein X is any amino acid other than R (mutated NCR247), RNGCIVDPRCPYQQCRRPLYCAAA (SEQ ID NO:4) (mutated NCR247), RNGCIVDARCPYQKCSYPLYCRRR (SEQ ID NO:5) (NCR247 ortholog), RNGCIVDARCPYQKCSYPLYC (SEQ ID NO:6) (NCR247 ortholog with the 3 terminal amino acids deleted), RNGCIVDARCPYQKCSYPLYCXXX (SEQ ID NO:7), wherein X is any amino acid other than R (mutated NCR247 ortholog), RNGCIVDARCPYQKCSYPLYCAAA (mutated NCR247 ortholog) (SEQ ID NO:8), RPNGCLLN-PRCPYATDRCRA (SEQ ID NO:9) (NCR247 ortholog), DRPTGCLLNPRCPYATEYCRQVEP (SEQ ID NO:10) (NCR247 ortholog).

As shown in the examples herein, the inventors have demonstrated that the peptides of the disclosure bind to and sequester heme, making them useful in the methods disclosed herein. The inventors have further shown that D-amino acid versions of the peptides have fewer off-target effects than L amino acid versions in addition to being less susceptible to proteolytic degradation, such that the D-amino acid containing peptides of the disclosure are particularly useful for therapeutic purposes. The peptides may be chemically synthesized using known techniques.

In one embodiment, the peptides comprise of consist of the amino acid sequence selected from the group consisting of SEQ ID NO:1-8, wherein 1 or more amino acid residues are D amino acids. In another embodiment, the peptides comprise of consist of the amino acid sequence selected from the group consisting of SEQ ID NO:1-4, wherein 1 or more amino acid residues are D amino acids. In a further embodiment, the peptides comprise of consist of the amino acid sequence selected from the group consisting of SEQ ID NO:1 or 4, wherein 1 or more amino acid residues are D amino acids. In one embodiment, the peptides comprise of consist of the amino acid sequence selected from the group consisting of SEQ ID NO:1, wherein 1 or more amino acid residues are D amino acids.

In some embodiments, 2, 3, 4, 5, 6, 7, 8, 9, 10, 11, 12, 13, 14, 15, 16, 17, 18, 19, 20, 21, 22, 23, or all amino acid residues may be D amino acids. In one embodiment, all amino acid residues in the peptide are D amino acids.

The peptides may be combined with other functional units. In a second aspect, the disclosure provides polypeptides, comprising a first peptide comprising the amino acid sequence selected from the group consisting of SEQ ID NO:1-10 linked to a functional domain. In various embodiments, the first peptide may be any peptide or combination of peptides disclosed in the first aspect of the disclosure.

In one embodiment, the functional domain may comprise a compound to increase serum half-life of the polypeptide. Any compound to increase serum half-life may be used as appropriate for an intended use, including but not limited to polyethylene glycol (PEG), hydroxyethyl starch (HES), a flexible repetitive hydrophilic sequence of proline, alanine and serine amino acids 100-600 residues in length (PASylation), albumin, Fc domains, and albumin binding domains. These embodiments may also increase recycling of the peptide-heme complexes.

In another embodiment, the functional domain may comprise a detectable moiety. Any detectable moiety may be used as appropriate for an intended use, including but not limited to fluorescent moieties, luminescent moieties, radioactive moieties, maltose binding protein, biotin, hemagglutinin tag, streptavidin, any other tag that can be used to detect with an antibody, and (p-benzoyl-1-phenylalanine) (BPA) (can be used to chemically or UV crosslink to other proteins).

In another embodiment, the functional domain comprises a cell penetrating peptide and/or a moiety that facilitates crossing the blood-brain barrier.

In a third aspect, the disclosure provides compositions, comprising a peptide comprising the amino acid sequence selected from the group consisting of SEQ ID NO:1-10, fixed to a support. Compositions according to this embodiment may be used in various methods of the disclosure, as noted herein. In one embodiment, the peptide comprises the peptide or polypeptide of any embodiment of the first and second aspects of the disclosure. Any support may be used as appropriate for an intended use, including but not limited to a column matrix, a well, a plate, a slide, a tube, a dipstick, a bead, a nanoparticle, a medical device, or a filter (including but not limited to a membrane). In some embodiments, the peptide or polypeptide may be embedded in a substance or matrix that allows for controlled release of the peptide.

The peptides, polypeptides, and compositions may be combined with any other components as deemed appropriate for an intended use. In one embodiment, the disclosure provides formulations, comprising the peptide, polypeptide, or composition of any embodiment herein, and an anti-oxidant. Any anti-oxidant may be used as suitable for an intended purpose, including but not limited to dithiothreitol (DTT) and beta-mercaptoethanol.

The disclosure also provides pharmaceutical compositions, comprising the peptide, polypeptide, composition, or formulation of any embodiment or combination of embodiments; and a pharmaceutically acceptable carrier. The pharmaceutical compositions can be used, for example, in the methods disclosed herein. The pharmaceutical composition may further comprise (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions described herein are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.)

The composition may be formulated for any type of delivery, including but not limited to oral, parenteral, intravenous, sub-cutaneous, pulmonary, and nasal delivery. The peptide may be the sole active agent administered in the pharmaceutical composition, or the composition may comprise one or more other active agents suitable for an intended use.

In a fourth aspect, the disclosure provides medical devices comprising the peptide of any one of SEQ ID NO:-10, derivative, variant, homolog, or enantiomer thereof, coated on a surface of the medical device. The medical devices can be used, for example, for placement in subjects in need thereof to reduce the risk of bacterial infection/biofilm formation on the medical device. Any suitable medical device can be used, including but not limited to catheters (urinary catheters, intravascular catheters, etc.), pacemakers, dentures, prosthetic heart valves, cerebrospinal fluid shunts, ocular prostheses, prosthetic joints, orthopedic implants, titanium-containing implants, polystyrene-containing implants, surgical mesh implants, breast implants, dental implants, and intrauterine contraceptive devices. In various embodiments, the peptide comprises the peptide, polypeptide, composition, formulation, or pharmaceutical composition of any embodiment or combination of embodiments disclosed herein.

Heme is critical for most aerobic organisms because it is essential for respiration and also serves as a critical cofactor for various important proteins, such as certain enzymes that reduce oxidative stress. A surprising number of important pathogens are unable to synthesize heme (i.e. are heme auxotrophs) and thus are dependent on acquiring heme from their environment. The peptides of the disclosure can prevent their growth by tying up the free heme. The inventors have shown that NCR247 can block the growth of *Hemophilus influenzae*, a heme-requiring Gram-negative bacterial pathogen, and *Caenorhabditis elegans*, a heme-requiring representative roundworm. Some pathogens that require exogenous heme, for example the parasites causing malaria, Chagas disease, and Leischmaniasis, obtain heme within host cells so the peptides can be modified with a cell-penetrating peptide for such cases. In addition, some pathogens that can synthesize their own heme nevertheless have a requirement for exogenous heme to satisfy the extra-high heme requirements of certain stages in their life cycle, such as egg-laying. Alternatively, some pathogens rely on the uptake of exogenous heme to fulfil much of their requirement for iron. The peptides and polypeptides of the disclosure could affect a clinically important attribute of a pathogen without killing it. For example, the inventors have found that NCR247 interferes with the ability of the opportunistic fungal pathogen *Candida albicans* to form biofilms, which are important for its pathogenicity.

Although heme plays critical biological roles when complexed to various conventional heme-binding proteins (hemoproteins), free heme is very toxic because of its strong pro-oxidant properties [it can catalyze the formation of reactive oxygen species (ROS) by Fenton chemistry], strong pro-inflammatory properties, and cytotoxic properties. This toxicity of heme is particularly important in hemolytic syndromes or diseases such as sickle cell disease and malaria, but it is also critically important in variety of other medically important situations as discussed herein.

In another aspect, the disclosure provides methods for treating or limiting development of a subject having a disorder, comprising administering to the subject an amount effective to treat the disorder of an NCR247 peptide, derivative, variant, homolog, or enantiomer thereof, wherein the disorder is selected from the group consisting of a bacterial infection, a fungal infection, a kinetoplastid infection, an apicomplexan infection, a trypanosomatid infection, a parasitic worm infection, sepsis, toxoplasmosis, Chagas disease, and Leishmaniasis, malaria, cancer, Alzheimer's Disease, atherosclerosis, an inherited hemolytic disorder, ischemia reperfusion injury, sickle cell disease, β-thalassemia, tuberculosis, sleeping sickness, leishmaniasis, lymphatic filariasis, onchocerciasis, schistosomiasis, periodontal disease, acute kidney injury, intracerebral hemorrhage, subarachnoid hemorrhage, cardiovascular disease and neurodegenerative disease.

In all embodiments of the methods disclosed herein, the subject may be any subject that can be usefully treated. In one embodiment, the subject is a mammalian subject. In other non-limiting embodiments the subjects may include, but are not limited to, humans, cattle, sheep, goats, horses, chickens, dogs, cats, etc.

As used herein, "treating" means accomplishing one or more of the following: (a) reducing the severity of the disorder; (b) limiting or preventing development of symptoms characteristic of the disorder (s) being treated; (c) inhibiting worsening of symptoms characteristic of the disorder (s) being treated; (d) limiting or preventing recurrence of the disorder (s) in patients that have previously had the disorder(s); (e) limiting or preventing recurrence of symptoms in patients that were previously symptomatic for the disorder (s); and/or (f) limiting development of the disease in a subject at risk of developing the disorder, or not yet showing the clinical effects of the disease.

In one embodiment, wherein the disorder comprises a *H. influenza* infection. In another embodiment, the disorder comprises periodontal disease, including but not limited to chronic periodontitis. In a further embodiment, the disorder comprises a *C. albicans* infection resulting in biofilm formation. Further embodiments are described herein.

In another embodiment, the disclosure provides methods to remove free heme from the stored blood, comprising contacting the stored blood with an NCR247 peptide, derivative, variant, homolog, or enantiomer thereof. In a further embodiment, the disclosure provides methods for treating a subject in need of a blood transfusion, comprising prior to administering the blood transfusion, contacting the blood to be administered with an NCR247 peptide, derivative, variant, homolog, or enantiomer thereof. In various embodiments, the NCR247 peptide, derivative, variant, homolog, or enantiomer there is fixed to a support. The NCR247 peptide, derivative, variant, homolog, or enantiomer thereof may be as described for any embodiment or combination of embodiments herein.

In one embodiment, the disclosure provides methods of sequestering heme from an environment and rendering the heme biologically inaccessible, the method comprising contacting said environment with an NCR247 peptide, derivatives, variants, homologs, or enantiomers thereof. The heme-sequestering activity of the peptides is described at length herein. In various non-limiting embodiments, the environment may be a biological sample (blood, urine, semen, saliva, vaginal secretion, etc.), a cell culture, a plate, a tube, a well surface, or a medical device. In one embodiment, the NCR247 is fixed to a support, including but not limited to a column matrix, a well, a plate, a slide, a tube, a dipstick, a bead, or a nanoparticle. Further embodiments are described herein.

In another embodiment, the disclosure provides methods of inhibiting pathogen growth in a subject by sequestering heme in the subject and rendering the heme biologically inaccessible, the method comprising administering to said subject an NCR247 peptide, derivatives, variants, homologs, or enantiomers thereof. In one embodiment, the pathogen is selected from the group consisting of a bacterial pathogen, a fungal pathogen, and a parasite. In another embodiment, the parasite is selected from the group consisting of a kinetoplastid parasite, an apicomplexan parasite, and a parasitic worm. In another embodiment, the parasitic worm is a helminth. Further embodiments are described herein.

In a further embodiment, the disclosure provides methods of reducing toxicity of free heme arising from a disease, disorder, or condition arising due to free heme in a subject, the method comprising administering to the subject an NCR247 peptide, derivatives, variants, homologs, or enantiomers thereof. In one embodiment, the disease, disorder, or condition in the subject is selected from the group consisting of cancer, Alzheimer's, atherosclerosis, an inherited hemolytic disorder, ischemia reperfusion injury, and a condition associated with transfusion of trauma-hemorrhage patients using stored blood. In another embodiment, the inherited hemolytic disorder is sickle cell disease. In a further embodiment, the cancer is selected from the group consisting of lung cancer (such as non-small cell lung cancer), colon cancer, head & neck cancer, brain cancer, liver cancer, pancreatic cancer, prostate cancer, ovarian cancer, testicular cancer, uterine cancer, breast cancer (such as triple negative breast cancer), skin cancer (such as melanoma), lymphoma, or leukemia. In one embodiment, the cancer is selected from the group consisting of a recurrent cancer, drug resistant cancer, primary cancer or metastatic cancer. In another embodiment, the methods further comprises treating said subject with another cancer therapy such as chemotherapy, radiotherapy, immunotherapy, toxin therapy, hormonal therapy, or surgery. Further embodiments are described herein.

In one embodiment, the disclosure provides methods of treating a disease, disorder or condition in a subject by sequestering heme in the subject and rendering the heme biologically inaccessible, the method comprising administering to said subject an NCR247 peptide, derivatives, variants, homologs, or enantiomers thereof. In one embodiment, the disease is selected from the group consisting of cancer, Alzheimer's, atherosclerosis, an infectious disease, an inherited hemolytic disorder, ischemia reperfusion injury, and a condition associated with transfusion of trauma-hemorrhage patients using stored blood. In another embodiment, the infectious disease is a disease caused by a pathogen selected from the group consisting of a bacterial pathogen, a fungal pathogen, and a parasite.

In one embodiment of all embodiments of the disclosure, the NCR247 peptide, derivatives, variants, homologs, or enantiomers thereof comprise the peptide, polypeptide, composition, formulation, or pharmaceutical composition of any embodiment or combination of embodiments described herein.

As used herein, an "amount effective" refers to an amount of the peptide, polypeptide, etc. that is effective for treating and/or limiting the disorder. The peptides, polypeptides, compositions, and formulations are typically formulated as a pharmaceutical composition, such as those disclosed above, and can be administered via any suitable route, including orally, parentally, by inhalation spray, nasally, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally.

Dosage regimens can be adjusted to provide the optimum desired response (e.g., a therapeutic or prophylactic response). A suitable dosage range may, for instance, be 0.1 μg/kg-100 mg/kg body weight. The compositions can be delivered in a single bolus, or may be administered more than once (e.g., 2, 3, 4, 5, or more times) as determined by an attending physician.

In another embodiment, the disclosure provides nucleic acids encoding an amino acid sequence comprising or consisting of the amino acid sequence selected from SEQ ID NO:1-10. In this embodiment, the encoded amino acid residues are all L amino acid residues. The nucleic acid sequence may comprise RNA or DNA. Such nucleic acid sequences may comprise additional sequences useful for promoting expression and/or purification of the encoded peptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In a further embodiment, the disclosure provides recombinant expression vectors comprising the nucleic acids of the disclosure operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors include but are not limited to, plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector (including but not limited to a retroviral vector), or any other suitable expression vector.

In one embodiment, the disclosure provides recombinant host cells comprising the recombinant expression vectors of the disclosure. The host cells can be either prokaryotic or eukaryotic. The cells can be transiently or stably engineered to incorporate the expression vector of the invention, using techniques including but not limited to bacterial transformations, calcium phosphate co-precipitation, electroporation, or liposome mediated-, DEAE dextran mediated-, polycationic mediated-, or viral mediated transfection.

Inhibition of Pathogen Growth
Bacterial Pathogens

Some important bacterial pathogens are heme auxotrophs and thus must get heme from external sources to aerobically respire and to activate catalases that protect against the oxidative burst of host phagocytes. However, even if a bacterial pathogen can synthesize its own heme, heme can also be important for iron acquisition during infection and thus for virulence. Iron acquisition is a challenge for every human pathogen and the most abundant source of iron within vertebrates (>70%) is in the form of heme as a cofactor of hemoproteins. The inactivation of genes involved in heme acquisition in *B. pertussis, V. cholerae, Haemophilus* spp, *S. aureus* results in attenuated virulence in animal models.

The below three bacterial pathogens illustrate therapeutic applications of heme sequestration using the peptides, polypeptides, and methods of the disclosure. Examples of other pathogens that are heme auxotrophs besides the three discussed below include: i) *Bacteroides thetaiotaomicron* and *Bacteroides fragilis*, which are residents of the microbiome but also opportunistic pathogens, ii) *Bartonella henslae*, which causes cat-scratch disease, and iii) *Streptococcus agalactiae*, a Gram-positive Group B *streptococcus* that can cause devastating neonatal infections including septicemia and meningitis and invasive infections in adults.

*Hemophilus influenzae*. *H. influenzae* is responsible for a wide range of localized and invasive infections. However, it is a naturally occurring heme auxotroph that lacks almost all enzymes for heme biosynthesis and thus has an absolute growth requirement for either heme or its immediate precursor protoporphyrin IX. As shown in the examples, the peptides of the disclosure stop the growth of *H. influenzae* and that after a period of time the cells start to die. The effect is rescued by adding excess heme. Thus, the peptides can be a species-specific antibiotic for *H. influenzae* that is first static and then bactericidal. This is important for *H. influenzae* because it has acquired resistance to many antibiotics. The peptides can act extracellularly to sequester heme. *H. influenzae* is known to resist antimicrobial peptides by importing them into the cytoplasm using its Sap transporter and proteolytically degrading them. The inventors' observation that D-NCR247 is more effective than L-NCR247 suggests that some of both L-NCR247 and D-NCR247 can be imported into the *H. influenzae* cytoplasm, but that D-NCR247 is more effective because it is resistant to proteolysis.

*Porphyromonas gingivalis*. Chronic periodontitis is the 6th most common infection worldwide, affecting an estimated 5-20% of the world population and associated with a host of other diseases conditions, including coronary artery disease, rheumatoid arthritis, diabetes, pulmonary diseases, cancers of the oro-digestive tract, and Alzheimer's disease. Chronic periodontitis results from a breakdown in the homeostasis between the periodontal tissue and the surrounding microbes, subsequently leading to uncontrolled inflammation and tissue destruction. The loss of tissue homeostasis is initiated by communities of microorganisms colonizing the subgingival area. Although about. 700 species of bacteria representing 13 phyla have been identified in the human oral cavity, *P. gingivalis*, a low abundance bacterium, is regarded as a keystone pathogen that initiates periodontitis in the context of a multispecies microbial community.

*P. gingivalis* is unable to synthesize the porphyrin macrocycle and relies on exogenous porphyrin, including heme or heme biosynthesis intermediates from host sources. Also, as a protective strategy, *P. gingivalis* is able to accumulate a defensive cell-surface heme-containing pigment in the form of μ-oxo bishaem. Iron is utilized by this pathogen in the form of heme and has been shown to play an essential role in its growth and virulence. The main sources of heme for *P. gingivalis* in vivo are hemoproteins present in saliva, gingival crevicular fluid, and erythrocytes. Unlike other Gram-negative bacteria, *P. gingivalis* does not produce siderophores, but rather uses several mechanisms to acquire heme. In the case of red cells, proteases digest surface proteins, which results in the release of hemoglobin that is then digested proteolytically to release heme or has its heme extracted by the hemaphore HmuY before transport into the cell through receptors such as HmuR. Sequestering heme would inhibit *P. gingivalis* growth.

*Mycobacterium tuberculosis*. Tuberculosis caused by the human pathogen *M. tuberculosis* (Mtb) causes more death than any other infectious disease. Mtb contains numerous hemoproteins with key roles, including defense against oxidative stress, cellular signaling and regulation, host cholesterol metabolism, and respiratory processes. Various heme enzymes in Mtb are validated drug targets and/or products of genes essential for bacterial viability or survival in the host. Mtb can synthesize its own heme, but iron is crucial for Mtb to infect the host. More than 70% of iron in the human body is tightly bound in heme and complexed with hemoglobin, making heme the major iron source in the human host. Mtb imports heme using the Dpp ABC transporter mentioned above. Sequestering heme can help with Mtb infections but would likely require a cell-penetrating version of NCR247 since Mtb is an intracellular pathogen.

Fungal Pathogens

NCR247 can inhibit *Candida albicans* biofilms.

*C. candida*, a commensal fungus normally residing on the skin and on mucosal surfaces, is the most common opportunistic fungal pathogen. In immunocompetent individuals, *C. albicans* causes local mucosal, cutaneous and nail infections. However, in debilitated or immunocompromised individuals, *C. albicans* is the most prevalent systemic fungal pathogen, accounting for close to a million cases/year with a high (40%) mortality. *C. candida* can synthesize heme. However, heme represents greater than 70% of the human host's iron quota, so like numerous other pathogens, *C. candida* targets hemoglobin as an iron source in the iron-poor host environment. Restricting heme uptake can have significant physiological consequences.

Infections caused by *C. albicans* frequently occur in hospitalized patients, where it is notorious for forming biofilms on implanted medical devices, including catheters, pacemakers, dentures, and prosthetic joints, which provide a surface and sanctuary for biofilm growth. Once it forms on an implanted medical device, a *C. albicans* biofilm has the potential to seed disseminated bloodstream infections and to lead to invasive systemic infections of tissues and organs. For example, over five million central venous catheters are placed each year in the United States. Currently—even with recently improved clinical approaches—biofilm infection occurs in over 50% of these catheters and is responsible for an estimated 100,000 deaths and $6.5 billion in excess expenditure annually in the United States alone. Moreover, because fungal biofilms are largely resistant to current antifungal drugs, high antifungal doses together with removal of the colonized medical device are generally required to treat infections. Removal of some devices is costly and in cases where administration of high doses of antifungal agents is even possible, they can cause serious complications, including kidney and liver damage.

No biofilm-specific drugs exist today for *C. albicans* making treatment of biofilm-based infections particularly problematic. Strategies that weaken *C. albicans* biofilm formation or maintenance could render biofilms susceptible to conventional antifungal drugs, making combination therapies effective. The peptides, polypeptides, and other compositions, and methods of the disclosure can be used to treat fungal infections based on its ability to disrupt biofilm formation.

Parasites

Parasites of various classes infect a large fraction of the world population, many of them causing important, difficult-to-treat, human diseases. Heme limitation by the peptides, polypeptides, and other compositions, and methods of the disclosure can be used as an anti-parasitic therapeutic. Several medically important parasites have lost their ability to synthesize their own heme because their genomes lack some or all heme biosynthetic genes and thus, they must rely on exogenous sources of heme. Additionally, utilization of exogenous heme can be important even for parasites that possess their own heme biosynthetic pathway because: i) they have a very high demand for heme at certain times, e.g., for egg laying, or ii) that their strategy for iron acquisition relies heavily on importing exogenous heme rather than using siderophores.

Kinetoplastid Parasites

The Kinetoplastea are a group of flagellated protists characterized by an organelle with a large, massed DNA (the kinetoplast). Protozoan parasites from the Trypanosomatidae family of the Kinetoplstea are responsible for devastating diseases that affect millions of people in developing countries. Such parasites are amenable to therapy using the peptides, polypeptides, and other compositions, and methods of the disclosure because they are not only hard-to-treat pathogens but are also heme auxotrophs. Their current control is based on the use of toxic, old chemotherapeutic agents that are poorly effective and often hampered by drug resistance. There is therefore a great need to develop new antiprotozoal agents.

*Trypanosoma cruzi* causes Chagas disease, the most prevalent parasitic disease in several countries of the Americas. It has been estimated that 6.2 million people, mostly in Mexico, Central America and South America, had Chagas disease as of 2017. Early infections are treatable with the medications beznidazole or nifurtox, which usually cure the disease if given shortly after the person is infected, but become less effective the longer a person has had Chagas disease. Both also have substantial side effects. Up to 45% of people with chronic infection develop heart problems 10-30 years after the initial illness, which can lead to heart failure.

*Trypanosoma brucei* causes sleeping sickness, which is transmitted by infected tsetse flies and is endemic in 36 sub-Saharan African countries. Without treatment, the disease is considered fatal.

*Leishmania*. *Leishmania* spp. are trypanosomatid parasites that replicate intracellularly in macrophages, causing serious human morbidity and mortality throughout the world. With more than twenty known species of *Leishmania* that can cause disease in humans, leishmaniasis is estimated to be the ninth largest infectious disease burden in the world, with an estimated 1.3 million new infections reported each year. Current treatments are expensive, toxic, and are gradually becoming ineffective with the rise of drug resistance in endemic areas. Consequently, there is a great need for the development of new drugs that are more affordable, less toxic, and that have greater efficacy against the disease.

Consistent with being heme auxotrophs, the genomes of *T. cruzi* and *T. brucei* completely lack heme biosynthetic genes, while those of *Leishmania* spp. lack the genes for the first five biosynthetic steps. Yet all three parasites possess several heme-proteins involved in essential metabolic pathways (e.g. enzymes required for the biosynthesis of ergosterol and unsaturated fatty acids, as well mitochondrial cytochromes in the respiratory chain) and so must import heme from an exogenous source. Both *T. cruzi* and *Leishmania* have been shown to encode functional orthologs, TcHTE and LHR1 respectively, of the HRG class of ABC-cassette heme importer that was first characterized in *C. elegans* (see below). The apparent redundancy of heme importers in these Trypanosomatids could complicate efforts to block heme import by the strategy of blocking heme import. A strategy based on heme sequestration using the peptides, polypeptides, and other compositions, and methods of the disclosure is not dependent on the number heme importers.

*T. brucei* replicates in human various body fluids (blood, lymph, and spinal fluid), so *T. brucei* can be inhibited by NCR247 sequestration of extracellular heme. Although the infective form (trypomastigotes) of *T. cruzi* is found in the blood, when initially taken up into cell it is transiently sheltered in parasitophorous vacuoles but is then released free into the cytoplasm to replicate in a form termed amastigotes. The TcHTE receptor is preferentially expressed in the *T. cruzi* replicative forms rather than in the infective form, but the status of the second heme transporter in these two forms has not yet been reported. The peptides, polypeptides, and other compositions, and methods of the disclosure can be effective by limiting extracellular heme acquisition by the non-replicating infective form found in the blood. This could, for example, inhibit ergosterol synthesis, which *T. cruzi* and Leischmania need at all phases of their life cycle and requires a heme-containing P450 enzyme for its synthesis. Since *T. cruzi* replication occurs intracellularly, the peptides of the disclosure can be equipped with a cell-penetrating peptide to block replication. Leischmania replicates only intracellularly in parasitophorous vacuoles in macrophages and other professional phagocytes. Sequestration of extracellular heme by the peptides, polypeptides, and other compositions, and methods of the disclosure can inhibit the virulence of the non-replicating form, and block replication.

Apicomplexan Parasites: Malaria

Two important apicomplexan parasites include i) *Plasmodium* spp., which causes malaria (estimated 229 million cases/409,000 deaths worldwide in 2019) and *Toxoplasma gondii*, which infects a third of the world's population. Unlike some other parasites, both *Plasmodium* spp. and *Toxoplasma gondii* can synthesize their own heme, but also are exposed to host heme. Heme sequestration by the peptides, polypeptides, and other compositions, and methods of the disclosure can be used as a therapeutic treatment for malaria, especially since resistance to antimalarial medicines is a recurring problem.

*Plasmodium* spp. has numerous important heme-proteins and thus needs a source of heme throughout its whole complex life cycle. In the mosquito and liver stage, its own biosynthetic pathway can supply its heme requirement. However, this is not true in the blood stage where the parasites grow intracellularly inside of red blood cells (erythrocytes). They release so much potentially toxic heme when they degrade hemoglobin that they polymerize it into hemozoin, a chemically inert pigment. Even though the parasites express their heme biosynthetic enzymes during this stage, they are not essential, which implies that the parasites must use some of the heme obtained for hemoglobin degradation to satisfy their heme requirements. Sequestration of free heme in the plasma by the peptides, polypeptides, and other compositions, and methods of the disclosure, can be used to treat malaria by reducing the symptoms of severe malaria independent of any effect it might have on the parasites.

Parasitic Worms (Helminths)

As detailed herein, certain parasitic worms (Helminths) are another class of devastating pathogen to be treated by using the peptides, polypeptides, and other compositions, and methods of the disclosure to deprive them of heme. Parasitic worms (Helminths) are a group of organisms which share a similar form but do not necessarily share an evolutionary relationship. The soil-transmitted helminths live for years in the human gastrointestinal tract and more than a billion people are infected with at least one species. Soil-transmitted helminths, blood flukes, and filarial worms collectively infect more than a quarter of the human population worldwide at any one time, far surpassing HIV and malaria together. Schistosomiasis is the second most prevalent parasitic disease of humans after malaria. Many of these nematodes require heme for growth, but heme also serves as important iron source since these worms feed on red blood cells.

Nematoda (roundworms). Nematodes are of particular interest with respect to therapy using the peptides, polypeptides, compositions, formulations, and methods disclosed herein, because all nematodes lack a heme biosynthetic pathway and so must acquire heme from exogenous sources. Furthermore, heme also serves as an important iron source since pathogenic nematodes feed on red blood cells.

When grown in the lab, the widely-studied model nematode *Caenorhabditis elegans* normally acquires heme by ingesting bacteria and breaking them down to release heme. When heme is bound to a protein, it can be released by simple proteolytic digestion, but *C. elegans* also possesses an enzyme that can cleave the thioester bond that physically attached heme to cytochrome C. A new class of heme importer was identified in *C. elegans* by analyzing heme-responsive proteins and orthologs have been subsequently identified in other parasites such as the kinetoplastid parasite discussed above. In a proof-of-principle experiment, we demonstrated that the addition of NCR247 blocks growth of the nematode *C. elegans*, arresting them in the L1 stage.

Filarial worms (Nematodes). Lymphatic filariasis and onchocerciasis are severe diseases that affect more than 150 million people worldwide. Lymphatic filariasis is caused by caused by the filarial nematodes *Wuchereria bancrofti*, *Brugia timori*, and *Brugia malayi*, while onchocerciasis (river blindness; second-leading cause of blindness worldwide after Tracoma) is caused by the filarial nematode *Onchocerca volvulus*. Because they are nematodes, these parasitic worms are heme auxotrophs that lack the ability to make their own heme. *B. malayi* possess multiple function orthologs of the *C. elegans* HRG heme transporters and has been shown to be capable of importing exogenous heme. The worms are thus subject to inhibition by the peptides, polypeptides, and other compositions, and methods of the disclosure.

Hookworms (Nematodes). Soil-transmitted helminths are responsible for major neglected tropical diseases mostly in developing countries. In particular, the blood-feeding nematode hookworms *Necator americanus* and *Ancylostoma duodenale* infect ca.740 million people in rural areas of the tropics and subtropics. Hookworm infection is acquired by invasion of the infective larval stages through the skin or mouth. Following host entry, the larvae undergo a journey through the vasculature, then the lungs and other tissues, before they enter the gastrointestinal tract and molt twice to become one-centimeter-long adult male and female worms. The worms mate and the female hookworms produce up to 30,000 eggs per day, which exit the host's body in the feces. Adult hookworms cause morbidity in the host by producing intestinal hemorrhage. Because these hookworms are nematodes and lack heme biosynthetic genes, they require an exogenous source of heme. Adult hookworms ingest the blood released by intestinal hemorrhage, rupture the erythrocytes, and degrade the hemoglobin, which is likely their source of heme. The infectivity of hookworms, which feed on the blood of the host, is significantly lower in anemic hamsters fed on a low iron diet. Thus, the development of hookworm larvae into adults in humans and their egg-laying can be prevented by using the peptides, polypeptides, and other compositions, and methods of the disclosure to sequester heme.

Flukes and Blood Flukes (Platyhelminthes/flatworms).

*Schistosoma*, commonly known as blood flukes, is a genus of the trematode class of Platyhelminthes/flatworms. These parasitic flatworms are responsible for Schistosomiasis, which is considered by WHO as the second-most socioeconomically devastating parasitic disease (after malaria), with hundreds of millions infected worldwide. Schistosomes are Platyhelminths/flatworms, not nematodes, and encode a full heme biosynthetic pathway in their genomes.

Schistosomes ingest host erythrocytes, liberating large quantities of heme. Since heme is toxic, much of it is rapidly inactivated and eliminated. However, at least some seems to be essential to support growth, development, and reproduction and the worms have numerous endogenous hemoproteins. The organism possesses a transmembrane heme transporter that is present at particularly high levels in tissue involved in oogenesis. Heme uptake has been shown to be essential for egg production by *S. mansoni*. Since schistosomes take up exogenous heme, schistosomes can be inhibited by using the peptides, polypeptides, and other compositions, and methods of the disclosure to sequester heme.

Class II: Uses of NCR247-Mediated Heme Sequestration to Reduce Toxicity of Free Heme in Various Diseases, Syndromes, and Other Clinical Situations Although heme plays numerous important biological roles when properly bound to a variety of heme proteins, free heme (or "loosely-bound" heme that is associated with non-hemoproteins) is very toxic because it has a variety of pro-oxidant, pro-inflammatory and cytotoxic effects. Free heme levels rise in a striking number of medically important situations when the amount of heme being produced overwhelms the ability of the heme oxygenase HO-1 enzyme to destroy it and the amount of hemopexin available to bind it. For example, the toxicity of heme plays a major role in prototypical hemolytic disorders, including malaria and sickle cell disease, but it is also critically involved in diseases that are not associated with hemolysis such as severe sepsis and atherosclerosis. Although the plasma free heme levels in healthy individuals are ca. 0.2 µM, they can be as high as 20-50 µM in the plasma of patients with severe hemolytic events.

The molecular mechanism underlying the cytotoxic effect of free heme is partly due to its strong pro-oxidant activity, which is driven by the divalent Fe atom contained within its protoporphyrin ring and that can promote the non-enzymatic production of free radicals via Fenton chemistry. The production of ROS, particularly hydroxyl radicals, damages a wide variety of molecules including lipids, nucleic acids, and proteins. Free heme also has powerful pro-inflammatory activity because it is recognized as a DAMP (Damage Associated Molecular Pattern) that induces strong inflammatory responses through TLR-4 signaling, as well as activation of the NLRP3 inflammasome and complement system activation; free heme also stimulates neutrophils to make ROS by enzymatic mechanisms. Free heme also has strong cytotoxic properties. Free heme's toxicity is exacerbated by its extreme hydrophobicity, which allows it to intercalate into the phospholipid membranes. This results in the oxidation of the cell membrane and promotes lipid peroxidation, thereby increasing membrane permeability and ultimately leading to cell death.

Suppressing Heme Toxicity Arising from Infectious Disease Malaria

As discussed above, the methods disclosed herein can be used to treat malaria by inhibiting the growth of the *Plasmodium* parasite in the blood stage. Independent of any effect it might have on the parasite, the peptide's ability to counteract heme toxicity can reduce the most severe symptoms of malaria and thus increase tolerance to the infection. *Plasmodium* replication inside red blood cells leads to hemolysis, the release of hemoglobin and subsequently the release of free heme. Free heme plays a central pathogenic role in severe forms of malaria, so the methods may increase survival by reducing the symptoms of severe malaria.

Severe Sepsis

Severe sepsis is a disease with limited treatment options that kills more than half a million individuals per year in the USA alone. Free heme induces programmed cell death in response to a proinflammatory agonist, such as tumor necrosis factor (TNF). This causes irreversible tissue damage and organ failure, the hallmarks of severe sepsis. This phenomenon is referred to as "heme sensitization" because the cytotoxic effects of free heme are revealed only in the presence of other cytotoxic agonists. The molecular mechanism underlying the cytotoxic effect of free heme is due in part to its pro-oxidant activity driven by the divalent Fe atom contained within its protoporphyrin ring, which can promote the non-enzymatic production of free radicals via Fenton chemistry. It is also due in part to free heme's pro-inflammatory ability to strongly induce inflammatory responses, which even includes stimulating neutrophils to make even more ROS by enzymatic mechanisms. In addition, independent of these effects, heme causes a viscous cycle in sepsis by impairing phagocytic functions and increasing susceptibility to infection. By sequestering free heme, the methods of the disclosure can significantly increase the survival of patients experiencing severe sepsis.

Suppressing Heme Toxicity Associated with Sickle Cell Disease and Other Inherited Hemolytic Disorders Sickle cell disease (SCD) includes a group of inherited disorders caused by mutations in the hemoglobin subunit β. Patients with hemolytic disorder such sickle cell disease (SCD) exhibit increased serum levels of heme and develop acute and/or chronic manifestations of heme toxicity. Worldwide, about 4.4 million people have SCD, while an additional 43 million have the sickle cell trait. About 80% of SCD cases occur in Sub-Saharan Africa. In the USA, 1 of every 365 African Americans have the trait and it is responsible for ca. 113,000 hospitalizations per year. The clinical hallmarks of SCD are chronic pain and acutely painful vaso-inclusive crises as well as numerous other symptoms.

When homozygous, the mutation causes hemoglobin to polymerize, which leads to red blood cell deformation (sickle shape). This in turn leads to rupture of red blood cells, which results in hemoglobin and heme released into the circulation. The intensity and chronicity of this hemolysis leads to the release of so much heme that it exceeds the capacity of available hemopexin to control it. This creates an acquired hemopexin deficiency that allow plasma heme levels to rise as high as 20-50 μM, which has been implicated in the pathology of SCD. Sequestering free heme using the methods of the disclosure can reduce not only a variety of the deleterious physiological consequences of SCD, but also to mitigate the pervasive pain that is associated with this all too-common genetic disease.

Suppressing Heme toxicity Associated with Ischemia Reperfusion Injury

Ischemia Reperfusion Injury is a major life-threatening problem associated with organ transplantation, sepsis, acute coronary syndrome, limb injury, and the vaso-occlusion associated with SCD. Ischemia occurs when the blood flow is less than the demand for normal function, while Reperfusion is the re-establishment of blood flow to previously ischemic tissues. Despite establishment of blood flow being essential to salvage ischemic tissues, reperfusion itself paradoxically causes further damage that is referred to as Ischemia Reperfusion Injury (IRI). IRI threatens function and viability of the organ and presents challenges to physicians as they attempt to preserve organ and neurogenic function. Serious clinical manifestations associated with IRI include myocardial hibernation, acute heart failure, cerebral dysfunction, gastrointestinal dysfunction, systemic inflammatory response syndrome, and multiple organ dysfunction syndrome. A detailed mechanism of ischemia-reperfusion injury has not been described. However, it is known that when the blood supply is re-established after prolonged ischemia, local inflammation and ROS production increase, leading to secondary injury and that the cell damage induced by prolonged IRI may lead to apoptosis, autophagy, necrosis, and necroptosis. The methods of the disclosure provide an important strategy to ameliorate the deleterious consequences of IRI, including IRI during organ transplantation, IRI in SCD, and the cerebral ischemia after aneurysmal subarachnoid hemorrhage.

Suppressing Heme Toxicity Associated with Transfusions of Trauma-Hemorrhage Patients Using Stored Blood Trauma is the leading cause of death and disability in patients aged 1-46 years of age. Severely injured patients experience considerable blood loss and hemorrhagic shock requiring treatment with massive transfusion of red blood cells. Because of the amount of blood involved, these transfusions often employ stored red blood cells, which can be used for up to 42 days. However, for severely injured patients who have massive bleeding and receive many transfusion units, transfusion with older, stored blood is associated with dysfunction in blood flow, increased injury and inflammation in critical end organs, and lung infection, and heme has been implicated as a key factor in the problems associated with using stored red blood cells. Compared to fresh blood, resuscitation with the stored blood resulted in 4× the levels of heme observed using fresh blood and significantly increased bacterial lung injury, as shown by higher mortality, and increases in fluid accumulation and bacterial numbers in the lungs. The peptides, polypeptides, compositions, formulations, and methods of the disclosure can also the effects of transfusing trauma-hemorrhage patients with stored red blood cells. BY way of non-limiting example, the peptides, polypeptides, compositions, formulations, or pharmaceutical compositions be administered intravenously before the onset of resuscitation, or used to remove excess heme from the stored red blood cells prior to transfusion.

Heme Sequestration to Treat Cancer p53, mutated in about 50% of human cancers has a heme-binding site in its C-terminus. Heme binding to this site interferes with p53's ability to bind DNA and hence its ability to modulate gene expression. Furthermore, the binding of heme to p53 promotes its nuclear export and degradation via the ubiquitin-proteasome system. The methods of the disclosure can thus be used, for example, to treat NSCLC and Acute Myeloid Leukemia.

Heme Sequestration to Treat Alzheimer's Disease

Alzheimer's Disease (AD) is the most common neurodegenerative disease in Western countries and is becoming a problem worldwide. The number of people affected in the US in 2018 was 5.7 million and is expected to double to 14 million by 2050, which would represent about 3% of the projected US population. However, there still is no intervention that cures, prevents, or even slows AD progression. Aβ amyloid peptides are derived from cleavage of the amyloid transmembrane precursor protein (APP) by the action of β- and γ-secretases. The most abundant of these are Aβ (1-40) and Aβ (1-42), but mutations associated with inherited Alzheimer's disease favor the production of Aβ (1-42), which aggregates more readily. These Aβ peptides are best known for forming various types of fibrils and aggregates and assembling into senile plaques in the brains of Alzheimer's patients, However, the Aβ (1-42) peptide also binds heme with high affinity ($K_d$=140 nM) to form a 1:1 or 2:1 complex. Remarkably, this Aβ-heme complex has a peroxidase activity that can oxidize a variety of molecules, including the important neurotransmitters serotonin and 3,4-dihydroxyphenylalanine (DOPA) as well as cytochrome C. Heme binding by Aβ amyloid peptides to create a peroxidase likely contributes to the neurodegeneration associated with human Alzheimer's Disease, and as shown in the examples, NCR247 can strip the heme out of the Aβ-heme complex. Thus the methods of the disclosure can be used to prevent the formation of the Aβ-heme complex.

Atherosclerosis

Atherosclerotic diseases are known to be the leading causes of death in the world. The plaques that form harden and narrow arteries impeding blood flow. When these plaques eventually rupture, the exposed material triggers blood clot formation, which can suddenly block blood flow through the artery, resulting in myocardial infarction or stroke. The heme-degrading enzyme heme-oxygenase 1 (HO-1) has been shown to have protective effects, indicating that free heme contributes significantly to the pathology of atherosclerosis. Reducing free heme levels using the methods of the disclosure can thus provide a therapeutic benefit to atherosclerosis.

Example 1

Abstract: Symbiotic partnerships with rhizobial bacteria enable legumes to grow without nitrogen fertilizer, because *rhizobia* convert atmospheric nitrogen gas into ammonia via nitrogenase. After *Sinorhizobium meliloti* penetrate the root nodules that they have elicited in *Medicago truncatula*, the plant produces a family of ca. 700 NCR (Nodule Cysteine Rich) peptides that guide differentiation of endocytosed bacteria into nitrogen fixing bacteroids. The sequences of the NCR peptides are related to the defensin class of antimicrobial peptides but have been adapted to play symbiotic roles. Using a variety of spectroscopic, biophysical and biochemical techniques we show that the most extensively characterized NCR peptide, defensin-like 24 amino acid NCR247, binds heme with nanomolar affinity. Bound heme molecules and their iron are made biologically inaccessible first by the formation of hexamers (6 heme: 6 NCR247) and then higher-order complexes. We present evidence that NCR247 is critical for an effective nitrogen-fixing symbiosis. We propose that, by sequestering heme and its bound iron, NCR247 creates a physiological state of heme deprivation. This in turn induces an iron-starvation response in *rhizobia* that results in iron import, which itself is required for nitrogenase activity. Using the same methods as for L-NCR247, we show that D-enantiomer of NCR247 can bind and sequester heme equivalently well. The special abilities of NCR247 and its D-enantiomer to sequester heme suggest a broad range of potential applications related to human health.

The ecologically and agriculturally important symbiosis between rhizobial bacteria and their legume hosts permits these plants to grow without nitrogen fertilizer, because the *rhizobia* use nitrogenase to convert nitrogen gas into ammonia. As part of this process, the bacteria penetrate the root nodules that they have elicited and are endocytosed into membrane compartments in the cytoplasm of plant cells in the interior of the nodules[1]. In the case of the *Sinorhizobium meliloti Medicago truncatula* symbiosis, the plant expresses a family of ca. 700 defensin-related NCR (Nodule Cysteine Rich) peptides specifically in the nodules only, which guide the endocytosed bacteria into terminally differentiating into nitrogen-fixing bacteroids[2]. Two of these peptides NCR211[3] and NCR169[4] have been shown to be critical for symbiosis but their molecular mechanism is not understood. A few NCR peptides have been shown to affect membrane polarization[5], while one has been shown to interact with a few bacterial proteins[6]. However, the molecular mechanisms of action of these NCR peptides in symbiosis is a major unanswered question in the field.

Here we set out to establish the mode of action of the smallest and best characterized of these peptides, 24 amino acid NCR247[7,8] (RNGCIVDPRCPYQQCRRPLYCRRR; SEQ ID NO:1). We unexpectedly discovered that NCR247 binds and sequesters heme with nanomolar affinity. This finding was of particular interest because it suggested a possible molecular mechanism for our previous observation that the complex transcriptional response of *S. meliloti* cells treated with a symbiosis-relevant concentration of NCR247 in vitro included increased expression of genes that are repressed by RirA[7]. RirA represses transcription of at least 53 iron-responsive genes including those involved in iron uptake[9]. Iron is of particular importance to the nitrogen-fixing symbiosis because each nitrogenase contains about 24-32 iron atoms. We carried out a set of biochemical, biophysical and physiological experiments to test the hypothesis that heme sequestration by NCR247 is a crucial step in establishing an effective symbiosis between *S. meliloti* and *M. truncatula*. Our results have revealed the first detailed molecular mechanism of action of any NCR peptide.

Results

Figure 1:
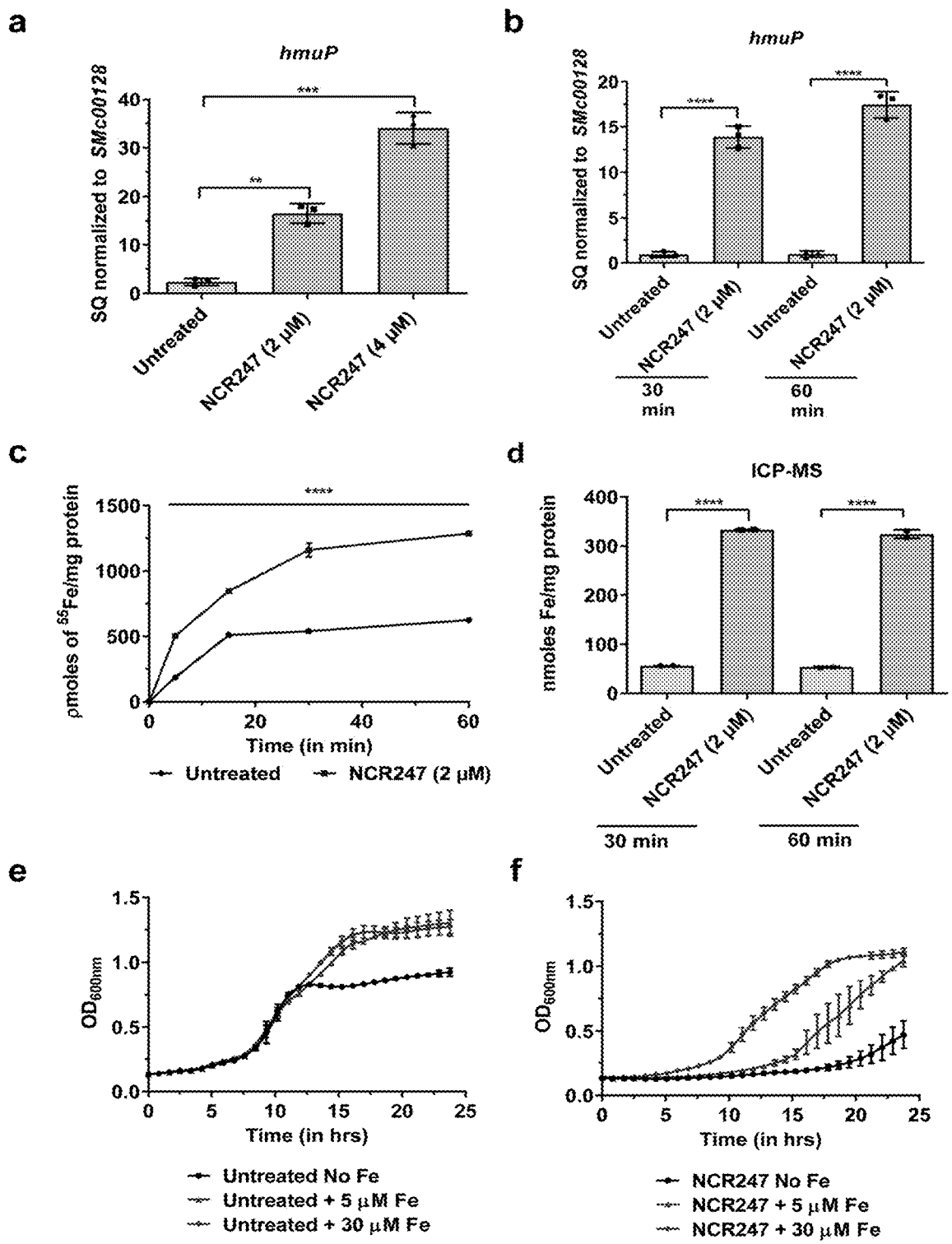
FIG. 1. NCR247 induces iron starvation response and drives iron import into S. meliloti. a, Increase in expression of a gene involved in iron import (hmuP) in S. meliloti upon NCR247 treatment for 30 mins, when grown in minimal media —Fe, as quantitated by qRT-PCR analysis. b, Increase in expression of hmuP upon NCR247 (2 µM) treatment when S. meliloti was grown in iron sufficient medium (5 µM). In a and b, the data are expressed as starting quantities (SQ) of respective mRNAs normalized to the control gene SMc00128 and are presented as an average of three technical replicates ±s.d. c, Increase in uptake of $^{55}$Fe upon treatment with 2 µM NCR247 when compared to untreated S. meliloti. d, Increase in total iron content of 2 µM NCR247 treated S. meliloti, measured by ICP-MS analysis. e, Growth pattern of untreated cells in iron-depleted (—Fe), iron sufficient (5 µM), and iron-replete media (30 µM). f, Rescue of growth by Fe in 2 µM NCR247 treated cells. In c-f, data are presented as mean of three biological replicates ±s.d. In a-d.

NCR247 elicits an iron starvation response; First, we tested the iron-related transcriptional response of *S. meliloti* to symbiotically relevant concentrations of NCR247[7,10] in minimal medium using qRT-PCR analysis. Consistent with our pervious transcriptome analysis[11], many of the iron uptake genes were increased in expression (FIG. 1a). Surprisingly, we observed NCR247 treatment led to an increase in transcript levels of iron uptake genes even when *S.* meliloti was grown in iron-replete medium (FIG. 1b; FIG. 6a-i), a condition in which iron-uptake is normally repressed. Using radioactive $^{55}$Fe uptake assay, we found that NCR247 markedly increased the import of $^{55}$Fe (FIG. 1c) into S. meliloti even when grown in medium with sufficient iron, resulting in an increase in an elevated total iron content of the cells measured by ICP-MS analysis (FIG. 1d). NCR247 causes a reduction in growth rate of S. meliloti in a minimal medium and, based on the above observations, we hypothesized that addition of iron might suppress this phenotype. Indeed, addition of increasing concentrations of iron progressively increased the growth rate of NCR247 treated cells (FIGS. 1e and 1f). Other metals we tested, including zinc and manganese, did not restore bacterial growth rates in the presence of NCR247 indicating that the effects we observed might be iron-specific responses (FIG. 6j). The slight alterations in Mn and Zn content of S. meliloti may be due to alteration in iron homeostatic mechanisms of S. meliloti (FIG. 6k). Our data support the hypothesis that NCR247 causes an iron starvation response in S. meliloti even under iron-replete conditions, but the molecular mechanism responsible for this effect was not clear.

NCR247 binds to heme: We made a serendipitous discovery when we observed that the Maltose Binding Protein (MBP)-tagged NCR247 purified as a reddish protein from E. coli (FIG. 7a). Several observations indicated that the colour of this chimeric protein was due to heme, including the UV-Vis absorption spectrum, which had a curve typical of heme-binding proteins (FIG. 7b); the direct detection of heme by mass spectrometry (FIG. 7c); the presence of porphyrin (porphyrin/protein ~0.20), and; the presence of iron (FIG. 7d).

In order to test if the chemically synthesized peptide used in the previous experiments as well as in many others, is also capable of binding heme, we added heme in a 1:1 ratio and it bound within seconds, as evidenced by a visible colour change (FIG. 2a). Moreover, we observed a UV-Vis absorption spectrum with maxima at 366, ~450, and 560 nm (FIG. 2b). An atypical hyper porphyrin (split-Soret) spectrum (similarly intense peaks at 366 and 450 nm) of NCR247-heme complex is very similar to that of only two other hemoproteins, both of which use two cysteines as axial ligands—DGCR8[12] and the N-terminal fragment of CD74[13]. Similar to heme-bound DGCR8, the EPR spectrum of NCR247-heme complex clearly revealed the presence of low spin Fe(III) ferric heme (FIG. 2c), and Raman spectroscopy identified the presence of ferric iron and a six-coordinate, low spin b-type heme (FIG. 2d).

Based on these analyses, we ascertained that the Fe(III) in the heme is double-cysteine ligated in the NCR247-heme complex[14, 15]. Consistent with this, an NCR247 derivative in which all four cysteines were mutated to serine (NSR247), which unlike NCR247, did not change colour in response to heme addition (FIG. 2a), had only one high spin species corresponding to free heme in EPR and Raman spectra (FIGS. 7e and 2f), and did not increase expression of iron uptake genes, even at concentrations of 15 uM of the peptide (FIGS. 7g and 7h). NCR247 also binds sodium dithionite-reduced Fe(II) ferrous heme (FIG. 7i). Biolayer interferometry using biotinylated heme[16] revealed that NCR247 binds heme with a $K_D$ of ~1 nM (FIG. 2e and FIG. 7j). Since heme is not a chiral molecule, the D-enantiomer of NCR247 bound heme similarly, as predicted (FIG. 2e). The NSR247 derivative bound heme ca. 4000× less well (FIG. 2e), consistent with cysteines having an important role in heme binding.

Due to the importance of CP motif in some heme binding proteins[17, 18], we tested whether $C_{10}P_{11}$ motif of NCR247 contributes to the tight binding to heme. Mutating the CP motif to SA decreased binding affinity, while additionally mutating $C_{15}$ to S caused a further decrease. Other amino acids are important as well. For example, since tyrosines have been known to contribute to heme binding[19, 20], we mutated $Y_{12}$ to A or both $Y_{12}$ and $Y_{20}$ to A's and also observed decreased heme binding affinity (FIG. 2e).

We hypothesized that the two axial cysteines that coordinate the heme iron likely come from different peptides, because altering the NCR247-heme ratio by titrating in heme increased the magnitude of absorption of both the 450 nm and 560 nm peaks until the ratio reached 2:1 (FIG. 8a). However, absorbance at 366 nm increased even after the other peaks were saturated, suggesting that, as for DGCR8, this could be due to higher-order structures forming as more heme is added[12]. Consistent with this notion, we used size exclusion chromatography to analyse MBP-NCR247 purified from normally grown E. coli and identified a major peak corresponding to the size of a monomer (heme/protein <0.2) and a minor peak corresponding to a dimer (FIG. 2f), whereas MBP-NCR247 purified from E. coli, grown on medium supplemented with 5-aminolevulinic acid (ALA) to increase the level of intracellular heme, migrated as a mixture of higher molecular weight species (FIG. 2g). MBP-NSR247 purified as a monomer, even after addition of ALA, implying that heme binding triggers multimerization (Extended FIG. 3b). Addition of a half molar equivalent of heme to purified MBP-NCR247 monomer results in a major dimer peak (FIG. 2h) but addition of equimolar heme yields a hexamer (FIG. 2i) and a small monomeric peak. Addition of even more heme leads to higher molecular weight multimers (FIG. 2j). Interestingly, the heme (and iron) to MBP-NCR247 ratio of monomer, dimer, hexamer, and multimer were ca. <0.2:1, 1:2, 1:1 and >1.3:1 respectively (FIGS. 2k and 2l). Mass photometry results upon addition of increasing concentration of heme to MBP-NCR247 monomers also indicated species with molecular weights corresponding to dimer, hexamer, or multimer (FIG. 8c).

Interestingly, negative staining of the hexameric MBP-NCR247-heme species revealed numerous examples of a flower-like structure with six petals (FIG. 2m; FIG. 8d). Taken together, these observations led us to propose a simple model, in which two NCR247 peptides initially bind a single heme on opposite sides. The resulting dimers then interact with additional heme at dimer-dimer interfaces to form hexamers (FIG. 2n), which can then form higher-order structures. As expected, NCR247 peptide can form multimers upon addition of heme and iron does not catalyze the formation of multimers (FIG. 8e). NCR247's special mode of interacting with heme would be expected to make both the iron and the porphyrin ring chemically inaccessible, an expectation supported by our observation that the intrinsic peroxidase activity of heme is quenched upon NCR247 binding (FIGS. 2o and 2p). It is unclear whether the recent report on the ability of some anti-microbial peptides to bind heme ~1000 fold less tightly than NCR247 and forming undefined assemblages is related to the heme binding properties of NCR247[21].

Physiological effects of NCR247-heme binding; BacA is an inner-membrane transporter that has a crucial role in uptake of NCR247 into the cytoplasm of S. meliloti[22, 23, 24]. A ΔbacA strain responds to iron starvation by increasing the expression of hmuP (a gene involved in iron uptake), similar to wildtype. However, there is very little change in expression of hmuP upon treatment with NCR247 (FIG. 3a), indicating that the iron starvation response caused by NCR247 is mediated in the cytoplasm of *S. meliloti*.

To demonstrate the ability of NCR247 to bind heme inside cells, we exploited the finding that heme quenches green fluorescence[25] by showing that the green fluorescence of FITC-labelled NCR247 can be effectively quenched by heme. As expected, the fluorescence of FITC-labelled NSR247 remains unquenched even after addition of excess heme (FIG. 9a). Cellular extracts made from *S. meliloti* grown in an ALA-supplemented medium (to raise intracellular heme) quenched the fluorescence of FITC-NCR247 more than the extracts made from cells grown with the iron chelator EDDHA (to lower intracellular heme). The fluorescence of FITC-labelled NSR247 remains the same in both conditions (FIG. 3b).

Because heme has a crucial role in maintaining iron homeostasis in rhizobial bacteria[26], the capacity of NCR247 to interact with free/labile intracellular heme and render it biologically inaccessible could account for the ability of NCR247 to induce a state of iron starvation. Iron homeostasis in *Sinorhizobium* and some related bacteria including *Rhizobium, Agrobacterium, Brucella*, and *Bartonella*[27, 28, 29] is controlled by two transcriptional regulators, Irr and RirA (FIG. 10)[26]. During iron-replete conditions, heme binding causes Irr to lose its DNA binding ability, thus causing de-repression of target genes involved in heme synthesis, iron storage, export, and, importantly, rirA[30]. After RirA is metalated to its fully active [4Fe-4S] bound form, it binds DNA and represses iron uptake genes to prevent further iron uptake[31, 9]. We hypothesized that intracellular heme sequestration by NCR247 causes Irr to stay active even under iron-replete conditions and repress the transcription of rirA, thus leading to an increase in transcription of iron import genes. Consistent with this hypothesis we found that rirA transcription was reduced upon NCR247 treatment (FIG. 3c); that NCR247-mediated increase in transcription of iron uptake genes (FIG. 3d and FIG. 9b-9f) and uptake of $^{55}$Fe were diminished in an irr deletion mutant (Δirr) compared to wild type *S. meliloti* (FIG. 3e); and that iron addition could only partially rescue the growth of NCR247-treated Δirr mutant (FIGS. 9g and 9h). The slight increase in expression of iron uptake genes in NCR247-treated Δirr compared to untreated Δirr may result from iron being redirected to replenish low levels of heme caused by heme sequestration rather than to metalate the Fe—S cluster of RirA and cause repression. In support of this model, a ΔrirA mutant had increased expression of hmuP and increased $^{55}$Fe uptake activity (FIGS. 9i and 9j) similar to NCR247-treated wildtype. Upon NCR247 treatment, a ΔrirA mutant showed improved growth when compared to wildtype in low iron and iron-sufficient conditions. However, at high iron conditions a ΔrirA mutant shows reduced growth rate and this worsens upon NCR247 treatment (FIGS. 9k and 9l) probably due to oxidative stress caused by excess iron.

*Rhizobia*-Legume symbiosis is a highly iron-requiring process[32, 33] because each molecule of the nitrogen-fixing enzyme nitrogenase requires 24-32 iron atoms[34, 35]. Iron is also an essential component of ferrodoxin and cytochromes, both of which are involved in respiration[32]. The iron uptake systems of roots are activated during nodulation[36], but how developing bacteroids increase iron import as they prepare to fix nitrogen has not been reported previously. In order to evaluate this further, we reanalysed a dataset from a laser-capture microdissection study coupled with RNA sequencing[37]. We found that the expression pattern of *S. meliloti* irr mRNA coincides with the expression pattern of NCR247 in various zones of the nodules (FIG. 3f). Additional support for our hypothesis comes from the observation that *S. meliloti* bacteroids isolated from *M. truncatula* nodules increase uptake of Fe$^{55}$ upon NCR247 treatment when compared with untreated bacteroids, and that this NCR247-mediated response was diminished in Δirr bacteroids isolated from nodules (FIG. 3g). Consistent with this, *M. sativa* and *M. truncatula* inoculated with Δirr *S. meliloti* had pale-coloured, small nodules, decreased shoot height and reduced numbers of nodules, when compared with plants inoculated with the wild-type *S. meliloti* implying ineffective symbiosis. Interestingly, since an active Irr can repress heme synthesis[38], the iron that is brought in could be directly utilized for incorporation into nitrogenase rather than for heme synthesis. Taken together, these observations suggest that NCR247 plays an important role in boosting iron import into the bacteroids during symbiosis by sequestering heme to override the usual iron homeostasis machinery of the bacterium.

Finally, we made a CRISPR knockdown of NCR247 in *M. truncatula* (A17) using *Agrobacterium rhizogenes* mediated hairy root transformation. 8/100 roots obtained from transforming two CRISPR constructs contained deletions in the NCR247 promoter region and 2/8 roots contained an additional substitution mutation in the putative peptidase recognition sequence (ALFLVV (SEQ ID NO:11) to ALFMVV (SEQ ID NO:12)). All 8 roots had small, white nodules, indicating that NCR247 is required for effective symbiosis (FIG. 3h, 3i). The rest of the 92 roots contained wildtype or heterogenic sequence and elicited pink nodules. These data indicate that the expression of NCR247 in plant nodules is critical to establish an effective symbiosis. Consistent with our model for NCR247 function, these small white nodules had a 4-fold reduction in iron content compared with normal nodules.

Sequence features of NCR247 enable heme binding; The features of the NCR247 sequence that enable it to bind and sequester heme so effectively seem to be rare, at least according to bioinformatics analysis. Sequences homologous to NCR247 were not found in the ca. 700 other NCR peptides of *M. truncatula* suggesting that the ability of NCR247 to bind heme with high-affinity may be unique among these peptides. We tested two NCR peptides that are reported to be essential for symbiosis (NCR211[3] and NCR169[4]) and the cationic antimicrobial peptide NCR035[2] for heme binding using UV-Vis spectrometry. None of these three peptides were able to bind heme as shown in FIG. 11a, indicating that they exert their symbiotic roles by different molecular mechanisms. We then performed a NCBI BLAST search with a cutoff of e-value less than 5 but did not find any related sequences in eukaryotes. We did identify one eukaryotic sequence by analysing *M. truncatula*'s close relative, *M. sativa* (alfalfa) whose sequences were not in the NCBI database. This revealed that *M. sativa* encodes an NCR247 ortholog, which has a 4-amino acid change compared to *M. truncatula* NCR247[39] (FIG. 11b). We show that a chemically synthesized *M. sativa* (alfalfa) NCR247 ortholog, binds heme with the same affinity using biolayer interferometry (FIG. 2e). Within the bacterial kingdom, our NCBI Blast search revealed that NCR247 has 83% similarity to a sequence within the C-terminal end of the protein DppD (FIGS. 11c and 11). DppD is the ATPase subunit of the inner membrane component of a heme ABC transporter that is required for heme iron utilization in *E. coli, Haemophilus influenzae* and *Mycobacterium tuberculosis*[40, 41, 42]. MBP-fused to a 20 amino acid peptide from C-terminal of *E. coli* DppD that is homologous to NCR247 purified as a reddish protein, and had signals corresponding to the presence of heme according to EPR (FIGS. 11e and 11f). Moreover, chemically synthesized peptide corresponding to the homologous region of DppD of *H. influenzae* readily bound heme in solution and exhibited a UV-Vis spectrum with Soret bands that were consistent with a heme binding protein (FIGS. 11g and 11h). However, this NCR247 related DppD peptide bound heme ~120 times less strongly than NCR247 (FIG. 2e).

Potential therapeutic applications of NCR247s heme sequestering property: Several features of NCR247's chemical and functional properties are interesting from a translational perspective. NCR247 binds heme with a $K_D$ of ca. 1 nM (FIG. 2e), which means that NCR247 can bind free heme, or labile heme loosely bound to proteins such as serum albumin ($K_D$ 40 μM)[43], without removing heme from the important heme-binding proteins hemoglobin ($K_D$ 0.01 μM) and the heme scavenger haempexin ($K_D$<1 μM)[44]. Also, the interaction of NCR247 cysteines with both axial positions of the iron in heme, followed by NCR247/heme oligomers forming aggregates, renders heme unreactive (FIGS. 2o and 2p). Further, the D-enantiomer of NCR247 binds heme as well as the L-enantiomer (FIG. 2e), but is resistant to proteolytic degradation. NCR247 is highly water soluble and is small which means that it can be synthesized chemically.[45] We tested L and D-NCR247 and found negligible cytotoxicity in mammalian cell line HEK-293 and did not detect haemolytic activities in a standard haemolysis assay (FIGS. 12a and 12b). Interestingly, as discussed in detail previously[46], the sequences of NCR peptides including NCR247 are related to antimicrobial peptides[47, 48] and share similarities such as pairs of cysteines with some conotoxins[49, 50]. Certain anti-microbial peptides and conotoxins have been used clinically.

L- and D-NCR247's special combination of heme-binding and sequestering characteristics suggest that these peptides and their derivatives might be exploited in a variety of clinical applications, including the following examples. First, NCR247's ability to sequester extracellular heme could block the growth of pathogens that are heme auxotrophs or require extra heme for some stage of their life cycle, such as egg-laying. Important pathogens that require exogenous heme include not only bacterial pathogens[51], but also a striking number of eukaryotic parasites[52] and worms[53], some of which infect significant fractions of the world's population but lack an effective treatment. First, in FIGS. 4a and b we tested this idea with naturally occurring bacterial heme auxotrophs *Hemophilus influenzae* (infections) and *Porphyromonas gingivalis* (periodontal disease), and found that NCR247 can prevent the growth of both of these pathogens. The D-enantiomer is more effective in killing than the L-enantiomer because of its protease resistance. Further, we showed that killing of these bacterial cells with NCR247 can be overcome by addition of heme supporting our hypothesis that sequestration of heme by NCR247 makes the heme unavailable to the pathogen. We also tested whether NCR247 could prevent the infectivity of apicomplexan parasite *Toxoplasma gondii* (toxoplasmosis). In FIG. 4c we show that 6 hr. treatment of *T. gondii* with L- or D-NCR247 leads to a massive reduction in the capacity of the parasite to form plaques on monolayers of human foreskin cell cultures[54]. The NSR247 variant, which does not bind heme, does not cause this phenotype even when used at high concentrations. Second, D- or L-NCR247 peptide attached to a solid support could be used to remove the free heme that accumulates in stored blood and is associated with the deleterious effects of large volume transfusions used in trauma-hemorrhage patients[55, 56, 57] or from the blood that is lysed during hemodialysis procedures for kidney disease, hemolytic diseases, etc[58]. FIGS. 12c and 12d show that NCR247 attached to magnetic beads can effectively pull down most of the free heme reported to be present in 42-day old blood[59]. Third, since heme sequestration by NCR247 would prevent the free heme from exerting its pro-oxidant, pro-inflammatory, and cytotoxic effects, it could potentially be used to relieve the severity of a wide range of human diseases and conditions that result in the release of a large amount of toxic free heme into the plasma, such as sepsis or malaria, hemolytic human diseases such as Sickle Cell Disease and β-thalassemia, or by Ischemia Reperfusion Injury[60, 61]. Interestingly, heme binding by human Aβ (1-42) amyloid peptides ($K_D$=140 nM) triggers a peroxidase activity and that has been postulated to be an important contributor to neurodegeneration associated with human Alzheimer's Disease, because of its ability to oxidize neurotransmitters[62, 63, 64] FIG. 4d shows the appearance of NCR247 specific peaks upon equimolar addition of NCR247 to the Aβ (1-42) amyloid peptide-heme complex and FIGS. 4e and 4f show that equimolar addition of NCR247 to the Aβ (1-42)-heme complex quenches its peroxidase activity. We note that these extremely limited experiments were designed only to demonstrate simple proofs of principle. Of course, future investigations of L and D-NCR247s possible clinical potential will require a great deal of additional research including the use of whole animal infection models, pharmacokinetics studies and evaluation of delivery mechanisms.

Discussion: We report that plant-produced peptide NCR247 can bind to and sequester heme, which in turn stimulates *rhizobia* to import the iron that is needed for nitrogenase functioning. This finding is the first report, to our knowledge, of a plant peptide modulating the metal homeostasis of symbiotic bacteria in order to benefit the plant. We suggest a model mechanism, which is consistent with our present data, for how a heme-sequestering NCR peptide like NCR247 can affect nitrogen fixation in specific legume-*rhizobium* symbioses' (FIG. 5). Our data demonstrate that NCR247 plays a critical active role in bacterial physiology by being imported into the bacterial cytoplasm where it directly interacts with the metabolite heme in a 1:1 manner that makes the heme and its iron biologically inaccessible. Cells then respond to the resulting physiological condition of heme deprivation by inducing all their RirA-regulated iron import genes even if they already have enough iron to satisfy their normal metabolic needs. We also show that this causes an increase in iron import that results in an elevated iron content of the cells. We present data indicating that NCR247 is essential for establishing an effective nitrogen fixing symbiosis. Although import of excess iron can result in oxidative stress in bacteria, that problem is avoided in the legume-*rhizobia* symbiosis by the expression of NCR247 in the microaerophilic nitrogen-fixing zone of the nodule. We suggest that when heme sequestration by NCR247 induces increased iron import into the *rhizobia*, the newly imported iron is made available for nitrogenase and other symbiotic purposes instead of being used for the synthesis of replacement heme because of the simultaneous down-regulation of the heme biosynthetic pathway.

Iron import into bacteroids during symbiosis is essential for nitrogenase activity, yet the identities of the *S. meliloti* transporters that function in planta remain unknown. Unlike *Bradyrhizobium japonicum*, where FeoB is the primary iron importer[66], *S. meliloti* lacks FeoB and so future studies are needed to identify the iron importer in its bacteroids. The gene expression patterns within various zones of nodules, where multiple NCR peptides are present, is more complex and does not fully overlap with what we observe in vitro upon treatment with NCR247 alone highlighting the need for more detailed studies of genes involved in iron homeostasis in various zones of nodules. Even though CRISPR knockdown of NCR247 in Medicago truncatula indicated its importance in symbiosis, a full transgenic knockout line will be required to further analyse its role in symbiosis.

NCR247 is a secreted peptide, so it is likely to be converted to an oxidized form in the endoplasmic reticulum of the host cell during its transport to the bacteroids[67]. The reducing environment of the bacteroid cytoplasm, as well as the symbiotically important glutaredoxins (SmGRX1)[68] and secreted plant thioredoxin (Trx1)[69] would reduce oxidized NCR247 and facilitate heme binding in the cytoplasm of bacteroids. Since oxidized NCR247 is not capable of binding heme (FIG. 13a), it seems unlikely that NCR247 would interact with heme in the peribacteroid space. Cytochromes are known to have a role in symbiotic respiration[70] but NCR247 cannot sequester cytochrome heme because of the covalent attachment (FIG. 13b). On the other hand, the $K_d$ of the high affinity binding site of Irr from R. leguminosorum is ~$1.0\pm0.1\times10^{-7}$ M (about 100-fold lesser than NCR247) which might enable NCR247 to sequester heme away from Irr.

Over the past decade, free heme has been implicated in the pathology of an extremely diverse variety of genetic and non-genetic human diseases and conditions and so heme has begun to attract attention as a target for therapeutic interventions[60]. In addition to the potential clinical applications briefly discussed above, heme is also involved in diseases caused by infectious agents that result in the release of free heme (e.g., malaria[72] and sepsis[73]), cancer[74], kidney disease[75], immune-mediated inflammatory diseases[76], cardiovascular disease[77], atherosclerosis[78], and neurodegeneration[79]. However, the challenge is that there has not been a "small molecule" (i.e., obtainable by chemical synthesis) that has the necessary characteristics for controlling or removing free heme. L- or D-NCR247 or their derivatives will be useful drugs in this capacity. Also, a striking number of important bacterial pathogens[51] and eukaryotic parasites[52] and worms[53], —some of which infect significant fractions of the world's population but lack an effective treatment—critically need to import heme from their environment to live. These pathogens can be controlled through use of L- and D-NCR247 and their derivatives such as those disclosed herein.

Growth conditions: Sinorhizhobium meliloti wild type strain R1\41021 and irr deletion mutant were routinely grown in LB medium supplemented with 2.5 mM $CaCl_2$) and 2.5 mM $MgSO_4$ (LBMC) in the presence of 200 µg/ml Streptomycin at 30° C. for 48 hours. When mentioned, S. meliloti were grown in minimal media (MM) with composition as described previously[81]. For making iron-free MM, $FeCl_3$ was omitted from the MM. Metal free water (VWR AMSTAR® ULTRA) was used to make MM. All flasks and tubes were washed with 6 M HCl and then with metal free water before autoclaving. Escherichia coli strains were routinely grown in LB medium at 37° C. When required 100 µg/ml of neomycin, 50 µg/ml of kanamycin, and 25 µg/ml of chloramphenicol were used.

Irr mutant generation:Irr (SMc00329) deletion mutant Δirr and RirA (SMc00785) deletion mutant (ΔrirA) was created as described previously[82]. In short, 500 bp flanking regions of irr or rirA (omitting the gene) were combined using overlap extension PCR and cloned into pK18MobSacB[83]. This was then transformed into S. meliloti 1021 using triparental mating and resulting colonies were selected in 5% Sucrose medium. The colonies that grew were then screened for loss of the pK18MobSacB plasmid by their inability to grow on Neomycin.

Growth curve: All growth curve experiments were performed in a Tecan SPARK 10M microplate reader using polystyrene flat bottomed, non-treated, sterile 96 well plates. Overnight cultures grown in LBMC were washed and were subcultured (1:100 dilution) in minimal medium supplemented with respective iron concentrations. The plates were programed to continuously shake at 150 rpm and temperature maintained at 30° C. Optical density was measured at 600 nm every 60 minutes.

ICP-MS: 200 µL of protein sample was mixed with 2 ml of 2% $HNO_3$ and ICP-MS was performed as described previously[84]. For bacterial samples, 1 ml of sample was spun down and the pellet was resuspended in 40 µL of 100% $HNO_3$ and heated at 98° C. for 1 hour. The supernatant of the solution was mixed with metal free water to make up to 2 mL and ICP-MS analysis was performed as described previously[84]. Same number of cells were spun down for protein analysis through BSA method and data were normalized to the amount of protein in each sample. For ICP-MS analysis of nodules same procedure was followed, except nodules were first crushed in PBS, portion of sample kept aside for protein quantification and then remaining was treated with $HNO_3$. Agilent ICP-MS instrumentation with MassHunter 4.4 was used to collect data.

Heme preparation: Hemin solutions were always prepared in 0.1 M NaOH and used within 30 min of preparation. 1:1000 and 1:500 dilution of the stock solution was made and stock concentration was measured by pyridine hemochrome assay as described previously[85] by measuring the absorption at 557 nm using the extinction coefficient of pyridine hemochromogen (34.7 $mM^{-1}$ $cm^{-1}$).

Mass spectrometry: LC-MS analyses were performed on an LC/MS quadrupole time-of-flight (Q-TOF) mass spectrometer from Agilent (Santa Clara, CA) with an electrospray ionization (ESI) source. The mass spectrometer was coupled with a High-Performance Liquid Chromatography system from Agilent (Santa Clara, CA). Agilent MassHunter™ Workstation Software-Data Acquisition Version B.05.01 was used to collect and Quantitative analysis Version B.07.00 was used to analyse the data. Heme samples were analyzed in positive mode using a COSMOSIL™ 5C18-AR-II Packed Column, 4.6 mm I.D.×150 mm C18 reverse phase column from Nacalai USA (San Diego, CA). The mobile phases were water (A) or acetonitrile (B). A linear gradient was run from 10% to 50% B over 30 min, at 100 µL/min. The ESI source parameters were: spray voltage, 4 kV; gas temperature, 340° C.; drying gas, 8 L/min; nebulizer, 20 psig; fragmentor, 175 V.

Biotinylation of heme: Hemin was biotinylated using the method exactly as described previouslyl[16]. Biotin hydrazide, DCC was purchased from Sigma. COSMOSIL™ 5C18-AR-II Packed Column, 4.6 mm I.D.×150 mm from Nacalai USA (San Diego, CA) was used to separate the products. LC-MS was used to verify the correct molecular weight (969.4 Da) of biotinylated heme (in which only one of the two propionate groups of protoheme was conjugated with biotin hydrazide) as described above.

Iron uptake assay: Radioactive $^{55}Fe$ uptake assays were performed as described previously[66] with some modifications. Cells were grown in LB to an $O.D._{600\,nm}$ of 0.2. 20 ml cultures were then spun down, and suspended in 20 ml minimal media with 5 µM FeSO$_4$ for 1 hour. 2 µM NCR247 and then 100 µM sodium ascorbate was added, and cells were incubated for additional 30 mins. At time 0, 1 µM$^{55}$FeCl$_3$ mixed with ascorbate was added. At given time points, 1 ml aliquots were taken and quenched in 3 ml of ice-cold quench buffer (0.1M Tris, 1 mM ascorbate, and 100 µM FeSO$_4$, pH 6.0). The cells were collected immediately after quenching on 0.45-µm filters, presoaked in quench buffer using a Millipore sigma 1225 vacuum filtration unit. The radioactive $^{55}$Fe content of the filters with cells was counted using a scintillation counter. Internalized $^{55}$Fe levels were normalized to the protein levels in the cell.

RNA isolation and qRT-PCR analysis: Cells were grown in LB until they reached an O.D.$_{600 \ nm}$ of 0.2. Then cells were spun down and suspended in minimal media with or without appropriate FeSO$_4$ concentrations for 1 hour. NCR247 was then added and 5 ml of appropriate cultures were spun down at given time intervals. Total RNA was extracted using Trizol™ (Thermo Fisher Scientific) method. Qiagen RNeasy™ kit was used to purify the RNA. On-column DNA removal was carried out using DNase I from NEB. 500 ng of each RNA sample was used to make cDNA using the iScript™ cDNA synthesis kit (Biorad). qRT-PCRs were performed as described previously[86]. The standard curve method was used for relative quantification. In short, a standard curve was generated for each gene of interest (including SMc00128) by setting up qpCR reactions to amplify increasing amounts of S. meliloti Rm 1021 genomic DNA. All the primer sets used resulted in a proportional dose response curve with $R^2 > 0.99$ confirming their efficiency. This curve was then used for extrapolating relative expression level of each gene of interest in a particular sample to obtain the starting quantities (SQ). This value is then normalized to the SQ values of SMc00128 obtained for respective sample. SMc00128 was used as a control gene since the expression levels did not change with iron and were used as a control in previous NCR247 studies' and as we demonstrated (data no shown). These normalized values are then expressed as an average of triplicates, with standard deviation (s.d.) represented by the error bars.

Peptides: All chemically synthesized peptides were purchased from Genscript. The purity of all peptides was >99% and verified by HPLC. The mass of each peptide was verified by MS analysis.

MBP-NCR247 protein purification: The coding sequence of NCR247 was ordered from gene synthesis (IDT). The amplified NCR247 sequence was cloned into plasmid pET28A downstream of the T7 promoter for expression of NCR247 with an N-terminal maltose-binding-protein (MBP) tag (Addgene™)[87]. This plasmid was then transformed into an E. coli BL21(DE3) strain harboring a pRARE™ plasmid (carries genes for co-expression of various rare tRNAs in E. coli to compensate for unfavorable codon usage[88]). Cells were grown to mid-exponential phase at 37° C. in LB media and expression of MBP-NCR247 was induced with 1 mM IPTG. Cells were then shifted to 16° C. and were grown overnight. Cells were collected using centrifugation at 8000 g for 30 min and re-suspended in a lysis buffer (20 mM Tris-HCl, 200 mM NaCl, 1 mM EDTA, complete Mini EDTA free protease inhibitor (Roche), pH 7.4). Cells were then lysed mechanically using a French press. Cell lysates were separated by centrifugation at 10000 g for 15 min and passed through a 0.45 µm filter. Proteins were purified using the MBPTrap™ HP column (GE) according to the manufacturer's instructions. Eluted protein was then loaded onto a size exclusion column (GE Hiload™ 16/60 Superdex™ 75 pg) equilibrated with Buffer B (20 mM Tris-HCl, 200 mM NaCl, 1 mM EDTA). Gel Filtration Standard (Biorad) was used to estimate the molecular weight of peaks. Unicorn 7 software was used to collect all FPLC data.

Negative staining and TEM: Freshly ionized carbon-coated grids were floated on a 10 µl drop of sample for 1 minute. The grid was washed with 5 drops of 2% acidic UA. Excess UA was drawn off with grade 50 Whatman filter paper. Grids were allowed to air dry and imaged with a Hitachi 7800 at 100 KV.

Fluorescence measurements: All fluorescence measurements were performed in 96-well black plates and measurements were taken in a Tecan Spark™ plate reader. For the peptide heme quenching experiment: 100 nM of FITC-NCR247 or FITC-NSR247 was added to the wells and increasing concentrations of molar equivalents of heme was added and fluorescence was noted. Fluorescent measurements from equal amount of FITC-NCR247 or FITC-NSR247 in the same buffer without any added heme was considered as 100%. For fluorescence quenching experiment from extracts: S. meliloti were grown in LBMC medium supplemented with 100 µM EDDHA or 20 µM ALA+100 µM FeSO$_4$. Cells were collected at saturation and resuspended in a lysis buffer (20 mM Tris-HCl, 200 mM NaCl, Mini EDTA free protease inhibitor (Roche), pH 7.4). Cells were then lysed mechanically using a French press. Cell lysates were separated by centrifugation at 10000 g for 15 min. The supernatant was then normalized for total protein using BCA method. 100 µg of extracts were loaded in 96-well black plates in triplicates and made up to final volume of 195 ul. 50 nM in 54, of either FITC-NCR247 or FITC-NSR247 were mixed with the extracts and fluorescent measurements were taken. Fluorescent measurements from equal amount of FITC-NCR247 or FITC-NSR247 in the same buffer was considered as 100%.

Peroxidase assay: Pierce TMB Substrate Kit was used to measure the peroxidase activity of the heme and equimolar NCR247 was added to heme according to the manufacturer's instructions. In short, 100 µL of TMB substrate solution (1:1 of TMB substrate and Peroxide solution) was added to 96 well black, polystyrene flat bottomed, non-treated, sterile plates. 5 µM heme or 5 µM NCR247+5 µM heme was added to the wells and the progression of the reaction was measured in a Tecan Spark™ plate reader. UV-Vis absorption values at 370 nm and 652 nm are noted every minute over a time period of 16 mins.

Mass photometry: All solutions were twice filtered with 0.22 µm syringe filters immediately prior to mass photometry measurements. Microscope coverslips (No. 1.5, 24×50 mm, Marienfeld) were cleaned by sequential submersion in Milli-Q™ water and 100% ethanol twice each followed by drying with optical lens paper. The final ethanol wash was dried with an air stream. Silicon gaskets were placed on clean microscope coverslips. Each measurement was acquired by adding 18 µL of storage buffer (20 mM Tris-HCl, 200 mM NaCl, 1 mM EDTA) to a gasket well. Following an autofocus stabilization, 2 µL of NCR247-MBP was added to the well to reach a final concentration of 1 µg/ml. Movies were recorded with a duration of 60 s at 1 kHz. A Contrast-to-mass calibration was performed using NativeMark™ Unstained Protein Standard. Data were gathered using the OneMP™ (Refeyn) with AcquireMP™ (Refeyn) 2.3.0. Movies were processed and analyzed using DiscoverMP™ (Refeyn) 2.3.0. Statistics were calculated after removing negative mass values from the data.

UV-VIS spectroscopy: All absorption spectra were collected in a Tecan Spark™ 10 M microplate reader using black polystyrene 96-well plates. Absorbance from 300 nm to 700 nm was recorded with a 5 nm interval after an initial shaking at 100 rpm for 15 secs. Heme binding to synthesized peptide: Water (pH 7.4) was used in all reactions and was first added to the wells. Peptides solubilized in water were added and then heme solubilized in 0.1 M NaOH was added, mixed thoroughly and measurements were taken immediately. Peptide and heme volume were kept to a maximum of 5 ul in volume. For all the absorption curves (except Extended FIG. 3a) 5 heme and 50 $\Phi$ of respective peptide was used. The same was also repeated with 0.1 M Tris buffer (pH 7.4) as a base buffer instead of water.

EPR spectroscopy: EPR spectra were collected in a Bruker EMX-Plus™ spectrometer at 10K with a Bruker/ColdEdge 4K waveguide cryogen-free cryostat. Xenon 1.1b.155 software was used to collect and process spectra. Spectra were recorded at 9.37 GHz with a modulation amplitude of 8 G, microwave power of 0.2518 mW, and a 100 kHz modulation frequency. A center field of 3850 G, a sweep time of 60s, and a sweep width of 7300 G were used. Each spectrum shown is an average of 10 scans.

Raman Spectroscopy: The Raman data was collected on a Horiba XploRa™ confocal Raman microscope using a 405 nm diode laser at 5.4 mW of power. The system is based on an Olympus BX41™ upright microscope. The 2400 grooves/mm blaze grating was used. An Olympus 50X long working distance objective with a NA of 0.5 was used. A 180-second exposure was used with an entrance slit of 200 µm and a confocal aperture of 500 µm. Two accumulations were averaged together for automatic cosmic ray removal. The denoise filter in Labspec™ 6 was used to smooth the data. A thermoelectric cooled (−70° C.), Syncerity camera was used to collect the spectra. A uEye™ camera by IDS Imaging was used for the optical image of the sample.

Biolayer interferometry: Biolayer interferometry was carried out using a ForteBio Octet RED96™ biolayer interferometer, following the manufacturer's instructions for a standard kinetic assay. Streptavidin-coated biosensor tips were incubated in 200 µl assay buffer (Water [pH 7.4]), each for 60s. Then biotinylated heme (or NCR247 in the case of Fe(III) PPIX dimethyl ester chloride) was loaded onto each biosensor tip at the defined concentration until the binding signal reached a value of >1.4. Biosensor tip loading was followed by incubation in assay buffer for 60s. Association between the ligand-heme and the analyte-various variants of NCR247 (Increasing concentrations in assay buffer) was observed over a time frame of ~116 s, in assay buffer. To stop binding kinetics for dissociation, the biosensor tips were placed back into assay buffer not containing any analyte, for 120 s. Curves were fit with Global fit analysis and Data analysis and $K_D$ calculation was performed using Fortebio™ data analyses 8.2 software as described previously[89].

Oxalic acid assay for measurement of heme: Total amount of heme in protein and plasma samples was measured by Oxalic acid method as described previously[90, 91] To 50 µL of protein sample, 450 µL of 20 mM oxalic acid was added and stored at 4° C. overnight. Then 500 µL of 2 M Oxalic acid was added and the sample was split into two. One of the samples was heated to 98° C. for 30 mins. An unheated sample was used as a blank. 96-well black plates and measurements were taken in a Tecan Spark™ plate reader. The porphyrin fluorescence (excitation 400 nm, emission 620 nm) was measured for each sample. The standard curve was determined using the same method for various concentrations of hemin chloride.

Cell viability assays for *H. influenza* and *P. gingivalis*: *Haemophilus influenzae* Rd [KW20] was obtained from ATCC (51907). Standard growth and culturing techniques were followed as described previously[92]. Cultures were grown in Brain Heart Infusion broth (BHI) supplemented with 7.5 µM of hemin and 2 µg/ml NAD with or without the addition of peptide for 24 hours. The number of viable cells for every reaction mixture was then determined by serially diluting and spotting 10-µl aliquots in triplicates on BHI agar plates supplemented with 15 µM hemin and 3 µM NAD. *Porphyromonas gingivalis* 2561 was obtained from ATCC (33277). Pre-reduced, anaerobically sterilized *Brucella* Broth and BRU—*Brucella* Blood Agar—were purchased from Anaerobe systems (CA, USA). They were opened just before use. Static cultures and plates were incubated at 37° C. in an incubation chamber from BD GasPak™ EZ Container Systems. Anaerobic conditions were maintained by using BD BBL $CO_2$ gas generators and BD BB GasPak™ $CO_2$ indicators. Cultures were grown anaerobically in *Brucella* Broth with or without addition of peptides for 48 hours and viable cells for every reaction mixture were then determined by serially diluting and spotting 10-µl aliquots in triplicates on *Brucella* Blood Agar.

Pull-down assay of heme from stored blood: Expired units of whole blood were obtained from the American Red Cross through a local hospital, and plasma was separated from whole blood by centrifugation for 10 minutes at 1500×g in 10 ml BD Vacutainer Plastic Blood Collection Tubes with $K_2$EDTA. The supernatant was collected and divided into several 500 aliquots. Washed Streptavidin T1 MyOne™ Dynabeads™ (Invitrogen) were incubated with excess N-terminal Biotin-labeled NCR247 for 30 mins. After being washed according to the manufacturer's protocol, 300 µL of plasma was added and further incubated at 4° C. with rotation for 2 hours. Beads were then collected by using a magnetic stand (Dynamag-2™ Life technologies) and washed with 300 µL PBS 3 times. The beads were then resuspended in 50 of 20 mM Oxalic acid and porphyrin content was measured as mentioned above. Beads not incubated with Biotin-NCR247 were used as a control and were subjected to the same procedure. Unheated sample from the Oxalic acid method was used as blank for the respective heated samples. Original plasma was serially diluted in PBS and the porphyrin content was measured by the same oxalic acid method.

Parasite and host cell culture: *T. gondii* parasites (strain RH, ATCC 50838) were grown in human foreskin fibroblasts (HFFs) maintained in DMEM (GIBCO) supplemented with 3% inactivated fetal calf serum (IFS) and 10 µg/mL gentamicin (Thermo Fisher Scientific), referred to as D3. Where noted, DMEM supplemented with 10% IFS and 10 µg/mL gentamicin was used, referred to as D10.

Plaque Assays: Freshly lysed parasites were filtered through 5 µm filters and spun down at 1000×g and 18° C. for 10 min. Parasites were resuspended to 6E6 parasites/mL in Fluorobrite™ media supplemented with 3% IFS. Parasites were incubated with either peptide or vehicle for 6 hours at 37° C. and 5% CO2. Parasites were then spun down, washed once in 2 mL of Fluorobrite™ supplemented with 3% IFS, and resuspended in 1 mL of media. 2000 parasites were inoculated into each well of 6-well plates of HFFs maintained in D10 and allowed to grow undisturbed for 9 days. Plates were washed with PBS and fixed for 10 min at room temperature with 100% ethanol. Monolayers were visualized by staining for 5 min at room temperature with crystal violet solution, followed by two washes with PBS, one wash with water, and drying overnight.

Plant growth and inoculation: Three-day-old alfalfa or *M. truncatula* seedlings were inoculated with *S. meliloti* strains 1 ml $OD_{600}$ of 0.05 in sterile water on Jensen's agar exactly as described previously[93]. *S. meliloti* strains were grown in minimal medium supplemented with 5 μM $FeSO_4$ prior to inoculation. Plants were grown at 25° C. with a light/dark cycle of 16/8 h, respectively.

Bacteroid isolation: Bacteroids were isolated from 28-day old nodules using the Percoll gradient (Sigma) method described previously[94, 95]. 50 nodules were removed from plants inoculated with Wild type or Δirr and immediately washed in wash buffer (0.35 M mannitol, 3 mM $MgSO_4$, and 25 mM MES-KOH pH 7.0). After surface sterilization with 95% ethanol, nodules were crushed and filtered by miracloth (Millipore) assay. The filtrate was layered on [1 ml 80% (v/v):3 ml 60% (v/v):1 ml 30% (v/v)] prepared in wash buffer and centrifuged for 4000 g at 4° C. for 15 mins. The bacteroids were then diluted in wash buffer and vortexed for 1 min for release from the peribacteroid units. After the release of bacteroids, they were immediately used for iron uptake assay.

Cytotoxic activity assay: Human embryonic kidney (HEK-293-ATCC-CRL-1573) cell lines were cultured in Dulbecco's Modified Eagle Medium (DMEM) supplemented with 10% Fetal Bovine Serum (FBS). When cells reached $10^4$-$10^5$ cells per well, cells were supplemented with fresh DMEM without FBS, and then treated with 100 μM of NCR247 (L and D). After treatment for 24 h, MTT (Abeam, United Kingdom) stock solution was added to each well at a final concentration of 500 μg/mL and incubated in the dark for 4 h at 37° C. The absorbance at 570 nm was measured in the Tecan plate reader.

Haemolysis assay: Standard methods of hemolysis assay as previously published was followed[96]. Human red blood cells (hRBC) were washed three times with phosphate-buffered saline (PBS: 10 mM $Na_2HPO_4$, 1.76 mM $K_2HPO_4$, pH 7.4, containing 173 mM NaCl, and 2.7 mM KCl). Two-fold serial dilutions of the peptide solutions were then added to 50 μl aliquots of hRBC in PBS to adjust a final volume to 100 μl and hRBC concentration to 4% (v/v) in each well of a 96-well plate. The suspension was incubated for 1.5 h at 37° C. under stirring at 1000 rpm. The plates were centrifuged at 2000 g for 5 min. Supernatant aliquots of 50 μl were transferred into flat-bottomed 96-well microplates, and the release of hemoglobin was monitored by measuring the absorbance at 405 nm in a microplate reader. hRBC in PBS (0% lysis control) and 0.1% Triton X-100 (100% lysis control) were used as negative and positive controls, respectively. Hemolytic activity was expressed as a percentage of hemolysis calculated according to the following equation: Hemolysis (%)=($OD_{405nm}$ sample—$OD_{405nm}$ 0% lysis control)/($OD_{405nm}$ 100% lysis control–$OD_{405nm}$ 0% lysis control)*100.

CRISPR vector generation: gRNAs were designed manually and BLAST search was done through phytozome to avoid overlap with other exons. ATUM program was run to confirm the validity of gRNAs. Primers were then cloned into pDirect22c™ by golden gate cloning using NEBridge™ golden gate assembly kit. The sequenced vectors were then electroporated to *Agrobacterium rhizogenes* for hairy root transformation.

Hairy root transformation: Hairy root transformation was performed as described previously[98]. Standard CTAB method was used for DNA extraction (OPS diagnostics—CTAB protocol for isolating DNA from plant tissues). The sequences were verified using PCR amplification of ~1000 bp region around the gene, followed by Sanger sequencing.

Statistical Analysis: Details of statistical analyses are presented in the figure legends. Statistical analysis was performed on Prism™ software (GraphPad 6.01) using two-way ANOVA with multiple comparisons for repeated measurements.

Example 2

Since NCR247 treatment leads to gene expression change in several genes of the CtrA regulon, we investigated the CtrA regulon and the cell division inhibition role of NCR247. As known previously in a synchronized S. meliltoi culture, treatment with 4 uM of L-NCR247 leads to cell division inhibition as measured by flow cytometry analysis. However, we did not observe much of this inhibition in D-NCR247 treated cells. In addition, this phenotype is retained in a peptide transporter bacA mutant indicating cell division inhibition happens due to protein-peptide interaction outside the cytoplasm. As previously noted, L-NCR247 also results in inhibition of assembly of the Z-ring where as when treated with D-NCR247 there was less inhibition of formation of Z-ring. Data quantified using GFP labeled FtsZ and fluorescent microscopy to count number of cells exhibiting Z-ring during division. We observed the same trend in gene expression analysis of genes in the ctrA regulon upon treatment with L and D-NCR247. q-RT PCR analysis of gene expression shows L-NCR247 lowers the expression of CtrA while D-NCR247 does to a lower extent. See FIGS. 14-16.

We investigated the expression of genes in the FeuP and ExoS regulon. Both of these are two-component systems that sense environmental signals in periplasm. Similar to ctrA regulon, we find that both FeuP (figure A) and Exos (figure B) regulated genes are increased in expression upon L-NCR247 treatment and we did not notice any increase in D-NCR247 treated cells and this effect is similar in a bacA mutant implying that induction of genes in FeuP and ExoS regulon were also due to chiral interaction of NCR247 outside the cytoplasm. See FIG. 17.

Figure 18A:
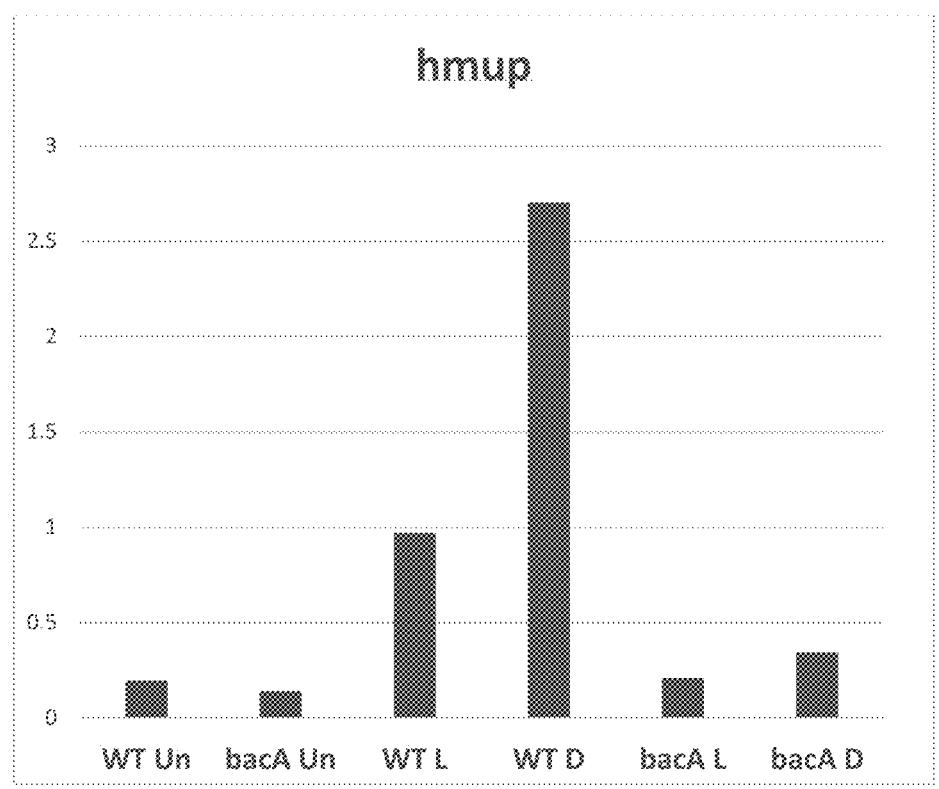
Figure 18B:
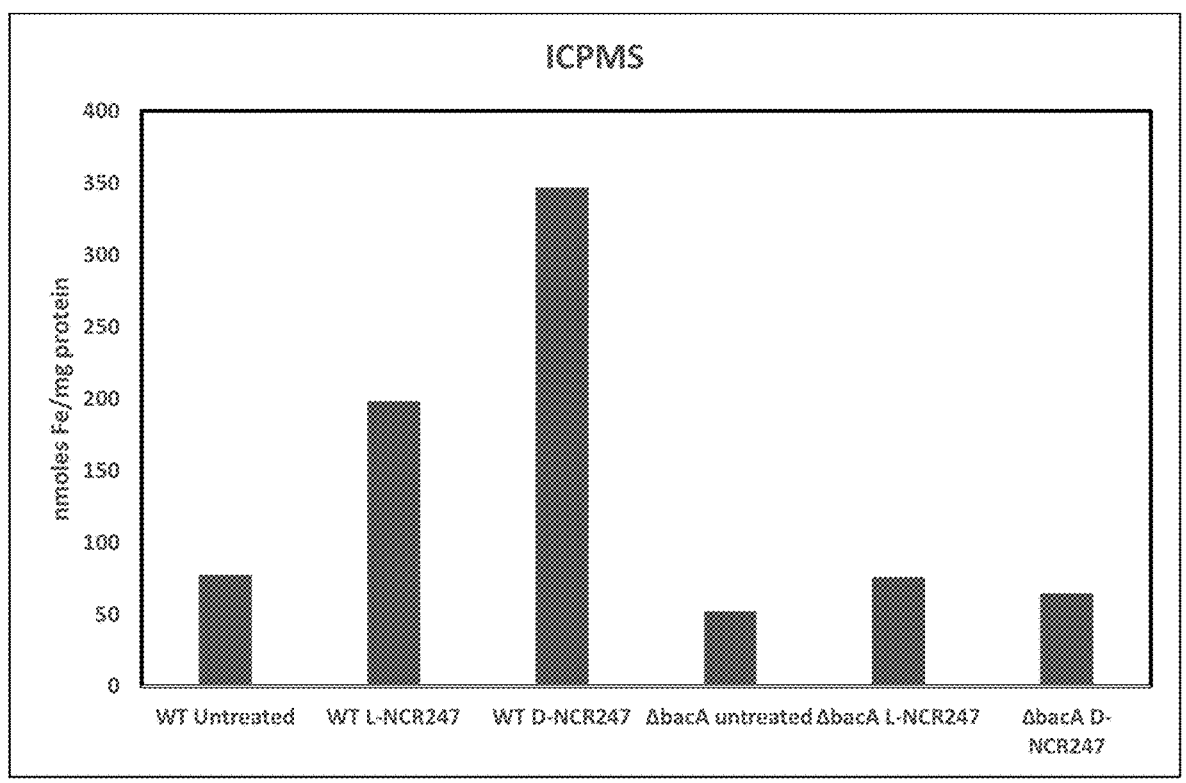
Figure 19:
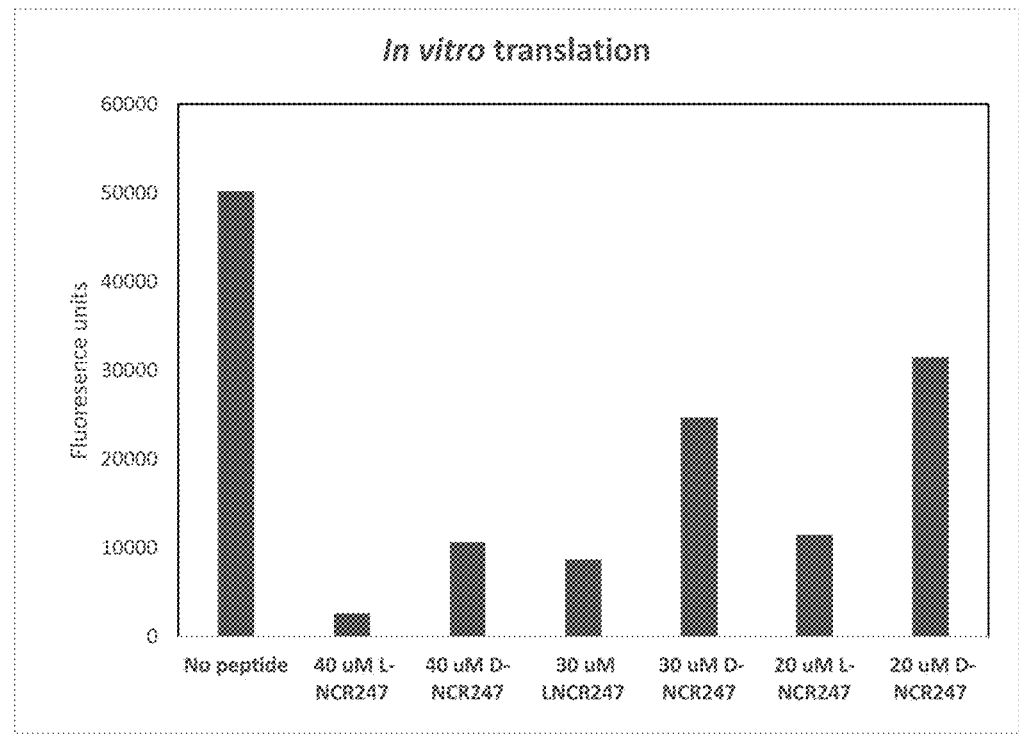
Figure 19:
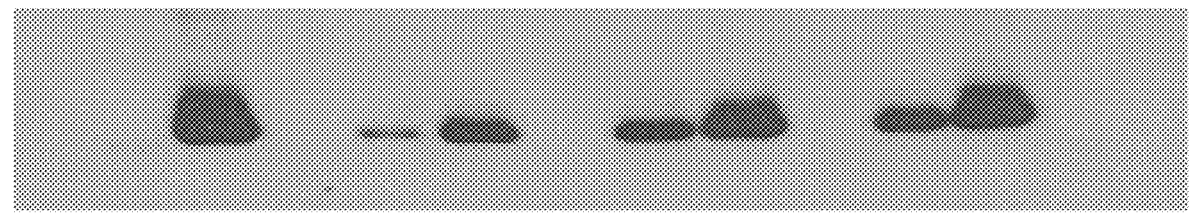

NCR247 binds heme and this heme sequestration leads to an iron starvation response in *S. meliloti* and this happens in the cytoplasm since a bacA mutant is defective in inducing iron import genes. In vitro D-NCR247 is capable of binding heme equally well. Interestingly we notice that there is further increase in transcription of iron import genes as measured by qRT-PCR (Figure—A), and ultimately an increase in iron content of the cells when treated with D-NCR247 when compared to L-NCR247 as measured by ICPMS (Figure—B). This suggests that L-NCR247 undergoes either degradation or modification at least in vitro after entering the cytoplasm whereas D-NCR247 is stable and exhibits more heme-binding activity. See. FIG. 18.

Interaction of NCR247 with ribosomal machinery leads to modification in translational capability. To see if this is due to chiral interaction, we performed in-vitro translation assay and used GFP production and measured fluorescence as a read out. We also performed a western blot to measure the amount of GFP produced using Anti-GFP antibody. Indeed there was inhibition of production of GFP by L-NCR247 and but this effect was less pronounced in D-NCR247 treatment. This shows that inhibition of translation is partly due to chiral interactions and opens the possibility of NCR247's role in binding to other proteins inside cytoplasm in addition to the binding of heme. See FIG. 19.

In further studies (data not shown), we demonstrated that (a) NCR247 inhibits the growth of *Sinorhizobium meliloti* (bacteriostatic effect), with increasing amounts of NCR247 cause an increasing reduction in growth rate. (b) NCR247 causes a reduction in the number of S. meliloti cells when incubated for 24 hours and plated in non-selective medium (Cell killing or bactericidal effect). (c) NCR247 binds heme with typical absorption peaks at 366 nm and ~450 nm for NCR247+Heme, when NCR247 was added to an equal amount of heme and the curve was measured over a period of 10 hours. (d) NSR247 very modestly inhibits the growth of Sinorhizobium meliloti (bacteriostatic effect). Increasing amounts of NSR247 causes a modest reduction in growth rate. (e) NSR247 causes no reduction in number of S. meliloti cells when incubated for 24 hours and plated in non selective medium (Cell killing or bactericidal effect). (f) NSR247 does not binds heme and so the absorption peaks at 366 nm and ~450 nm for NCR247+Heme is missing. Only peaks typical of free heme were seen when NSR247 was added to an equal amount of heme and the curve was measured over a period of 10 hours. (g) NCR247 mutant (C-terminal RRR mutated to AAA) does not inhibit the growth of Sinorhizobium meliloti (no bacteriostatic effect), and increasing amounts of the NCR247 mutant does not cause any reduction in growth rate. (h) The NCR247 mutant causes no reduction in number of S. meliloti cells when incubated for 24 hours and plated in non selective medium (No cell killing or bactericidal effect). (i) The NCR247 mutant binds heme with typical absorption on peaks at 366 nm and ~450 nm for NCR247+Heme, when the NCR247 mutant was added to equal amount of heme and the curve was measured over a period of 10 hours. See Table 1.

TABLE 1

| Peptide | Concentration | Cell death in 24 hours |
|---|---|---|
| NCR247 | 6 uM | 10000 fold decrease in cell number |
| NSR247 | 6 uM | No cell death observed |
| NCR247 (RRR to AAA mutant) | 6 uM | No cell death observed |

REFERENCES

1. Gibson, K. E., Kobayashi, H. & Walker, G. C. Molecular determinants of a symbiotic chronic infection. *Annu. Rev. Genet.* 42, 413-441 (2008).
2. Van De Velde, W. et al. Plant peptides govern terminal differentiation of bacteria in symbiosis. *Science (80-.).* 327, 1122-1126 (2010).
3. Kim, M. et al. An antimicrobial peptide essential for bacterial survival in the nitrogen-fixing symbiosis. *Proc. Natl. Acad. Sci. U.S.A* 112, 15238-15243 (2015).
4. Horvath, B. et al. Loss of the nodule-specific cysteine rich peptide, NCR169, abolishes symbiotic nitrogen fixation in the *Medicago truncatula* dnf7 mutant. doi:10.1073/pnas.1500777112.
5. Mikuláss, K. R. et al. Antimicrobial nodule-specific cysteine-rich peptides disturb the integrity of bacterial outer and inner membranes and cause loss of membrane potential. *Ann. Clin. Microbiol. Antimicrob.* 15, 43 (2016).
6. Farkas, A. et al. *Medicago truncatula* symbiotic peptide NCR247 contributes to bacteroid differentiation through multiple mechanisms. *Proc. Natl. Acad. Sci. U.S.A* 111, 5183-5188 (2014).
7 Penterman, J. et al. Host plant peptides elicit a transcriptional response to control the *Sinorhizobium meliloti* cell cycle during symbiosis. doi:10.1073/pnas.1400450111.
8. Shabab, M. et al. Disulfide cross-linking influences symbiotic activities of nodule peptide NCR247. doi:10.1073/pnas.1610724113.
9. Chao, T. C., Buhrmester, J., Hansmeier, N., Pühler, A. & Weidner, S. Role of the regulatory gene rirA in the transcriptional response of *Sinorhizobium meliloti* to iron limitation. *Appl. Environ. Microbiol.* 71, 5969-5982 (2005).
10. Shabab, M. et al. Disulfide cross-linking influences symbiotic activities of nodule peptide NCR247. *Proc. Natl. Acad. Sci. U.S.A* 113, 10157-10162 (2016).
11. Penterman, J. et al. Host plant peptides elicit a transcriptional response to control the *Sinorhizobium meliloti* cell cycle during symbiosis. *Proc. Natl. Acad. Sci. U.S.A* 111, 3561-3566 (2014).
12. Barr, I. et al. DiGeorge Critical Region 8 (DGCR8) is a double-cysteine-ligated heme protein. *J. Biol. Chem.* 286, 16716-16725 (2011).
13. Kupke, T., Klare, J. P. & Brügger, B. Heme binding of transmembrane signaling proteins undergoing regulated intramembrane proteolysis. *Commun. Biol.* 3, 1-16 (2020).
14. Barr, I. et al. Ferric, not ferrous, heme activates RNA-binding protein DGCR8 for primary microRNA processing. *Proc. Natl. Acad. Sci. U.S.A* 109, 1919-1924 (2012).
15. Girvan, H. M. et al. Analysis of Heme Iron Coordination in DGCR8: The Heme-Binding Component of the Microprocessor Complex. *Biochemistry* 55, 5073-5083 (2016).
16. Ishida, M., Dohmae, N., Shiro, Y. & Isogai, Y. Synthesis of biotinylated heme and its application to panning heme-binding proteins. *Anal. Biochem.* 321, 138-141 (2003).
17. Kuhl, T. et al. Analysis of Fe(III) heme binding to cysteine-containing heme-regulatory motifs in proteins. *ACS Chem. Biol.* 8, 1785-1793 (2013).
18. Shimizu, T. Binding of cysteine thiolate to the Fe(III) heme complex is critical for the function of heme sensor proteins. *J. Inorg. Biochem.* 108, 171-177 (2012).
19. Li, T., Bonkovsky, H. L. & Guo, J. T. Structural analysis of heme proteins: Implications for design and prediction. *BMC Struct. Biol.* 11, 1-13 (2011).
20. Brewitz, H. H. et al. Heme interacts with histidine- and tyrosine-based protein motifs and inhibits enzymatic activity of chloramphenicol acetyltransferase from *Escherichia coli*. *Biochim. Biophys. Acta-Gen. Subj.* 1860, 1343-1353 (2016).
21. Juhász, T. et al. Interplay between membrane active host defense peptides and heme modulates their assemblies and in vitro activity. *Sci. Reports* 11, 18328 (123AD).
22. Ferguson, G. P., Roop, R. M. & Walker, G. C. Deficiency of a *Sinorhizobium meliloti* bacA mutant in alfalfa symbiosis correlates with alteration of the cell envelope. *J. Bacteriol.* 184, 5625-5632 (2002).
23. Guefrachi, I. et al. *Bradyrhizobium* BclA Is a Peptide Transporter Required for Bacterial Differentiation in Symbiosis with Aeschynomene Legumes. 28, (2015).
24. Marlow, V. L. et al. Essential role for the BacA protein in the uptake of a truncated eukaryotic peptide in *Sinorhizobium meliloti*. *J. Bacteriol.* 191, 1519-1527 (2009).
25. Takeda, S., Kamiya, N. & Nagamune, T. A novel protein-based heme sensor consisting of green fluorescent protein and apocytochrome b562. *Anal. Biochem.* 317, 116-119 (2003).
26. O'Brian, M. R. Perception and Homeostatic Control of Iron in the *Rhizobia* and Related Bacteria. *Annu. Rev. Microbiol.* 69, 229-245 (2015).

27. Hibbing, M. E. & Fuqua, C. Antiparallel and interlinked control of cellular iron levels by the Irr and RirA regulators of *Agrobacterium tumefaciens*. *J. Bacteriol.* 193, 3461-3472
28. Zhang, H. et al. Insights into irr and rira gene regulation on the virulence of *brucella melitensis* m5-90. *Can. J. Microbiol.* 66, 351-358 (2020).
29. Costa, D., Amarelle, V., Valverde, C., O'Brian, M. R. & Fabiano, E. The Irr and RirA proteins participate in a complex regulatory circuit and act in concert to modulate bacterioferritin expression in Ensifer *meliloti* 1021. *Appl. Environ. Microbiol.* 83, 895-912 (2017).
30. Singleton, C. et al. Heme-responsive DNA binding by the global iron regulator Irr from *rhizobium leguminosarum*. *J. Biol. Chem.* 285, 16023-16031 (2010).
31. Pellicer Martinez, M. T. et al. Sensing iron availability via the fragile [4Fe-4S] cluster of the bacterial transcriptional repressor RirA †. (2017) doi:10.1039/c7sc02801f.
32. Brear, E. M., Day, D. A. & Smith, P. M. C. Iron: An essential micronutrient for the legume-*rhizobium* symbiosis. Front. *Plant Sci.* 4, (2013).
33. González-Guerrero, M., Matthiadis, A., Sáez, Á. & Long, T. A. Fixating on metals: New insights into the role of metals in nodulation and symbiotic nitrogen fixation. Front. *Plant Sci.* 5, 45 (2014).
34. Seibert, M., Lien, S., Weaver, P. F. & Janzen, A. F. Photobiological Production of Hydrogen and Electricity. 273-229 (1981) doi:10.1016/b978-0-08-025388-6.50039-8.
35. Einsle, O. et al. Nitrogenase MoFe-protein at 1.16 Å resolution: A central ligand in the FeMo-cofactor. *Science* (80-.). 297, 1696-1700 (2002).
36. Terry, R. E., Soerensen, K. U., Von Jolley, D. & Brown, J. C. The role of active *Bradyrhizobium japonicum* in iron stress response of soybeans. *Plant Soil* 130, 225-230 (1991).
37. Roux, B. et al. An integrated analysis of plant and bacterial gene expression in symbiotic root nodules using laser-capture microdissection coupled to RNA sequencing. *Plant J.* 77, 817-837 (2014).
38. Hamza, I., Chauhan, S., Hassett, R. & O'Brian, M. R. The bacterial irr protein is required for coordination of heme biosynthesis with iron availability. *J. Biol. Chem.* 273, 21669-21674 (1998).
39. Montiel, J. et al. Morphotype of bacteroids in different legumes correlates with the number and type of symbiotic NCR peptides. doi:10.1073/pnas.1704217114.
40. Létoffé, S., Delepelaire, P. & Wandersman, C. The housekeeping dipeptide permease is the *Escherichia coli* heme transporter and functions with two optional peptide binding proteins. *Proc. Natl. Acad. Sci. U.S.A* 103, 12891-12896 (2006).
41. Morton, D. J., Seale, T. W., Vanwagoner, T. M., Whitby, P. W. & Stull, T. L. The dppBCDF gene cluster of *Haemophilus influenzae*: Role in heme utilization. *BMC Res. Notes* 2, 166 (2009).
42. Mitra, A., Ko, Y. H., Cingolani, G. & Niederweis, M. Heme and hemoglobin utilization by *Mycobacterium tuberculosis*. *Nat. Commun.* 10, 1-14 (2019).
43. Kamal, J. K. A. & Behere, D. V. Binding of heme to human serum albumin: Steady-state fluorescence, circular dichroism and optical difference spectroscopic studies. Indian *J. Biochem. Biophys.* 42, 7-12 (2005).
44. Hrkal, Z., Vodrážka, Z. & Kalousek, I. Transfer of Heme from Ferrihemoglobin and Ferrihemoglobin Isolated Chains to Hemopexin. *Eur. J. Biochem.* 43, 73-78 (1974).
45. Wang, T. et al. Heme Sequestration as an Effective Strategy for the Suppression of Tumor Growth and Progression. *Mol. Cancer Ther.* 20, 2506-2518 (2021).
46. Lima, R. M., Kylarová, S., Mergaert, P. & Kondorosi, É. Unexplored Arsenals of Legume Peptides With Potential for Their Applications in Medicine and Agriculture. *Front. Microbiol.* 11, (2020).
47. Srivastava, S. et al. Cysteine-rich antimicrobial peptides from plants: The future of antimicrobial therapy. *Phytotherapy Research* vol. 35 256-277 (2021).
48. Lehrer, R. I. & Ganz, T. Endogenous vertebrate antibiotics. Defensins, protegrins, and other cysteine-rich antimicrobial peptides. *Ann. N. Y. Acad. Sci.* 797, 228-239 (1996).
49. Halai, R. & Craik, D. J. Conotoxins: Natural product drug leads. *Natural Product Reports* vol. 26 526-536 (2009).
50. Layer, R. T. & McIntosh, J. M. Conotoxins: Therapeutic potential and application. *Marine Drugs* vol. 4 119-142 (2006).
51. Richard, K. L., Kelley, B. R. & Johnson, J. G. Heme uptake and utilization by gram-negative bacterial pathogens. *Front. Cell. Infect. Microbiol.* 9, 81 (2019).
52. Kořený, L., Obornik, M. & Lukeš, J. Make It, Take It, or Leave It: Heme Metabolism of Parasites. *PLoS Pathog.* 9, (2013).
53. Perner, J., Gasser, R. B., Oliveira, P. L. & Kopáček, P. Heme Biology in Metazoan Parasites—'The Bright Side of Heme'. *Trends Parasitol.* 35, 213-225 (2019).
54. Bergmann, A. et al. *Toxoplasma gondii* requires its plant-like heme biosynthesis pathway for infection. *PLoS Pathog.* 16, e1008499 (2020).
55. Wagener, B. M. et al. Role of heme in lung bacterial infection after trauma hemorrhage and stored red blood cell transfusion: A preclinical experimental study. *PLoS Med.* 15, (2018).
56. Lee, J. S. & Kim-Shapiro, D. B. Stored blood: How old is too old? *J. Clin. Invest.* 127, 100-102 (2017).
57. Graw, J. A. et al. Haptoglobin or hemopexin therapy prevents acute adverse effects of resuscitation after prolonged storage of red cells. *Circulation* 134, 945-960 (2016).
58. Ofori-Acquah, S. F. et al. Hemopexin deficiency promotes acute kidney injury in sickle cell disease. *Blood* 135, 1044-1048 (2020).
59. Gouveia, Z. et al. Characterization of plasma labile heme in hemolytic conditions. *FEBS J.* 284, 3278-3301 (2017).
60. Immenschuh, S., Vijayan, V., Janciauskiene, S. & Gueler, F. Heme as a target for therapeutic interventions. *Front. Pharmacol.* 8, 146 (2017).
61. Smith, A. & McCulloh, R. J. Mechanisms of heme toxicity in haemolysis and protection by the heme-binding protein, haemopexin. *ISBT Sci. Ser.* 12, 119-133 (2017).
62. Seal, M., Ghosh, C., Basu, 0. & Dey, S. G. Cytochrome c peroxidase activity of heme bound amyloid β peptides. *J. Biol. Inorg. Chem.* 21, 683-690 (2016).
63. Ghosh, C., Seal, M., Mukherjee, S. & Ghosh Dey, S. Alzheimer's Disease: A Heme-Aβ Perspective. *Accounts of Chemical Research* vol. 48 2556-2564 (2015).
64. Atamna, H. & Boyle, K. Amyloid-β peptide binds with heme to form a peroxidase: Relationship to the cytopathologies of Alzheimer's disease. *Proc. Natl. Acad. Sci. U.S.A* 103, 3381-3386 (2006).
65. Downie, J. A. & Kondorosi, E. Why Should Nodule Cysteine-Rich (NCR) Peptides Be Absent From Nodules of Some Groups of Legumes but Essential for Symbiotic N-Fixation in Others? *Front. Agron.* 3, 42 (2021).

66. Sankari, S. & O'Brian, M. R. The *Bradyrhizobium japonicum* ferrous iron transporter FeoAB is required for ferric iron utilization in free living aerobic cells and for symbiosis. *J. Biol. Chem.* 291, 15653-15662 (2016).

67. Sevier, C. S. & Kaiser, C. A. Formation and transfer of disulphide bonds in living cells. *Nat. Rev. Mol. Cell Biol.* 3, 836-847 (2002).

68. Benyamina, S. M. et al. Two *Sinorhizobium meliloti* glutaredoxins regulate iron metabolism and symbiotic bacteroid differentiation. *Environ. Microbiol.* 15, 795-810

69. Ribeiro, C. W. et al. Regulation of Differentiation of Nitrogen-Fixing Bacteria by Microsymbiont Targeting of Plant Thioredoxin sl. *Curr. Biol.* 27, 250-256 (2017).

70. Delgado, M. J., Bedmar, E. J. & Downie, J. A. Genes involved in the formation and assembly of rhizobial cytochromes and their role in symbiotic nitrogen fixation. *Adv. Microb. Physiol.* 40, 191-231 (1998).

71. Farkas, A. et al. *Medicago truncatula* symbiotic peptide NCR247 contributes to bacteroid differentiation through multiple mechanisms. *Proc. Natl. Acad. Sci. U.S.A* 111, 5183-5188 (2014).

72. Seixas, E. et al. Heme oxygenase-1 affords protection against noncerebral forms of severe malaria. *Proc. Natl. Acad. Sci. U.S.A* 106, 15837-15842 (2009).

73. Larsen, R. et al. A central role for free heme in the pathogenesis of severe sepsis. *Sci. Transl. Med* 2, 51ra71-51ra71 (2010).

74. Fiorito, V., Chiabrando, D., Petrillo, S., Bertino, F. & Tolosano, E. The Multifaceted Role of Heme in Cancer. *Front. Oncol.* 9, 1540 (2020).

75. Ofori-Acquah, S. F. et al. Hemopexin deficiency promotes acute kidney injury in sickle cell disease. *Blood* 135, 1044-1048 (2020).

76. Larsen, R., Gouveia, Z., Soares, M. P. & Gozzelino, R. Heme cytotoxicity and the pathogenesis of immune-mediated inflammatory diseases. *Front. Pharmacol.* 3 MAY, 77 (2012).

77. Vinchi, F. et al. Hemopexin therapy improves cardiovascular function by preventing heme-induced endothelial toxicity in mouse models of hemolytic diseases. *Circulation* 127, 1317-1329 (2013).

78. Kishimoto, Y., Kondo, K. & Momiyama, Y. The Protective Role of Heme Oxygenase-1 in Atherosclerotic Diseases. *Int. J. Mol. Sci.* 20, (2019).

79. Chiabrando, D., Fiorito, V., Petrillo, S. & Tolosano, E. Unraveling the role of heme in neurodegeneration. *Frontiers in Neuroscience* vol. 12 (2018).

80. Roux, B. et al. An integrated analysis of plant and bacterial gene expression in symbiotic root nodules using laser-capture microdissection coupled to RNA sequencing. *Plant J.* 77, 817-837 (2014).

81. Robertsen, B. K., Åman, P., Darvill, A. G., McNeil, M. & Albersheim, P. Host-Symbiont Interactions. *Plant Physiol.* 67, 389-400 (1981).

82. Arnold, M. F. F. et al. Genome-Wide Sensitivity Analysis of the Microsymbiont *Sinorhizobium meliloti* to Symbiotically Important, Defensin-Like Host Peptides. (2017).

83. Schafer, A. et al. Small mobilizable multi-purpose cloning vectors derived from the *Escherichia coli* plasmids pK18 and pK19: selection of defined deletions in the chromosome of *Corynebacterium glutamicum*. *Gene* 145, 69-73 (1994).

84. Babu, V. M. P., Sankari, S., Budnick, J. A., Caswell, C. C. & Walker, G. C. *Sinorhizobium meliloti* YbeY is a zinc-dependent single-strand specific endoribonuclease that plays an important role in 16S ribosomal RNA processing. *Nucleic Acids Res.* 48, 332-348 (2020).

85. Barr, I. & Guo, F. Pyridine Hemochromagen Assay for Determining the Concentration of Heme in Purified Protein Solutions. *Bio-Protocol* 5, (2015).

86. Yang, J. et al. *Bradyrhizobium japonicum* senses iron through the status of heme to regulate iron homeostasis and metabolism. *Mol. Microbiol.* 60, 427-437 (2006).

87. Ghosal, A. et al. C21orf57 is a human homologue of bacterial YbeY proteins. *Biochem. Biophys. Res. Commun.* 484, 612-617 (2017).

88. Guo, Y., Wallace, S. S. & Bandaru, V. A novel bicistronic vector for overexpressing *Mycobacterium tuberculosis* proteins in *Escherichia coli*. *Protein Expr. Purif.* 65, 230-237 (2009).

89. Shah, N. B. & Duncan, T. M. Bio-layer interferometry for measuring kinetics of protein-protein interactions and allosteric ligand effects. *J. Vis. Exp.* 84, 51383 (2014).

90. Sassa, S. Sequential induction of heme pathway enzymes during erythroid differentiation of mouse friend leukemia virus-infected cells*. *J. Exp. Med.* 143, 305-315 (1976).

91. Michener, J. K., Nielsen, J. & Smolke, C. D. Identification and treatment of heme depletion attributed to overexpression of a lineage of evolved P450 monooxygenases. *Proc. Natl. Acad. Sci. U.S.A* 109, 19504-19509 (2012).

92. Poje, G. & Redfield, R. J. General methods for culturing *Haemophilus influenzae*. *Methods Mol. Med.* 71, 51-56 (2003).

93. Leigh, J. A., Signer, E. R. & Walker, G. C. Exopolysaccharide-deficient mutants of *Rhizobium meliloti* that form ineffective nodules. *Proc. Natl. Acad. Sci. U.S.A* 82, 6231-6235 (1985).

94. Ferguson, A. P. et al. Importance of unusually modified lipid A in *Sinorhizobium* stress resistance and legume symbiosis. *Mol. Microbiol.* 56, 68-80 (2005).

95. Natera, S. H. A., Guerreiro, N. & Djordjevic, M. A. Proteome analysis of differentially displayed proteins as a tool for the investigation of symbiosis. *Mol. Plant-Microbe Interact.* 13, 995-1009 (2000).

96. Tucker, A. T. et al. Discovery of Next-Generation Antimicrobials through Bacterial Self-Screening of Surface-Displayed Peptide Libraries. *Cell* 172, 618-628.e13 (2018).

97. Čermák, T. et al. A Multipurpose Toolkit to Enable Advanced Genome Engineering in Plants. *Plant Cell* 29, 1196-1217 (2017).

98. Haney, C. H. & Long, S. R. Plant flotillins are required for infection by nitrogen-fixing bacteria. *Proc. Natl. Acad. Sci. U.S.A* 107, 478-483 (2010).

99. Qi, Z., Hamza, I. & O'Brian, M. R. Heme is an effector molecule for iron-dependent degradation of the bacterial iron response regulator (Irr) protein. *Proc. Natl. Acad. Sci. U.S.A.* 96, 13056-13061 (1999).

100. Aldag, C. et al. Probing the role of the proximal heme ligand in cytochrome P450cam by recombinant incorporation of selenocysteine. *Proc. Natl. Acad. Sci. U.S.A* 106, 5481-5486 (2009).

We claim:

1. A method of sequestering heme from an environment and rendering the heme biologically inaccessible, the method comprising contacting said environment with a peptide comprising the amino acid sequence selected from the group consisting of SEQ ID NO. 1-4, wherein all residues in the peptide are D amino acids.

2. The method of claim 1, wherein the peptide comprises the amino acid sequence selected from the group consisting of SEQ ID NO: 1 and SEQ ID NO:4.

3. The method of claim 1, wherein the peptide comprises the amino acid sequence selected from the group consisting of SEQ ID NO: 1-2.

4. The method of claim 1, wherein the peptide comprises the amino acid sequence of SEQ ID NO: 1.

5. The method of claim 1, wherein the environment is selected from the group consisting of a biological sample, a cell culture, a plate, a tube, a well surface, and a medical device.

6. The method of claim 2, wherein the environment is selected from the group consisting of a biological sample, a cell culture, a plate, a tube, a well surface, and a medical device.

7. The method of claim 4, wherein the environment is selected from the group consisting of a biological sample, a cell culture, a plate, a tube, a well surface, and a medical device.

8. The method of claim 1, wherein peptide is fixed to a support, selected from the group consisting of a column matrix, a well, a plate, a slide, a tube, a dipstick, a bead, or a nanoparticle.

9. The method of claim 2, wherein the peptide is fixed to a support, selected from the group consisting of a column matrix, a well, a plate, a slide, a tube, a dipstick, a bead, or a nanoparticle.

10. The method of claim 4, wherein the peptide is fixed to a support, selected from the group consisting of a column matrix, a well, a plate, a slide, a tube, a dipstick, a bead, or a nanoparticle.

11. The method of claim 1, wherein the environment comprises stored blood.

12. The method of claim 2, wherein the environment comprises stored blood.

13. The method of claim 3, wherein the environment comprises stored blood.

14. The method of claim 4, wherein the environment comprises stored blood.

* * * * *